United States Patent
Loughhead et al.

(10) Patent No.: US 7,432,283 B2
(45) Date of Patent: *Oct. 7, 2008

(54) HETEROCYCLIC GABA$_A$ SUBTYPE SELECTIVE RECEPTOR MODULATORS

(75) Inventors: David Garrett Loughhead, Belmont, CA (US); Sanja Novakovic, San Jose, CA (US); Counde O'Yang, Sunnyvale, CA (US); David George Putman, Irvine, CA (US); Michael Soth, Milpitas, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 483 days.

This patent is subject to a terminal disclaimer.

(21) Appl. No.: 11/061,000

(22) Filed: Feb. 18, 2005

(65) Prior Publication Data

US 2005/0197330 A1    Sep. 8, 2005

Related U.S. Application Data

(60) Provisional application No. 60/545,524, filed on Feb. 18, 2004.

(51) Int. Cl.
  *A01N 43/40* (2006.01)
  *A61K 31/445* (2006.01)
  *C07D 295/00* (2006.01)
  *C07D 211/00* (2006.01)

(52) U.S. Cl. .................. 514/315; 546/184

(58) Field of Classification Search .............. None
See application file for complete search history.

(56) References Cited

U.S. PATENT DOCUMENTS

| | | | |
|---|---|---|---|
| 5,668,145 A | 9/1997 | Bright | |
| 5,705,646 A | 1/1998 | Bright et al. | |
| 5,712,303 A | 1/1998 | Faraci et al. | |
| 5,760,225 A | 6/1998 | Yuan | |
| 6,200,979 B1 | 3/2001 | Bright et al. | |
| 6,821,984 B2 * | 11/2004 | Loughhead et al. | 514/303 |
| 7,053,103 B2 * | 5/2006 | Loughhead et al. | 514/303 |
| 2003/0187014 A1 | 10/2003 | Uehikawa et al. | |

FOREIGN PATENT DOCUMENTS

| WO | WO 01/44244 A1 | 6/2001 |
|---|---|---|
| WO | WO 03/048160 A1 | 6/2003 |

OTHER PUBLICATIONS

West, Anthony R., Solid State Chemistry and Its Applications, Wiley, New York, 1988, 358.*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Hehemann, et al., "Addition of Diamines to Methylthiopyridones," *J. Heterocyclic Chem.*, (1994), pp. 393-396, vol. 31 (2).
Mohareb, et al., "Reactions with 4-Phenyl-3-thiosemicarbazide: A New Approach for the Synthesis of Pyrazole, Thiazole, Pyridine and Pyrazolo[3,4-b]-Pyridine Derivatives," *Sulfur Letters*, (1991), pp. 101-113, vol. 13(3).
Thompson, et al. "Tracazolate Reveals a Novel Ty[e of Allosteric Interactioin with Recombinant γ-Aminobutyric Acid$_A$ eceptors," (Apr. 2002), pp. 861-869, vol. 61:4.
Cooke, et al., "α-Subunit selective modulators of GABA$_A$ receptor function as CNS therapeutics," (Oct. 2002), pp. 1491-1501, vol. 12:10.

* cited by examiner

*Primary Examiner*—James O. Wilson
*Assistant Examiner*—Erich A Leeser
(74) *Attorney, Agent, or Firm*—Brian L. Buckwalter

(57) ABSTRACT

This invention relates to a method for modulating α$_2$ subtype GABA$_A$ receptors with heterocyclic compounds of formula I, and salts, solvates and prodrugs thereof. The invention further relates to novel heterocyclic compounds and pharmaceutical compositions containing said compounds. In addition the invention relates to the treatment of depression, an anxiety disorder, a psychiatric disorder, a learning or cognitive disorder, a sleep disorder, a convulsive or seizure disorder or pain (I)

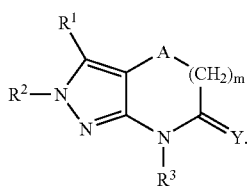

7 Claims, No Drawings ary a further 35% of the total GABA$_A$ receptor repertoire. Pharmacologically, the $\alpha_2\beta\gamma_2$ and $\alpha_3\beta_{2/3}\gamma_2$ subtypes appear to be equivalent to the BZ2 subtype. The physiological role of these subtypes has hitherto been unclear because sufficiently selective agonists or antagonists were unknown.

HETEROCYCLIC GABA$_A$ SUBTYPE SELECTIVE RECEPTOR MODULATORS

CROSS-REFERENCE TO RELATED APPLICATIONS

This application claims the benefit of priority to U.S. Ser. No. 60/545,524 filed Feb. 18, 2004, which is hereby incorporated by reference in its entirety.

FIELD OF THE INVENTION

This invention relates to a method for modulating $\alpha_2$ subtype GABA$_A$ receptors and method for treating a subject afflicted with a disease alleviated by modulating GABA$_A$ receptors with heterocyclic compounds, more particularly, to substituted 7-arylaminopyrazoles compounds and salts thereof. The invention further relates to novel heterocyclic compounds and pharmaceutical compositions containing said compounds.

BACKGROUND

GABA, 4-aminobutyric acid, is the primary inhibitory transmitter in the brain and maintains a balance between excitation and inhibition of neurons. Three major classes of GABA receptors have been identified: GABA$_A$, GABA$_B$ and GABA$_C$ receptors. GABA$_A$ and GABA$_C$ receptors are ligand-gated ion channels (LGIC), while GABA$_B$ receptors are G-protein coupled receptors. The LGIC receptors are hetero-pentamers comprised of $\alpha_{1-6}$, $\beta_{1-3}$, $\gamma_{1-3}$, $\rho_{1-3}$, $\delta$, $\epsilon$, $\pi$, and $\theta$ subunits. Each subunit contains four membrane-spanning domains. The N-terminal domain and C-domain are extracellular and the agonist/antagonist binding site is situated on the N-terminus. There is an intracellular loop between the $3^{rd}$ and $4^{th}$ membrane spanning regions (M. Chabib and G. A. R. Johnston, *J. Med. Chem.* 2000 43(8):1427-1447).

While studies are continuing to define the composition and anatomical distribution of GABA LGIC receptors, it is known that the dominant motif is $2\alpha2\beta_1\gamma$ with varying $\alpha$ subtypes. Subtype assemblies containing an $\alpha_1$ subunit are present in most areas of the brain and are thought to account for over 40% of GABA$_A$ receptors in the rat. Subtype assemblies containing $\alpha_2\beta_{2/3}\gamma_2$ and $\alpha_3\beta_n\gamma_{2/3}$ oligomers are thought to account for about 18% and 17% respectively of GABA$_A$ receptors in the rat (R. M. McKeman et al. *Trend Neurosci* 1996 19:139-143). Subtype assemblies containing an $\alpha_5$ subunit are expressed predominantly in the hippocampus and cortex and are thought to represent about 4% of GABA$_A$ receptors in the rat. The most common receptor subtype assemblies appear to be the $\alpha_1\beta_2\gamma_2$, $\alpha_2\beta_3\gamma_2$, $\alpha_3\beta_3\gamma_2$ and $\alpha_5\beta_3\gamma_2$ assemblies (H. Mohler et al. *Neuroch. Res.* 1995 20(5): 631-636).

All known GABA$_A$ receptors contain a plurality of distinct modulatory sites, one of which is the benzodiazepine (BZ) binding site. Other modulatory sites include allosteric sites for picrotoxin, barbiturates, neuroactive steroids and ethanol. The BZ binding site is the most explored of the GABA$_A$ receptor modulatory sites, and is the site through which anxiolytic drugs such as diazepam exert their effect. Early radio-ligand binding studies suggested the existence of two distinct benzodiazepine-binding sites: BZ1 and BZ2. The BZ1 subtype has been shown to be pharmacologically equivalent to a GABA$_A$ receptor comprising the $\alpha_1$ subunit in combination with a $\beta$ subunit and $\gamma_2$. This is the most abundant GABA$_A$ receptor subtype. Two other major populations are the $\alpha_2\beta\gamma_2$ and $\alpha_3\beta_{2/3}\gamma_2$ subtypes. Together these constitute approxi- The barbiturates and benzodiazepines were among the first clinically useful modulators of the GABA receptors and are among the most widely prescribed medications for anxiety, depression and other psychiatric disorders and as anticonvulsants. Benzodiazepines, with relatively mild side effects, afforded an alternative to barbiturates which possess more potent side effects. Unfortunately, many of the early benzodiazepines had relatively limited subtype selectivity resulting in sedation, dependence, cognitive impairment, ataxia, potentiation of ethanol effects, tolerance and withdrawal.

The advances in genetics and molecular biology have afforded more subtle probes of receptor subtype selectivity and hold out the promise of more selective agents. Receptors containing the $\alpha_1$, $\alpha_2$, $\alpha_3$ or $\alpha_5$ subunit have been classified as diazepam sensitive receptors while $\alpha_4$, or $\alpha_6$, are classified as diazepam insensitive receptors. In particular, the $\alpha_1$ subtype has been associated with sedation and $\alpha_1$ selective ligands have potential as sedatives (R. M. McKernan et al. *Nature Neurosci.* 2000 3(6): 587-592). Hypnotic/sedative compounds with preferential binding for the $\alpha_1$ subtype have been identified (D. J. Sanger and H. Depoortere, *CNS Drug Reviews*, 1998 47(5):323-340). Sedation, however, is undesirable in an anxiolytic agent.

Compounds that selectively bind to the benzodiazepine site, or to other allosteric sites, and enhance the ability of GABA to open GABA$_A$ receptor channels are agonists (or positive allosteric modulators) of GABA receptors. Compounds that interact with allosteric sites but negatively modulate the action of GABA are called inverse agonists (negative allosteric modulators). Inverse agonists diminish the ability of GABA to open receptor channels. A third class of compounds that bind selectively to the benzodiazepine site and yet have little or no effect on GABA activity, but can block the action of GABA$_A$ receptor agonists or inverse agonists that act at this site are referred to as antagonists. Agonists that act at the benzodiazepine site exhibit anxiolytic, sedative, and hypnotic effects, while compounds that act as inverse agonists at this site elicit anxiogenic, cognition enhancing, and proconvulsant effects.

The $\alpha_1$ selective GABA$_A$ receptor agonists alpidem and zolpidem are clinically prescribed as hypnotic agents, further suggesting that at least some of the sedation associated with known anxiolytic drugs is mediated through GABA$_A$ receptors containing the $\alpha_1$ subunit. Accordingly, GABA$_A$ receptor agonists which interact more selectively with the $\alpha_2$ and/or the $\alpha_3$ subunit relative to the $\alpha_1$ subunit should be effective anxiolytics with a reduced propensity to cause sedation. Also, agents which are antagonists or inverse agonists at the $\alpha_1$ subtype might antagonize sedation or hypnosis caused by $\alpha_1$ modulators.

Selective $\alpha_2$ and $\alpha_3$ ligands have been more difficult to identify and cross-reactivity between these receptors is common. Compounds with ten to one hundred-fold selectivity for $\alpha_{2/3}$ relative to $\alpha_1$ have been reported (see, e.g., W. R. Carling et al., WO 0044752). Experiments with point mutated mice lines suggest that the $\alpha_2$, not the $\alpha_3$, subtype is responsible for the anxiolytic activity (U. Rudolph et al. *Trends Pharmacol. Sci.* 2001 22(4):188-194; K. Löw et al. *Science* 2000 290:131-134); however, $\alpha_3$-selective inverse agonists appear to be anxiogenic and proconvulsant (I. J. Collins et al. WO 9855480). Since $\alpha_2$ and perhaps $\alpha_3$ selective ligands have the potential to modulate the (BZ2) site without activating the hypnotic sedative site (BZ1) they could afford a new class of non-sedating anxiolytics. Other non-BZ selective $\alpha_2$ GABA modulators may also exhibit anxiolytic properties without many of unwanted effects.

The selective ligands for $GABA_A$ receptors of the present invention are useful in the treatment and/or prevention of anxiety disorders, such as panic disorder with or without agoraphobia, agoraphobia without history of panic disorder, phobias including social phobias, obsessive-compulsive disorder, stress disorders including post-traumatic and acute stress disorder, and generalized or substance-induced anxiety disorder; depression or bipolar disorders such as single-episode or recurrent major depressive disorder, dysthymic disorder, bipolar I and bipolar II manic disorders; schizophrenia; learning and cognitive disorder such as Alzheimer's disease and attention deficit hyperactivity disorder; sleep disorders and disorders of circadian rhythm, e.g. in subjects suffering from the effects of jet lag or shift work; convulsive or seizure disorders such as epilepsy and pain.

Other neurotransmitter systems have been explored and drugs modulating serotonergic neurotransmission have shown promise in the treatment of anxiety related disorders. Recently, drugs such as buspirone, a partial agonist at $5HT_{1A}$ receptor, and serotonin reuptake inhibitors, commonly used as antidepressants, have been introduced. $GABA_A$ selective ligands may potentiate the effects of certain other CNS active compounds. There is evidence that selective serotonin reuptake inhibitors (SSRIs) show greater antidepressant activity when used in combination with $GABA_A$ selective ligands than when used alone.

SUMMARY OF THE INVENTION

The present invention relates to methods for preventing or treating disorders alleviated by a positive allosteric modulator of a $GABA_A$ receptor comprising administering an effective amount of a compound according to formula I

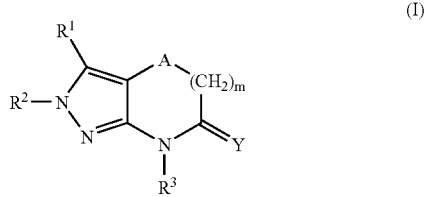

wherein:
$R^1$ is —$OR^a$, —$NR^aR^b$, —$CR^cR^dR^e$, $CHR^fR^g$, $CO_2R^a$, —$C(O)NR^aR^b$; cyano, hydrogen, $C_{2-10}$ alkynyl, $C_{1-6}$ haloalkyl, halogen, —$(CH_2)_oS(O)_nR^i$, —$(CH_2)_oS(O)_2NR^j_2$, —$NR^iSO_2R^i$, —$C(=Z)R^j$, tetrazolyl $C_{0-3}$ alkylene IIa or IIb, cycloalkenyl, aryl, or heteroaryl, where each aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, —$C(O)NR^{a'}R^{b'}$, and —$NR^{a'}R'$, where $R^{a'}$ and $R^{b'}$ are each independently selected from the group consisting of hydrogen, $C_{1-9}$alkyl, and $C_{1-9}$alkylcarbonyl, or $R^1$ is $C_{1-10}$ alkyl wherein 2 to 3 nonadjacent carbon atoms in the alkyl chain optionally can be replaced with —O—, —S— or —$NR^f$;

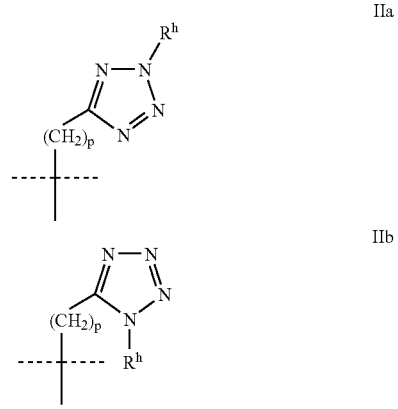

$R^2$ is hydrogen, $C_{1-6}$alkyl, $C_{3-6}$cycloalkyl, $C_{3-6}$cycloalkylalkyl, $C_{1-6}$alkylcarbonyl, $C_{1-6}$ alkylsulfonyl, aryl, or arylalkyl, wherein said aryl or arylalkyl is optionally substituted with one or more substituents independently selected from $C_{1-6}$alkyl, haloalkyl, $C_{1-6}$alkoxy, and halogen;

$R^3$ is aryl or heteroaryl, each optionally substituted with one or more substituents independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl;

$R^a$ and $R^b$ are each independently selected from the group consisting of hydrogen, $C_{1-9}$alkyl, hydroxyalkyl, $C_{1-6}$alkoxyalkyl, $C_{1-6}$alkylthioalkyl, carboxyalkyl, $C_{1-6}$-alkoxycarbonyl, $C_{1-6}$-alkoxy$C_{1-3}$-alkylcarbonyl, acyl, $C_{3-6}$cycloalkyl, $C_{3-6}$cycloalkylalkyl, di-$C_{3-6}$cycloalkyl$C_{1-3}$alkyl, $C_{1-6}$heteroalkyl, aminoalkyl, aminocarbonylalkyl, cyanoalkyl, $C_{5-8}$heterocyclyl, heterocyclylalkyl, aryl, arylalkyl, heteroaryl, heteroarylalkyl, phenylalkyl, diphenylalkyl, phenylsulfonyl optionally substituted as described for phenyl below, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

$R^c$ is hydrogen, hydroxy, $C_{1-6}$alkoxy, or —$NR^{a'''}R^{b'''}$;

$R^d$ and $R^e$ are each independently selected from the group consisting of hydrogen, $C_{1-9}$alkyl, hydroxyalkyl, $C_{1-6}$alkoxyalkyl, $C_{1-6}$alkylthioalkyl, heteroalkyl, heterocyclyl, heterocyclylalkyl, $C_{3-6}$cycloalkyl, $C_{3-6}$cycloalkylalkyl, di-$C_{3-6}$cycloalkyl-$C_{1-3}$alkyl, aryl, arylalkyl, heteroaryl, heteroarylalkyl, phenylalkyl, diphenyl-$C_{1-3}$alkyl, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, and halogen; or $R^c$ and $R^d$ are taken together to form a divalent group selected from $C_{1-6}$alkylidenyl, $C_{1-6}$heteroalkylidenyl, $C_{3-6}$cycloalkylidenyl, $C_{3-6}$cycloalkyl-alkylidenyl, $C_{3-6}$cycloalkylalkyl-alkylidenyl, $C_{3-6}$heterocyclylidenyl, $C_{3-6}$heterocyclyl-$C_{1-3}$alkylidenyl, $C_{3-6}$heterocyclalkyl-$C_{1-3}$alkylidenyl, aryl-$C_{1-3}$alkylidenyl, aryl-$C_{1-3}$alkyl-alkylidenyl, heteroaryl-$C_{1-3}$alkylidenyl, and heteroarylalkyl-$C_{1-3}$alkylidenyl, wherein each of said cycloalkyl, aryl, or heteroaryl groups is optionally substituted with one or more substituents independently selected from $C_{1-6}$alkyl, haloalkyl, $C_{1-6}$alkoxy, amino, alkylamino, dialkylamino, and halogen; or $R^d$ and $R^e$ are taken together with the carbon to which they are attached to form a cycloalkyl or heterocyclyl ring;

$R^f$ is hydrogen or $C_{1-10}$ alkyl;

$R^g$ is $C_{2-10}$ alkenyl;

$R^h$ is H or $C_{1-3}$ alkyl;

$R^i$ is $C_{1-6}$ alkyl, $C_{2-6}$ alkenyl, $C_{1-6}$ heteroalkyl or phenyl optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen;

$R^j$ is hydrogen, $C_{1-6}$ alkyl, $C_{2-6}$ alkenyl, or $C_{1-6}$ heteroalkyl;

A is $CH_2$, O, S or $NR^f$;

Y is O or H, H;

Z is O or $NOR^f$;

$R^{a'''}$ and $R^{b'''}$ are each independently selected from the group consisting of hydrogen, $C_{1-9}$alkyl, hydroxyalkyl, $C_{1-6}$alkoxyalkyl, $C_{1-6}$alkylthioalkyl, carboxyalkyl, $C_{1-6}$-alkoxycarbonyl, $C_{1-6}$-alkoxy$C_{1-3}$-alkylcarbonyl, acyl, $C_{3-6}$cycloalkyl, $C_{3-6}$cycloalkylalkyl, di-$C_{3-6}$cycloalkyl-$C_{1-3}$alkyl, $C_{1-6}$heteroalkyl, aminoalkyl, aminocarbonylalkyl, cyanoalkyl, $C_{5-8}$heterocyclyl, heterocyclylalkyl, aryl, arylalkyl, heteroaryl, heteroarylalkyl, phenylalkyl, diphenyl-$C_{1-3}$alkyl, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$alkyl, haloalkyl, $C_{1-6}$alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

m is 1 or 2;

n is 0 to 2;

o is 0 to 6;

p is 0 to 3;

or individual isomers, racemic or non-racemic mixtures of isomers, or pharmaceutically acceptable salts thereof.

The present invention further relates to compounds according to formula I which are positive allosteric modulators of a $GABA_A$ receptor and pharmaceutical composition containing compounds according to formula I.

DETAILED DESCRIPTION OF THE INVENTION

In one embodiment of the present invention there is provided a compound according to formula I wherein wherein $R^1$ is $CHR^fR^g$, $C_{2-10}$ alkynyl, $C_{1-6}$ haloalkyl, cyano, —$(CH_2)_oS(O)_nR^i$, —$(CH_2)_oS(O)_2NR^j{}_2$, —$NR^fSO_2R^i$, —$C(=Z)R^j$, tetrazolyl $C_{0-3}$ alkylene IIa or IIb, or $C_{1-10}$ alkyl wherein 2 to 3 nonadjacent carbon atoms in the alkyl chain optionally can be replaced with —O—, —S— or —$NR^f$; $R^2$ is hydrogen, $C_{1-6}$ alkyl, $C_{3-6}$ cycloalkyl, $C_{3-6}$ cycloalkyl-$C_{1-3}$ alkyl, $C_{1-3}$ alkoxycarbonyl $C_{1-3}$ alkyl, $C_{1-6}$ haloalkyl; $R^3$, $R^{a''}$, $R^{b''}$, $R^f$, $R^g$, $R^h$, $R^i$, $R^j$, A, Y, Z, m, n, o, p are as defined hereinabove; and, individual isomers, racemic or non-racemic mixtures of isomers, solvates hydrates or pharmaceutically acceptable salts thereof.

In another embodiment of the present invention there is provided a compound according to formula I wherein wherein $R^1$ is $CHR^fR^g$, $C_{2-10}$ alkynyl, $(CH_2)_oS(O)_nR^i$, $(CH_2)_oS(O)_2NR^j{}_2$, —$NR^fSO_2R^i$, $C_{1-6}$ haloalkyl or tetrazolyl $C_{0-3}$ alkylene IIa or IIb; $R^i$ is $C_{1-6}$ alkyl; $R^2$ is hydrogen or $C_{1-6}$ alkyl; $R^3$ is optionally substituted aryl; A is $CH_2$; Y is H,H; m is 1; $R^a$, $R^b$, $R^{a'}$, $R^{b'}$, $R^{a''}$, $R^{b''}$, $R^{a'''}$, $R^{b'''}$, $R^c$, $R^d$, $R^e$, $R^f$, $R^g$, $R^h$, $R^j$, n, o, p are as defined hereinabove; and, individual isomers, racemic or non-racemic mixtures of isomers, or pharmaceutically acceptable salts thereof.

In another embodiment of the present invention there is provided a compound according to formula I wherein $R^1$ is $(CH_2)_oS(O)_nR^i$, $(CH_2)_oS(O)_2NR^j{}_2$, —$NR^fSO_2R^i$; $R^2$ is methyl or ethyl; n is 2; o is 0, $R^i$ is $C_{1-6}$ alkyl; $R^2$ is hydrogen or $C_{1-6}$ alkyl; $R^3$ is optionally substituted aryl; A is $CH_2$; Y is H,H; m is 1; $R^{a''}$, $R^{b''}$, $R^c$, $R^d$, $R^e$, $R^j$, p are as defined hereinabove; and, individual isomers, racemic or non-racemic mixtures of isomers, or pharmaceutically acceptable salts thereof.

In another embodiment of the present invention there is provided a compound according to formula I wherein $R^1$ is ethynyl, $R^2$ is methyl or ethyl; $R^3$ is optionally substituted aryl; A is CH$_2$; Y is H,H; m is 1; R$^{a'''}$, R$^{b'''}$, R$_{a'''}$ are as defined hereinabove; and, individual isomers, racemic or non-racemic mixtures of isomers, or pharmaceutically acceptable salts thereof.

In another embodiment of the present invention there is provided a compound according to formula I wherein R$^1$ is tetrazolyl C$_{0-3}$ alkylene IIa; R$^2$ is methyl or ethyl; R$^3$ is optionally substituted aryl; A is CH$_2$; Y is H,H; m is 1; R$^{a''}$, R$^{b''}$, R$_h$, p are as defined hereinabove; and, individual isomers, racemic or non-racemic mixtures of isomers, or pharmaceutically acceptable salts thereof.

In another embodiment of the present invention there is provided a compound according to formula I wherein R$^1$ is tetrazolyl C$_{0-3}$ alkylene IIb; R$^2$ is methyl or ethyl; R$^3$ is optionally substituted aryl; A is CH$_2$; Y is H,H; m is 1; R$^{a''}$, R$^{b''}$, R$^h$, p are as defined hereinabove; and, individual isomers, racemic or non-racemic mixtures of isomers, or pharmaceutically acceptable salts thereof.

In another embodiment of the present invention there is provided a method of preventing or treating disorders alleviated by a positive allosteric modulator of a GABA$_A$ receptor comprising administering to a patient in need thereof an effective amount of a compound according to formula I

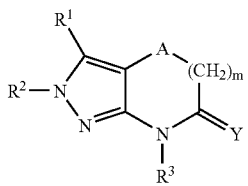

(I)

wherein R$^1$, R$^2$, R$^3$, R$^a$, R$^b$, R$^{a'}$, R$^{b'}$, R$^{a''}$, R$^{b''}$, R$^{a'''}$, R$^{b'''}$, R$^c$, R$^d$, R$^e$, R$^f$, R$^g$, R$^h$, R$^i$, R$^j$, A, Y, Z, m, n, o, p are as defined hereinabove; and, individual isomers, racemic or non-racemic mixtures of isomers, or pharmaceutically acceptable salts thereof.

In another embodiment of the present invention there is provided a method of preventing or treating disorders alleviated by a positive allosteric modulator of a GABA$_A$ receptor comprising administering an effective amount of a compound according to formula I wherein R$^1$ is CR$^c$R$^d$R$^e$, CHR$^f$R$^g$, halogen, C$_{2-10}$ alkynyl, —(CH)$_o$S(O)$_n$R$^i$, —(CH$_2$)$_o$S(O)$_2$NR$^j$$_2$, —NR$^f$SO$_2$R$^i$, —C(=Z)R$^j$, tetrazolyl C$_{0-3}$ alkylene IIa or IIb, OR$^a$, or NR$^a$R$^b$; R$^3$ is optionally substituted aryl; R$^a$ and R$^b$ are independently hydrogen or C$_{1-6}$ alkyl; R$^c$ is (i) hydrogen, hydroxy, C$_{1-6}$alkoxy, or —NR$^{a'''}$R$^{b'''}$; and R$^d$ and R$^e$ are each independently selected from the group consisting of hydrogen and C$_{1-9}$alkyl, or, (ii) R$^c$ and R$^d$ taken together form a divalent group selected from C$_{1-9}$alkylidenyl, C$_{1-6}$heteroalkylidenyl, C$_{3-6}$cycloalkylidenyl, C$_{3-6}$cycloalkyl-alkylidenyl, C$_{3-6}$cycloalkylalkyl-alkylidenyl, C$_{3-6}$heterocyclylidenyl, C$_{3-6}$heterocyclyl-C$_{1-3}$alkylidenyl, C$_{3-6}$heterocyclylalkyl-C$_{1-3}$alkylidenyl, aryl-C$_{1-3}$alkylidenyl, aryl-C$_{1-3}$alkyl-alkylidenyl, heteroaryl-C$_{1-3}$alkylidenyl, and heteroarylalkyl-C$_{1-3}$alkylidenyl, wherein each of said cycloalkyl, aryl, or heteroaryl groups is optionally substituted with one or more substituents independently selected from C$_{1-6}$alkyl, haloalkyl, C$_{1-6}$alkoxy, amino, alkylamino, dialkylamino, and halogen, and Re is hydrogen or C$_{1-9}$alkyl; and, R$^e$ is hydrogen, C$_{1-9}$alkyl or C$_{1-6}$alkoxyalkyl; R$^f$ is hydrogen or C$_{1-9}$alkyl; R$^g$ is C$_{2-10}$ alkenyl; R$^i$ is C$_{1-6}$ alkyl; R$^2$, R$^a$, R$_{a''}$, R$^{b''}$, R$^{a'''}$, R$^{b'''}$, R$^h$, R$^j$, A, Y, Z, m, n, o, p are as defined hereinabove; and, individual isomers, racemic or non-racemic mixtures of isomers, or pharmaceutically acceptable salts thereof.

In another embodiment of the present invention there is provided a method of preventing or treating disorders alleviated by a positive allosteric modulator of GABA$_A$ receptor comprising administering to a patient in need thereof an effective amount of a compound according to formula I wherein R$^1$ is CR$^c$R$^d$R$^e$, C$_{2-10}$ alkynyl, chlorine, bromine, —(CH)$_o$S(O)$_n$R$^i$, —(CH$_2$)$_o$S(O)$_2$NR$^j$$_2$, —NR$^f$SO$_2$R$^i$, or —C(=Z)R$^j$; R$^3$ is optionally substituted aryl; R$^c$ and R$^d$ are hydrogen and R$^e$ is C$_{1-6}$alkyl, or R$^c$ and R$^d$ together are C$_{1-9}$alkylidenyl and R$^e$ is hydrogen or C$_{1-9}$alkyl; R$^f$ is hydrogen or C$_{1-10}$ alkyl; R$^8$ is C$_{2-10}$ alkenyl; R$^i$ is C$_{1-3}$ alkyl; R$^2$, R$^3$, R$^{a''}$, R$^{b''}$, R$^j$, A, Y, Z, m, n, o, p are as defined hereinabove; and, individual isomers, racemic or non-racemic mixtures of isomers, or pharmaceutically acceptable salts thereof.

In another embodiment of the present invention there is provided a method of preventing or treating disorders alleviated by a positive allosteric modulator of GABA$_A$ receptor comprising administering an effective amount of a compound according to formula I wherein R$^1$ is IIa or IIb; R$^3$ is optionally substituted aryl; R$^2$, R$^h$, R$^{a''}$, R$^{b''}$, A, Y, m, p are as defined hereinabove; and, individual isomers, racemic or non-racemic mixtures of isomers, or pharmaceutically acceptable salts thereof.

In another embodiment of the present invention there is provided a pharmaceutical composition for preventing or treating disorders alleviated by a positive allosteric modulator of a GABA$_A$ receptor said composition comprising a therapeutically effective amount of a compound of a compound according to formula I wherein R$^1$, R$^2$, R$^3$, R$^a$, R$^b$, R$^{a'}$, R$^{b'}$, R$^{a''}$, R$^{b''}$, R$^{a'''}$, R$^{b'''}$, R$^c$, R$^d$, R$^e$, R$^f$, R$^g$, R$^h$, R$^i$, R$^j$, A, Y, Z, m, n, o, p are as defined hereinabove; and, individual isomers, racemic or non-racemic mixtures of isomers, solvates hydrates, prodrugs or pharmaceutically acceptable salts thereof admixed with at least one diluent, excipient or carrier.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The phrase "as defined hereinabove" refers to the first definition provided in the Summary of the Invention.

The term "alkyl" or "lower alkyl" as used herein means a monovalent linear or branched saturated hydrocarbon radical, consisting solely of carbon and hydrogen atoms, having from one to ten carbon atoms inclusive, unless otherwise indicated. "Lower alkyl" implies an "alkyl" group having from one to six carbon atoms. Examples of alkyl radicals include, but are not limited to, methyl, ethyl, propyl, isopropyl, isobutyl, sec-butyl, tert-butyl, pentyl, n-hexyl, and the like.

The term "alkenyl" as used herein denotes an unsubstituted hydrocarbon chain radical having from 2 to 10 carbon atoms having one or two olefinic double bonds. C$_{2-10}$ alkenyl" as used herein refers to an alkenyl composed of 2 to 10 carbons. Examples are vinyl, 1-propenyl, 2-propenyl (allyl) or 2-butenyl (crotyl).

The term "alkynyl" as used herein denotes an unbranched or branched hydrocarbon chain radical having from 2 to 10 carbon atoms, and having one or where possible two triple bonds. C$_{2-10}$ alkynyl" as used herein refers to an alkynyl composed of 2 to 10 carbons Examples are ethynyl, 1-propynyl, 2-propynyl, 1-butynyl, 2-butynyl or 3-butynyl.

The term "alkylene" as used herein means a divalent linear or branched saturated hydrocarbon radical consisting solely of carbon and hydrogen atoms, having from one to six carbon atoms inclusive, unless otherwise indicated. Examples of alkylene radicals include, but are not limited to, methylene, ethylene, propylene, 2-methylethylene, 3-methylpropylene, 2-ethylethylene, pentylene, hexylene, and the like.

The term "alkoxy" as used herein means a radical —OR, wherein R is a lower alkyl radical as defined herein. Examples of alkoxy radicals include, but are not limited to, methoxy, ethoxy, isopropoxy, and the like.

The term "alkylthio" or "thioalkyl" as used herein means an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an-S-alkyl wherein alkyl is $C_{1-10}$.

The terms "alkylsulfonyl" and "arylsulfonyl" as used herein denotes a group of formula —S(=O)$_2$R wherein R is alkyl or aryl respectively and alkyl and aryl are as defined herein.

The terms "alkylsulfonylamino" and "arylsulfonylamino" as used herein denotes a group of formula —NR'S(=O)$_2$R wherein R is alkyl or aryl respectively, R' is hydrogen or $C_{1-3}$ alkyl, and alkyl and aryl are as defined herein.

The terms "alkylsulfonyloxy" and "arylsulfonyloxy" as used herein denotes a group of formula —OS(=O)$_2$R wherein R is alkyl or aryl respectively and alkyl and aryl are as defined herein.

The term "aminosulfonyl (or sulfamoyl)" as used herein refers to the radical —S(O)$_2$NH$_2$. The terms "alkylaminosulfonyl (or N-alkylsulfamoyl)" and "dialkylaminosulfonyl (N,N-dialkylsulfamoyl)" as used herein refers to the radical —S(O)$_2$NR'R", wherein R' and R" are hydrogen and lower alkyl and R' and R" are independently lower alkyl respectively. Examples of alkylaminosulfonyl include, but are not limited to methylaminosulfonyl, iso-propylaminosulfonyl. Examples of dialkylaminosulfonyl include, but are not limited to dimethylaminosulfonyl, iso-propyl-methylaminosulfonyl. The prefix N-alkyl or N,N-dialkyl can be replaced with aryl, heteroaryl, heterocyclyl or other radical to indicate a case where the amine is substituted with a group other than alkyl.

The term "aminosulfonylamino" as used herein refers to the radical —NR—S(O)$_2$NR'R". The terms "N-alkylaminosulfonylamino or aminosulfonyl-N'-alkylamino" as used herein refers to the radical —NRS(O)$_2$NH$_2$ or —NHS(O)$_2$NHR' wherein R and R are alkyl as defined herein.

The term "acylamino" as used herein denotes a group of formula —NHC(=O)R wherein R is hydrogen or lower alkyl as defined herein.

The term "carbamoyl" or "aminocarbonyl" as used herein means the radical —CONH$_2$. The prefix "N-alkylcabamoyl" and "N,N-dialkylcarbamoyl" means a the radical CONHR' or CONR'R" respectively wherein the R' and R" groups are independently alkyl as defined herein. The prefix N-arylcabamoyl" denotes the radical CONHR' wherein R' is an aryl radical as defined herein. "Aminocarbonylalkyl" as used herein refers to a group RR' wherein R represents alkylene and R' is CONRR' where r and R' are alkyl or hydrogen.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)$_n$—, RHN(CH$_2$)$_n$—, and R$_2$N(CH$_2$)n- respectively wherein n is 1 to 6 and R is alkyl as defined above. "$C_{1-10}$ alkylamino" as used herein refers to an-aminoalkyl wherein alkyl is $C_{1-10}$. The term "phenylamino" as used herein refers to —NHPh wherein Ph represents an optionally substituted phenyl group.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy $C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "cycloalkyl" as used herein means a monovalent saturated carbocyclic radical consisting of one or more rings, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of cycloalkyl radicals include, but are not limited to, cyclopropyl, cyclobutyl, 3-ethylcyclobutyl, cyclopentyl, cycloheptyl, and the like.

The term "cycloalkylalkyl" as used hereinmeans a radical —R'R", wherein R' is an alkylene radical, and R" is a cycloalkyl radical as defined herein. Examples of cycloalkylalkyl radicals include, but are not limited to, cyclopropylmethyl, cyclohexylmethyl, cyclopentylethyl, and the like.

The term "cycloalkenyl" as used herein means a monovalent unsaturated carbocyclic radical consisting of one or more rings, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of cycloalkenyl radicals include, but are not limited to, cyclobuten-1-yl, 3-ethylcyclobuten-1-yl, cyclopenten-1-yl, 3-fluorocyclohepten-1-yl, and the like.

The term "halogen" or "halo" as used hereinmeans the radical fluoro, bromo, chloro, or iodo, and combinations thereof.

The term "haloalkyl" as used herein means a lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

The term "aryl" as used herein means a monocyclic or bicyclic radical of 6 to 12 ring carbon atoms having at least one aromatic ring, with the understanding that the attachment point of the aryl radical will be on an aromatic ring. The aryl radical is optionally substituted independently with one or more substituents, preferably one to three substituents, independently selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —SO$_2$NR'R" (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. More specifically the term aryl includes, but is not limited to, phenyl, naphthyl, tetrahydronaphthyl, 3,4-methylenedioxyphenyl, 1,2,3,4-tetrahydroquinolin-7-yl, 1,2,3,4-tetrahydroisoquinoline-7-yl, and the like.

The term "heteroaryl" as used herein means a monocyclic or bicyclic radical of 5 to 12 ring atoms having at least one aromatic ring containing one, two, or three ring heteroatoms selected from nitrogen, oxygen, and sulfur, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. The heteroaryl ring is optionally substituted independently with one or more substituents, preferably one or two substituents, selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —$SO_2NR'R''$ (where R' and R'' are independently hydrogen or alkyl), alkoxy, haloalkoxy, alkoxycarbonyl, carbamoyl, hydroxy, halo, nitro, cyano, thio, methylenedioxy or ethylenedioxy. More specifically the term heteroaryl refers to monocyclic aromatic moieties having 5 to 6 ring atoms, including 1 to 2 heteroatoms, and includes, but is not limited to, pyridinyl, furanyl, thienyl, thiazolyl, isothiazolyl, triazolyl, imidazolyl, isoxazolyl, pyrrolyl, pyrazolyl, and pyrimidinyl, and derivatives thereof. In addition, the term heteroaryl refers to bicyclic aromatic moieties having 9 to 10 ring atoms, including 1 to 3 heteroatoms, and includes, but is not limited to, benzofuranyl, tetrahydrobenzofuranyl, isobenzofuranyl, benzothiazolyl, benzoisothiazolyl, benzotriazolyl, indolyl, isoindolyl, benzoxazolyl, quinolinyl, 5,6,7,8-tetrahydroquinolinyl, isoquinolinyl, 5,6,7,8-tetrahydroisoquinolinyl, benzimidazolyl, benzisoxazolyl, and benzothienyl, and derivatives thereof.

The term "heteroalkyl" as sued herein means an alkyl radical as defined herein wherein one, two, or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; and $R^b$ and $R^c$ are independently selected from the group consisting of hydrogen, acyl, alkyl, cycloalkyl, or cycloalkylalkyl; and when n is 0, $R^d$ is hydrogen, alkyl, cycloalkyl, and cycloalkylalkyl. When n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-methoxyethyl, 2-ethoxyethyl, 3-methoxypropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "heterocyclyl" as used herein means a saturated or unsaturated non-aromatic monocyclic or bicyclic radical of 3 to 10 ring atoms in which one or two ring atoms are heteroatom containing groups selected from NR', O, or $S(O)_n$ (where R' is alkyl, heteroalkyl, or hydrogen, and n is an integer from 0 to 2), the remaining ring atoms being carbon. The heterocyclyl radical is optionally substituted with one or more substituents selected from the group consisting of hydroxy, oxo, alkyl, haloalkyl, hydroxyalkyl, heteroalkyl, and acyl. The term heterocyclyl includes, but is not limited to, tetrahydropyranyl, piperidino, tetrahydropyrimidin-5-yl, tetrahydropyrimidin-1-yl, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, tetrahydroquinolin-1-yl and tetrahydroisoquinolin-2-yl, and the like.

The term "arylalkyl" as used herein means a radical —R'R'' where R' is an alkylene radical and R'' is an aryl radical as defined herein. Examples of arylalkyl radicals include, but are not limited to, 4-fluorophenylmethyl, benzyl, 3,4-dichlorophenylethyl, and the like.

The term "heteroarylalkyl" as used herein means a radical —R'R'' where R' is an alkylene radical and R'' is an heteroaryl radical as defined herein. Examples of heteroarylalkyl radicals include, but are not limited to, such as 3-pyridinylmethyl, 4-chloropyrimidin-2-ylmethyl, 2-thiophen-2-ylethyl, and the like.

The term "heterocyclylalkyl" as used herein means a radical —R'R'' where R' is an alkylene radical and R'' is an heterocyclyl radical as defined herein. Examples of heterocyclylalkyl radicals include, but are not limited to, tetrahydropyran-2-ylmethyl, 2-piperidinylmethyl, 3-piperidinylmethyl, morpholin-1-ylpropyl, and the like.

The term "alkylamino" as used herein means a radical —NR'R'', wherein R' is hydrogen or alkyl, and R'' is an alkyl radical as defined herein. Examples of alkylamino radicals include, but are not limited to, methylamino, ethylamino, cyclopropylmethylamino, dicyclopropylmethylamino, dimethylamino, methylethylamino, diethylamino, di(1-methylethyl)amino, and the like. The term dialkylamino refers to the case where R' is alkyl.

The term "acyl" as used herein means a formyl radical of the formula —C(O)H, or a carbonyl radical of the formula —C(O)R', where R' is selected from the group consisting of $C_{1-8}$alkyl, alkoxyalkyl, cycloalkyl, cycloalkylalkyl, haloalkyl, heteroalkyl, heterocyclyl, heterocyclylalklyl, aryl, arylalkyl, heteroaryl, heteroarylalkyl, alkoxy, or amino, as defined herein, where said amino is optionally monosubstituted or disubstituted with alkyl, or said amino is contained in a pyrrolidinyl, piperidinyl, morpholinyl, or piperazinyl group.

The term "alkylidenyl" as used herein means a bivalent radical =CRR', wherein R and R' are independently an alkyl radical or hydrogen, as defined herein. Examples of alkylidenyl radicals include, but are not limited to, ethylidenyl, propylidenyl, butylidenyl, and the like.

The term "cycloalkylidenyl" as used herein means a bivalent radical =CRR', wherein R and R' are taken together with the carbon to which they are attached to form a bivalent cycloalkyl radical, as defined herein. Examples of cycloalkylidenyl radicals include, but are not limited to, cyclopentylidenyl, 3-fluorocyclohexylidenyl, and the like.

"Cycloalkyl-alkylidenyl" means a bivalent radical =CRR', wherein R is an alkyl radical or hydrogen, and R' is a cycloalkyl radical, as defined herein. Examples of cycloalkyl-alkylidenyl radicals include, but are not limited to, cyclopropylmethylidenyl, cyclohexylmethylidenyl, 1-cyclopentylethylidenyl, and the like. $C_{4-7}$ cycloalkyl $C_{1-3}$ alkylidenyl refers to a moiety in which the cycloalkyl group is 4-7 carbon atoms and the alkylidenyl group is 1-3 carbon atoms.

The term "cycloalkylalkyl-alkylidenyl" as used herein means a bivalent radical =CRR', wherein R is an alkyl radical or hydrogen, and R' is a cycloalkylalkyl radical, as defined herein. Examples of cycloalkylalkyl-alkylidenyl radicals include, but are not limited to, 2-cyclopentylethylidenyl, 1-cyclohexylpropyliden-2-yl, and the like.

The term "heteroalkylidenyl" as used herein means a bivalent radical =CRR', wherein R is an heteroalkyl radical, an haloalkyl radical, an alkyl radical, or hydrogen, and R' is an heteroalkyl radical or an haloalkyl radical, as defined herein. Examples of heteroalkylidenyl radicals include, but are not limited to, 3,3,3-trifluoropropylidenyl, 2-hydroxybutylidenyl, 3-aminopropylidenyl, and the like.

The term "heterocyclylidenyl" as used herein means a bivalent radical =CRR', wherein R and R' are taken together with the carbon to which they are attached to form a bivalent heterocyclyl radical, as defined herein. Examples of heterocyclylidenyl radicals include, but are not limited to, pyrrolidinyliden-2-yl, tetrahydropyranyliden-4-yl, piperidinyliden-4-yl, and the like.

The term "heterocyclyl-alkylidenyl" as sued herein means a bivalent radical =CRR', wherein R is an alkyl radical or hydrogen, and R' is an heterocyclyl radical, as defined herein. Examples of heterocyclyl-alkylidenyl radicals include, but are not limited to, 4-piperidinylmethylidenyl, 4-methyl-1-piperazinylmethylidene, and the like.

The term "heterocyclylalkyl-alkylidenyl" as used herein means a bivalent radical =CRR', wherein R is an alkyl radical or hydrogen, and R' is an heterocyclylalkyl radical, as defined herein. Examples of heterocyclylalkyl-alkylidenyl radicals include, but are not limited to, 2-tetrahydropyran4-yl)ethylidenyl, 1-(piperidin-3-yl)propyliden-2-yl, and the like.

The term "arylalkylidenyl" as used herein means a bivalent radical =CRR', wherein R is an aryl radical, an alkyl radical, or hydrogen, and R' is an aryl radical, as defined herein. Examples of arylalkylidenyl radicals include, but are not limited to, 4-chlorophenylmethylidenyl, 6,7-dimethoxynaphth-2-ylmethylidenyl, and the like.

The term "arylalkyl-alkylidenyl" as used herein means a bivalent radical =CRR', wherein R is an alkyl radical or hydrogen, and R' is an arylalkyl radical, as defined herein. Examples of arylalkyl-alkylidenyl radicals include, but are not limited to, 2-(4-trifluoromethylphenyl)ethylidenyl, 1-(3, 4-dichlorophenyl)propyliden-2-yl, and the like.

The term "heteroarylalkylidenyl" as used herein means a bivalent radical =CRR', wherein R is an alkyl radical or hydrogen, and R' is an heteroaryl radical, as defined herein. Examples of heteroarylalkylidenyl radicals include, but are not limited to, 3-pyridinylmethylidenyl, 4-chloro-2-pyrimidinylmethylidenyl, and the like.

The term "heteroarylalkyl-alkylidenyl" as used herein means a bivalent radical =CRR', wherein R is an alkyl radical or hydrogen, and R' is an heteroarylalkyl radical, as defined herein. Examples of heteroarylalkyl-alkylidenyl radicals include, but are not limited to, 2-(4-trifluoromethylpyrimidinyl)ethylidenyl, 1-(thiophen-2-yl)propyliden-2-yl, and the like.

The term "phenylsulfonyl" as used herein means a monovalent radical $C_6H_5SO_2$—. A phenyl group can be unsubstituted or substituted with one or more suitable substituents as defined in the definition of "aryl".

The term "alkoxycarbonyl" as used herein means a monovalent radical —C(O)—OR, wherein R is a lower alkyl radical as defined herein. Examples of alkoxycarbonyl radicals include, but are not limited to, methoxycarbonyl, ethoxycarbonyl, butoxycarbonyl, and the like.

The term "alkoxyalkylcarbonyl" means a monovalent radical (O)—R—OR', wherein R is an alkylene radical as defined herein and R' is a lower alkyl radical as defined herein. Examples of alkoxyalkylcarbonyl radicals include, but are not limited to, methoxymethylcarbonyl, ethoxymethylcarbonyl, and the like.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively include hydroxyl groups protected as acetates, haloalkyl carbonates, benzyl ethers, alkylsilyl ethers, heterocyclyl ethers, methyl or alkyl ethers, and the like. Protective or blocking groups for carboxyl groups are similar to those described for hydroxyl groups, and are preferably tert-butyl, benzyl or methyl esters.

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by exposure to mild acids in the case of BOC, e.g., trifluoroacetic acid or hydrochloric acid in ethyl acetate as a solvent; or by catalytic hydrogenation in the case of CBZ.

"Hydroxy-protecting group" means the protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include alkyl ether groups, the tetrahydropyranyl, silyl, trialkylsilyl ether groups, and the allyl group.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like. "Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, J. *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

"Substantially pure" means at least about 90 mole percent, more preferably at least about 95 mole percent, and most preferably at least about 98 mole percent of the desired enantiomer or stereoisomer is present compared to other possible configurations.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
(i) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (ii) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I or Formula II are prepared by modifying one or more functional group(s) present in the compound of Formula I or Formula II in such a way that the modification(s) may be cleaved in vivo to release the parent compound. Prodrugs include compounds of Formula I or Formula II wherein a hydroxy, amino, sulfhydryl, carboxy or carbonyl group in a compound of Formula I or Formula II is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I or Formula II, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp. 352-401; *Design of prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Disease state" means any disease, condition, symptom, or indication.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state;
(ii) inhibiting the disease state, i.e., arresting the development of the disease state or its clinical symptoms, or
(iii) relieving the disease state, i.e., causing temporary or permanent regression of the disease state or its clinical symptoms.

"Mood disorders" or "affective disorders" means psychopathologic conditions in which a pervasive disturbance of mood constitutes the core manifestation. These terms subsume anxiety and related neuroses, especially the depressive form. Examples of "mood disorders" or "affective disorders" include, but are not limited to, depression, major depressive disorder, single episode depression, recurrent depression, child abuse induced depression, postpartum depression, dysthemia, unipolar disorder, bipolar disorder with manifestations of insomnia and eating disorder, dysthymic disorder, double depression, morbid and clinical depression, mania and cyclothymia.

Compound Preparation

The compounds of Formula I described herein may be prepared by standard synthetic methods. In particular, certain compounds of Formula I may be prepared from intermediate bromopyrazole 7, the preparation of which is illustrated in Scheme 1 for Formula I, where $R^2$, $R^3$ and n are as described above.

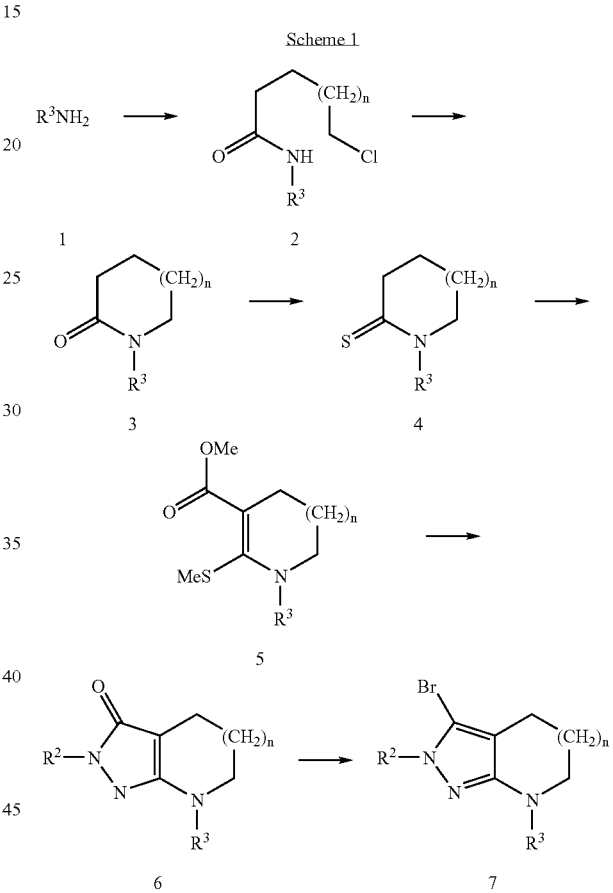

According to Scheme 1, optionally substituted aniline 1 ($R^3$ is phenyl optionally independently substituted with one to three substituents) is acylated with a carboxylic acid derivative having an ω-leaving group, such as halogen, to provide amide 2, which is subsequently cyclized under basic conditions onto the carbon possessing the leaving group to generate 3. The N-aryl lactam 3 is converted into the corresponding thione 4, deprotonated, C-acylated, and concurrently S-methylated to form methyl carboxylate 5. Treatment of 5 with $R^2$-substituted hydrazine provides pyrazolinone-fused heterocycle 6, which is brominated to provide bromopyrazole 7. Compounds in which $R^3$ is heteroaryl can be prepared similarly by replacing the aniline with an optionally substituted heteroarylamine. For example, compound 1-12 (Table 1) is prepared starting from 2-dimethylamino-4-methyl-5-amino pyridine (T. Ebara et al. JP54028330 [CAN 91:40904]).

Scheme 2

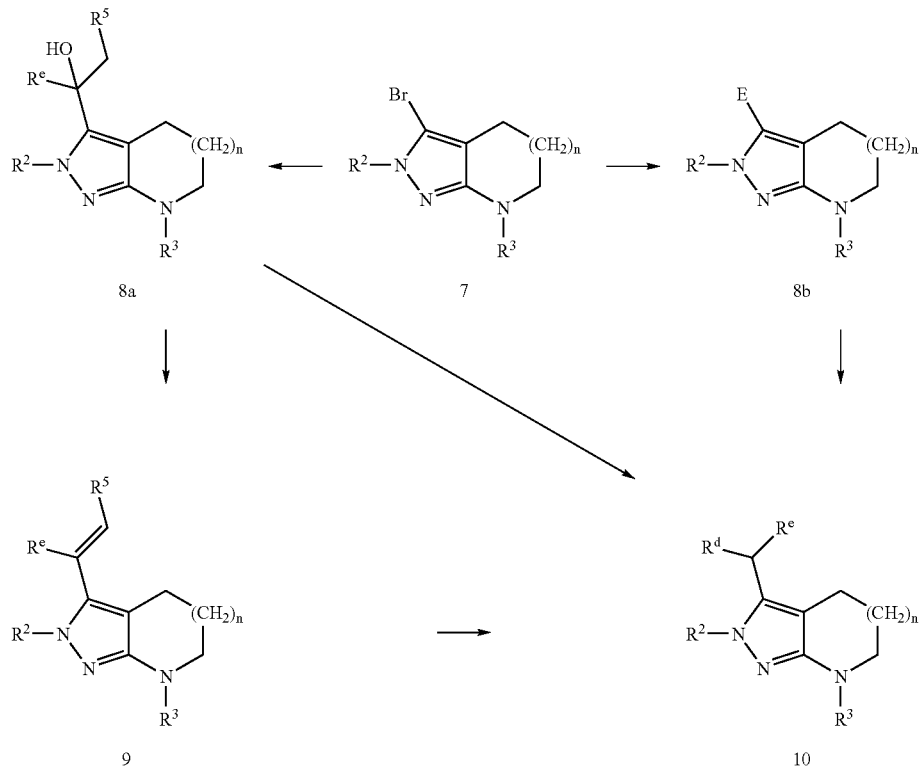

Intermediate bromopyrazole 7 is converted into the compounds of Formula I as illustrated in Scheme 2 for Formula I, where $R^2$, $R^3$, $R^5$, $R^d$, $R^e$, and n are as described above. Intermediate bromopyrazole 7 is metallated and reacted with an aldehyde or ketone ($R^eC(O)CH_2R^5$) to provide alcohol 8a which may be eliminated to the corresponding alkene 9. Depending upon the nature of $R^e$ and $R^5$, the double bond stereochemistry resulting from the elimination reaction to alkene 9 may be either an E-double bond, a Z-double bond, or a mixture of both in various ratios. Subsequent reduction of alkene 9, by hydrogenation for example, provides alkane 10. $R^d$ in 10 as defined above corresponds to $CH_2$—$R^5$ or CH—$R^5$ of the alcohol 8a or the alkene 9, respectively. Alternatively alcohol 8a may be deoxygenated, e.g., under radical conditions, to provide directly alkane 10. Metallation of 7 affords a carbanion which can be conveniently used to prepare a variety of 3-substituted compounds by quenching with a variety of electrophiles including alkyl halides, electropositive halide derivatives (e.g., $Br_2$ and DAST), dimethyldisulfide, methyl methanethiosulfonate and the like. This list is not limiting and alternative electrophiles would be readily recognized by those skilled in the art.

Scheme 3

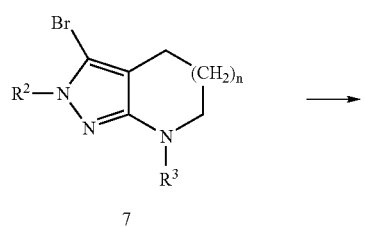

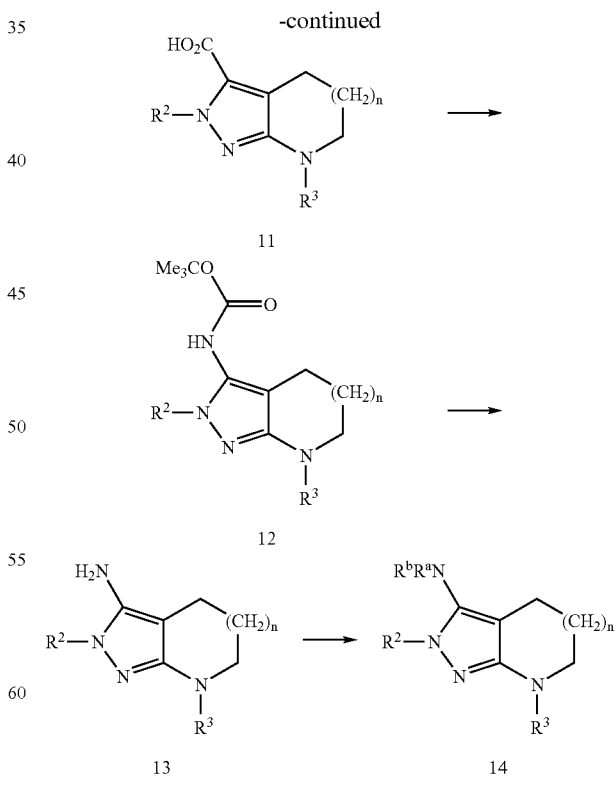

Alternatively, intermediate bromopyrazole 7 is converted into the compounds of Formula I wherein $R^3$ is an $R^aR^bN$— as illustrated in Scheme 3 for Formula I, where $R^2$, $R^3$ $R^a$, $R^b$, and n are as described above. Intermediate bromopyrazole 7 is metallated and reacted with carbon dioxide, or a carbon dioxide equivalent, to provide carboxylic acid 11. Acid 11 is converted to the corresponding amine 13 via an amide rearrangement, such as by the Hofmann, Lossen, or Schmidt reaction, or as illustrated in Scheme 3 by the Curtius rearrangement involving intermediate carbamate 12. Amine 13 is converted into the mono- or disubstituted amine 14 by reductive amination or successive reductive amination, respectively, using an appropriate aldehyde or ketone, and a reducing agent, such as sodium cyanoborohydride, sodium triacetoxyborohydride, and the like. Alternatively, amine 13 is converted into mono- or disubstituted amine 14 via acylation with an appropriate carboxlic acid derivative, such as the corresponding acid chloride, and reduction with an appropriate reducing agent such as diborane, borane-THF complex, and the like. Another alternative conversion of amine 13 to mono- or disubstituted amine 14 is via alkylation with an appropriate alkylating agent, such as methyl iodide, ethyl bromide, and the like, optionally under basic conditions. It is appreciated that each substituent $R^a$ and $R^b$ may be introduced using the same synthetic route described herein, or each substituent may be introduced by a different synthetic route described herein.

Scheme 4

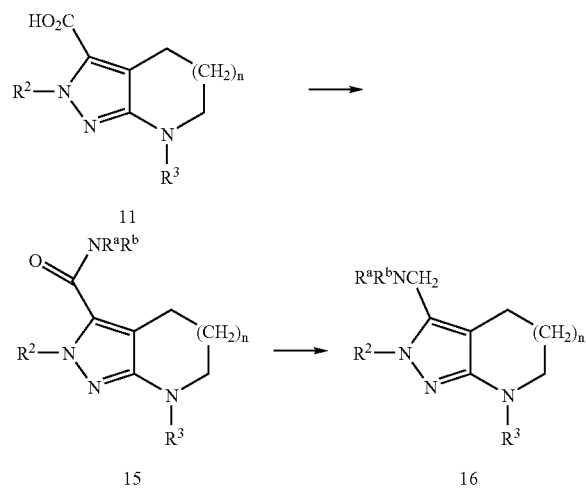

Alternatively, intermediate carboxylic acid 11 is converted into the compounds of Formula I as illustrated in Scheme 4 where $R^2$, $R^3$, $R^a$, $R^b$, and n are as described above. The intermediate carboxylic acid 11 is converted into the corresponding amide 15 and optionally further reduced to amine 16.

Scheme 5

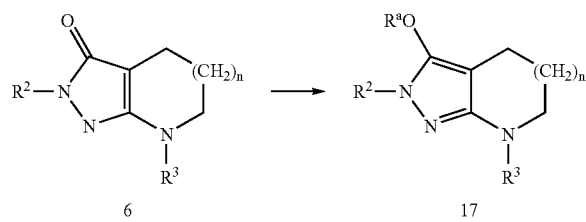

Alternatively, pyrazolinone-fused heterocycle 6 is converted into the compounds of 3-alkoxypyrazole derivatives (17) of Formula I where $R^2$, $R^3$, $R^a$ and n are as described above as illustrated in Scheme 5 for Formula I.

Scheme 6

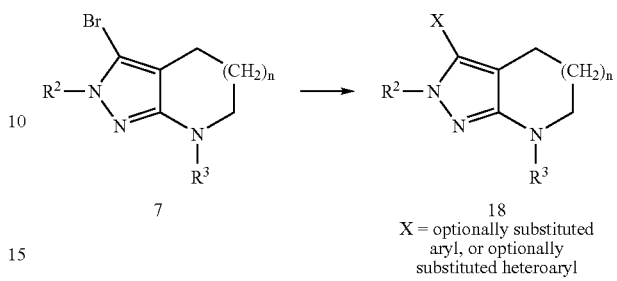

X = optionally substituted aryl, or optionally substituted heteroaryl

Alternatively, intermediate bromopyrazole 7 is converted into the compounds of 3-arylpyrazoles and 3-heteroarylpyrazoles of Formula I where $R^2$, $R^3$ and n are as described above as illustrated in Scheme 6. According to Scheme 6, intermediate bromopyrazole 7 is subjected to a metal-catalyzed aryl coupling reaction to provide an aryl or heteroaryl pyrazole, as illustrated by, for example phenyl pyrazole 18 where X is optionally substituted phenyl.

The synthetic routes illustrated in Schemes 1-6 are suitable for preparing other compounds of Formula I including those compounds where $R^3$, as defined above, is for example naphthyl, pyrimidinyl, or pyridinyl, each of which may be optionally substituted. It is also appreciated that $R^2$ as pertains to the illustrative synthetic sequences of Schemes 1-6 may be a protecting group, as defined above, which may be conveniently removed to provide $R^2$ as hydrogen, or to introduce $R^2$ as alkyl, aryl, acyl, or alkylsulfonyl, as defined above.

Dosage and Administration

The compounds of the present invention may be formulated in a wide variety of oral administration dosage forms and carriers. The pharmaceutically acceptable carriers may be either solid or liquid. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w).

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The term "preparation" or "dosage form" as used herein is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Liquid formulations also are suitable for oral administration include liquid formulation including emulsions, syrups, elixirs, aqueous solutions, aqueous suspensions are also suitable forms for oral administration. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 28 are given to enable those skilled in the art to more clearly understand and to practice the present invention. They should not be considered as limiting the scope of the invention, but merely as being illustrative and representative thereof.

EXAMPLES

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures), but allowance for some experimental error and deviation, including differences in calibration, rounding of numbers, and the like, is contemplated.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature.

Example 1

3-Bromo-7-(2-chloro-4,6-dimethylphenyl)-2-methyl-4,5,6,7-tetrahydro-2H-pyrazolo[3,4-b]pyridine (1-1)

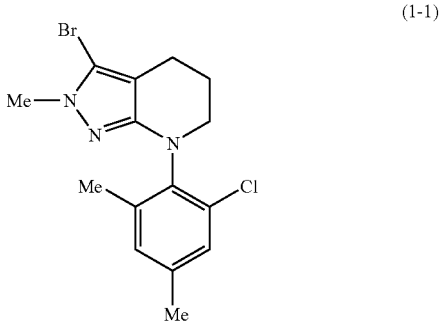

(1-1)

Step 1

5-Chloropentanoic acid (2-chloro-4,6-dimethylphenyl)amide

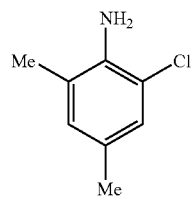

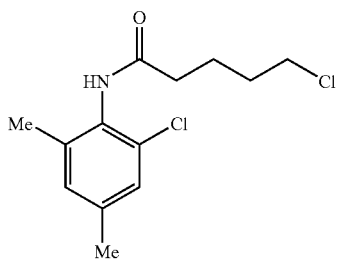

To a solution of 2-chloro-4,6-dimethylaniline (14.7 g) and diisopropylethylamine (18 mL) in 150 mL of THF, was added a solution of 5-chlorovaleryl chloride (12.2 mL) in 75 mL of THF. After the reaction mixture had been allowed to stir at room temperature overnight, it was filtered and the filtrate concentrated on the rotary evaporator. The residue was dissolved in ethyl acetate and washed with 1 M aqueous HCl, saturated aqueous sodium bicarbonate, and brine. The ethyl acetate solution was then dried with magnesium sulfate and concentrated on the rotary evaporator to give a solid which was combined with a 1:1 mixture of hexane and diethyl ether. After this mixture had been stirred for an hour, it was filtered and the collected solids were dried to provide 12.2 g of 5-chloropentanoic acid (2-chloro-4,6-dimethylphenyl) amide: mp 80.6-82.9° C.

Step 2

1-(2-Chloro-4,6-dimethylphenyl)piperidin-2-one

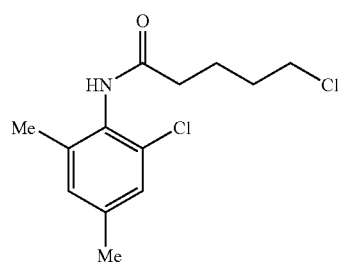

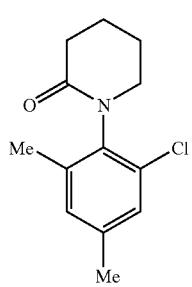

5-Chloropentanoic acid (2-chloro-4,6-dimethylphenyl) amide (21.7 g), potassium t-butoxide (9.34 g), and sodium iodide (1.2 g) were combined in 200 mL t-butanol and the mixture was stirred in a 60° C. oil bath for 3 h. After cooling to room temperature, the reaction mixture was partitioned between ethyl acetate and water. The aqueous phase was washed with additional ethyl acetate. The organic phases were washed with brine, dried with magnesium sulfate, and concentrated to give 18.9 g of 1-(2-chloro-4,6-dimethylphenyl)piperidin-2-one as a solid: mp 107.7-108.7° C.

Step 3

1-(2-Chloro-4,6-dimethylphenyl)piperidine-2-thione

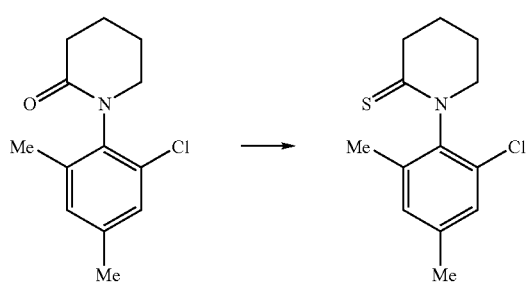

1-(2-Chloro-4,6-dimethylphenyl)piperidin-2-one (18.8 g) and Lawesson's reagent [2,4-bis (4-methoxyphenyl)-1,3-dithia-2,4-diphosphetane-2,4-disulfide] (19.2 g) were combined in 150 mL toluene and the mixture was stirred in an 80° C. oil bath for 3 h. The reaction mixture was then cooled to room temperature and filtered. The filtrate was concentrated on the rotary evaporator and the residue was chromatographed on silica gel, eluting with 9:1 hexane/acetone, to provide 19.4 g of 1-(2-chloro-4,6-dimethylphenyl)piperidine-2-thione: mp 146.8-148.0° C.

Step 4

1-(2-Chloro-4,6-dimethylphenyl)-2-methylsulfanyl-1,4,5,6-tetrahydropyridine-3-carboxylic acid methyl ester

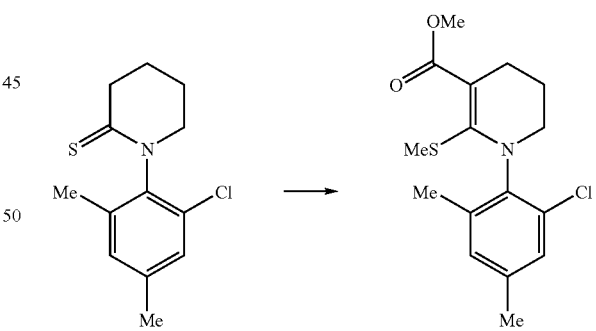

1-(2-Chloro-4,6-dimethylphenyl)piperidine-2-thione (5.11 g), dimethyl carbonate (17.0 mL), sodium hydride (3.7 g of a 60% dispersion in mineral oil), and methanol (0.5 mL) were combined in 100 mL of dioxane and the mixture was stirred in a 120° C. oil bath for 4 h. After the reaction had cooled to room temperature, it was quenched by the addition of aqueous ammonium chloride, diluted with water and washed twice with ethyl acetate. After drying over magnesium sulfate, the ethyl acetate was concentrated and the residue chromatographed on silica gel using an acetone/hexane gradient to provide 5.00 g 1-(2-chloro-4,6-dimethylphenyl)-2-methylsulfanyl-1,4,5,6-tetrahydropyridine-3-carboxylic acid methyl ester: mp 85.3-87.6° C.

Step 5

7-(2-Chloro-4,6-dimethylphenyl)-2-methyl-1,2,4,5,6,7-hexahydropyrazolo-[3,4-b]pyridin-3-one

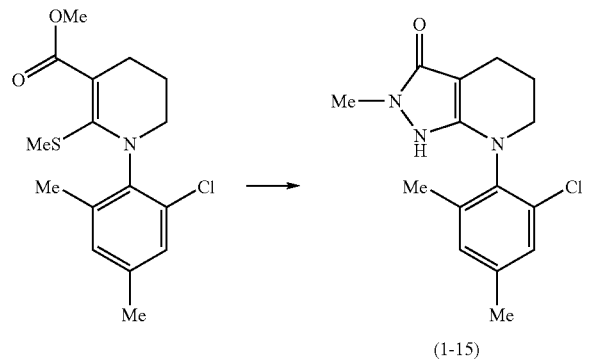

(1-15)

1-(2-Chloro-4,6-dimethylphenyl)-2-methylsulfanyl-1,4,5,6-tetrahydropyridine-3-carboxylic acid methyl ester (4.99 g), methylhydrazine (16.4 mL), p-toluenesulfonic acid monohydrate (2.91 g), and methanol (75 mL) were combined in a glass vessel sealed with a Telfon™ screw cap. The reaction mixture was stirred in a 130° C. oil bath for 24 h, then cooled to room temperature and concentrated on the rotary evaporator. The residue was chromatographed on silica gel using a methanol/dichloromethane gradient to give 3.21 g of 7-(2-chloro-4,6-dimethylphenyl)-2-methyl-1,2,4,5,6,7-hexahydropyrazolo-[3,4-b]pyridin-3-one (1-15): mp 95.9-99.9° C.

Step 6

3-Bromo-7-(2-chloro-4,6-dimethylphenyl)-2-methyl-4,5,6,7-tetrahydro-2H-pyrazolo[3,4-b]pyridine

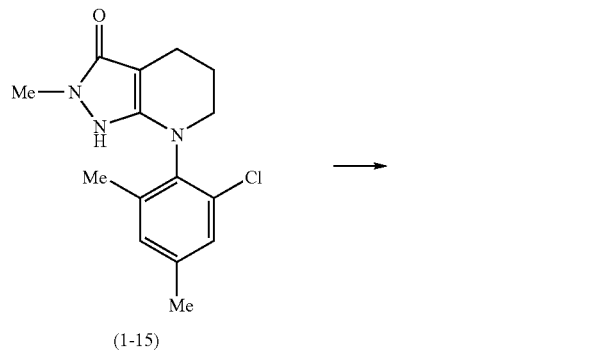

(1-1)

7-(2-Chloro-4,6-dimethylphenyl)-2-methyl-1,2,4,5,6,7-hexahydropyrazolo[3,4-b]pyridin-3-one (3.16 g) and phosphorus oxybromide (15.5 g) were combined and stirred in a 110° C. oil bath for 4 h. After the reaction mixture had cooled to room temperature, it was dissolved in dichloromethane and added to 200 mL of ice/water. This mixture was stirred vigorously for 30 min. The phases were then separated and the aqueous phase was washed with additional dichloromethane. The combined organic phases were washed with aqueous sodium bicarbonate, dried with magnesium sulfate, and concentrated on the rotary evaporator. The residue was chromatographed on silica gel eluting with an acetone/hexane gradient to afford 1.16 g of 3-bromo-7-(2-chloro-4,6-dimethylphenyl)-2-methyl-4,5,6,7-tetrahydro-2H-pyrazolo[3,4-b]pyridine (1-1): mp 106-107° C.

Example 2

3-Bromo-7-(2,4-dichlorophenyl)-2-methyl-4,5,6,7-tetrahydro-2H-pyrazolo[3,4-b]pyridine (1-2)

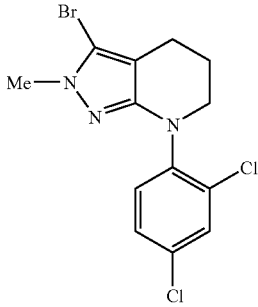

(1-2)

Compound 1-2 was prepared according the procedure described in Example 1, except that 2-chloro-4,6-dimethylaniline was replaced by 2,4-dichloroaniline in step 1, and step 4 was performed as follows:

1-(2,4-Dichlorophenyl)-2-methylsulfanyl-1,4,5,6-tetrahydropyridine-3-carboxylic acid methyl ester

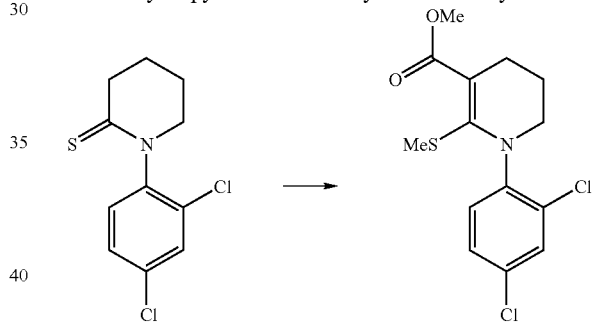

To 39.6 ml of a 3M solution ethylmagnesium bromide in ether was added 100 mL of dry tetrahydrofuran under an atmosphere of nitrogen. Then 16.7 mL of diisopropylamine was added dropwise. The reaction mixture was then heated to 80° C. for 1 h. After cooling to room temperature, the mixture was treated with a solution of 6.19 g of 1-(2,4-dichlorophenyl)piperidine-2-thione in 50 mL of dry tetrahydrofuran, heated to 80° C. for 30 min, and cooled again to room temperature. Then the mixture was treated dropwise with 10.0 mL of dimethylcarbonate and heated to 80° C. for 26 h. After cooling to room temperature, 100 g of ice was added along with 150 mL of 1.2M HCl. The mixture was extracted three times with 100 mL portions of dichloromethane. The combined organic extracts were washed with 100 mL of brine, dried over magnesium sulfate, concentrated, and then kept under high vacuum at 50° C. to remove the higher boiling volatile materials. The residue was purified by flash silica gel chromatography using 7% acetone/hexane as solvent yielding 5.25 g of 1-(2,4-dichlorophenyl)-2-methylsulfanyl-1,4,5,6-tetrahydropyridine-3-carboxylic acid methyl ester as a yellow solid: mp 83-86° C.

Compounds 1-3 to 1-11

Compounds 1-3 and 1-12 were prepared according to Example 1 except that 2,4-dichloroaniline was replaced by 2,4,6-trimethylaniline and 3-amino-2-dimethylamino-4-methyl pyridine, respectively.

Compound 1-4 was prepared according to the procedure described in Example 1, except in step 1 2-chloro-4,6-dimethylaniline was replaced by 2,4,6-trimethylaniline and 5-chlorovaleryl chloride was replaced by 6-chlorocaproyl chloride.

Compound 1-5 was prepared according to the procedure described in Example 1, except in step 1 2-chloro-4,6-dimethylaniline was replaced with 2,4,6-trimethylaniline and in step 5 methyl hydrazine was replaced with hydrazine.

Compounds 1-6, 1-7, 1-8 and 1-12 were prepared according to Example 2 except that 2,4-dichloroaniline was replaced by 1,3,5-trichloroaniline, 4-methoxy-2-methyl-aniline, 4-chloroaniline and 3-amino-2-dimethylamino-4-methylpyridine respectively.

Compounds 1-9, 1-10, and 1-11 were prepared according to step 6 of Example 1 except POBr₃ is replaced with POCl₃ and 1-15 was replaced with 1-16, 1-17 and 1-18, respectively.

Compound 1-13 was prepared in step 5 of Example 2.

Example 3

3-Methoxy-7-(4-methoxy-2-methyl-phenyl)-2-methyl-4,5,6,7-tetrahydro-2H-pyrazolo[3,4-b]pyridine (1-14) and 3-methoxy-7-(4-methoxy-2-methyl-phenyl)-1,2-dimethyl-4,5,6,7-tetrahydro-2H-pyrazolo[3,4-b]pyridine sulfuric acid monomethyl ester

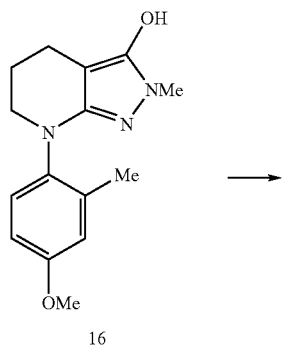

16

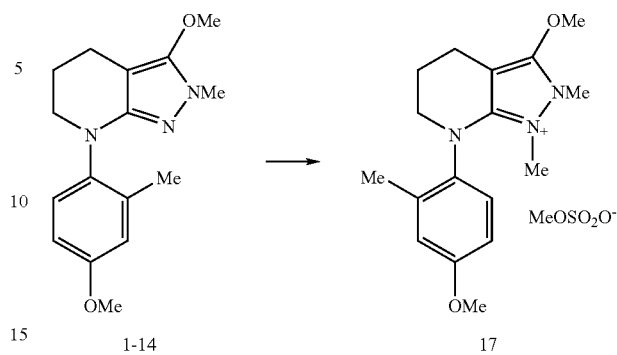

1-14                                17

7-(4-methoxy-2-methyl-phenyl)-2-methyl-4,5,6,7-tetrahydro-2H-pyrazolo[3,4-b]pyridin-3-ol (16) was isolated from step 5 of the preparation of 1-7.

A mixture of 7-(4-methoxy-2-methyl-phenyl)-2-methyl-4,5,6,7-tetrahydro-2H-pyrazolo[3,4-b]pyridin-3-ol (16; 0.150 g, 0.55 mmole) and dimethyl sulfate (0.40 g, 3.2 mmole) under a nitrogen atmosphere was heated at 100° C. for 1 h. The reaction mixture was cooled to room temperature, diluted with ethyl acetate, washed sequentially with saturated sodium bicarbonate and brine, dried over magnesium sulfate, and evaporated to dryness. The residue was purified by preparative thin layer chromatography (methanol/dichloromethane: 3/97) which afforded 0.010 g (6% theory) of 1-14 as light brown viscous oil: ms $(M+H)^+=288$. The predominant product isolated from the reaction mixture was) of 3-methoxy-7-(4-methoxy-2-methyl-phenyl)-1,2-dimethyl-4,5,6,7-tetrahydro-2H-pyrazolo[3,4,-b]pyridine sulfuric acid monomethyl ester (17; 0.058 g; 25% theory) as a colorless oil: ms $(M)^+=302$.

TABLE 1

| Cpd # | Structure | Name | mp (° C.) | MH+ observed (predicted) |
|---|---|---|---|---|
| 1-1 | 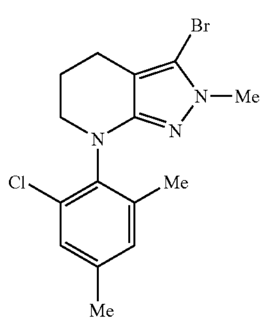 | 3-Bromo-7-(2-chloro-4,6-dimethylphenyl)-2-methyl-4,5,6,7-tetrahydro-2H-pyrazolo[3,4-b]pyridine | 106-107 | 354 (354) |

TABLE 1-continued
| Cpd # | Structure | Name | mp (° C.) | MH+ observed (predicted) |
|---|---|---|---|---|
| 1-2 | 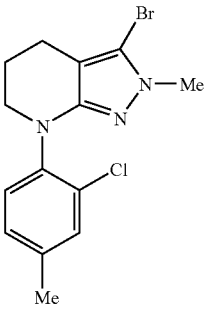 | 3-Bromo-7-(2,4-dichloro-phenyl)-2-methyl-4,5,6,7-tetrahydro-2H-pyrazolo [3,4-b]pyridine | | 360 (360) |
| 1-3 | 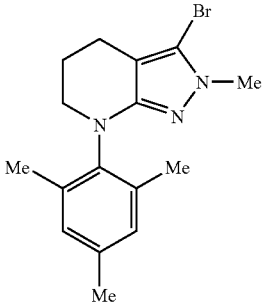 | 3-Bromo-2-methyl-7-(2,4,6-trimethyl-phenyl)-4,5,6,7-tetrahydro-2H-pyrazolo[3,4-b]pyridine | 94.6-97.9 | 334 (334) |
| 1-4 | 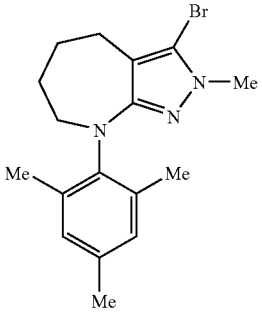 | 3-Bromo-2-methyl-8-(2,4,6-trimethyl-phenyl)-2,4,5,6,7,8-hexahydro-1,2,8-triaza-azulene | | 348 (348) |
| 1-5 | 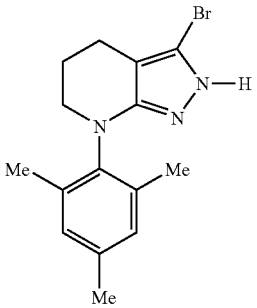 | 3-Bromo-7-(2,4,6-trimethyl-phenyl)-4,5,6,7-tetrahydro-2H-pyrazolo [3,4-b]pyridine | | 320 (320) |

TABLE 1-continued

| Cpd # | Structure | Name | mp (° C.) | MH+ observed (predicted) |
|---|---|---|---|---|
| 1-6 | 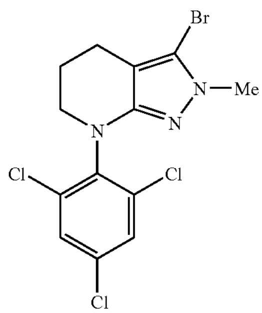 | 3-Bromo-2-methyl-7-(2,4,6-trichloro-phenyl)-4,5,6,7-tetrahydro-2H-pyrazolo[3,4-b]pyridine | 100-101 | 394 (394) |
| 1-7 | 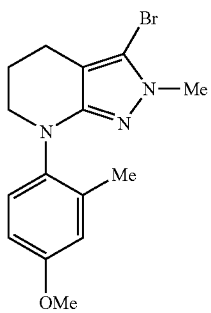 | 3-Bromo-2-methyl-7-(4-methoxy 2-methyl-phenyl)-4,5,6,7-tetrahydro-2H-pyrazolo[3,4-b]pyridine | 101.7-104.1 | 336 (336) |
| 1-8 | 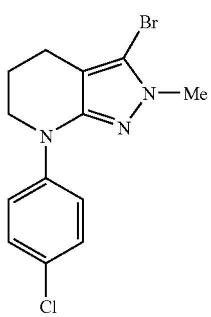 | 3-Bromo-2-methyl-7-(4-chloro-phenyl)-4,5,6,7-tetrahydro-2H-pyrazolo[3,4-b]pyridine | 113.8-114.9 | 326 (326) |
| 1-9 | 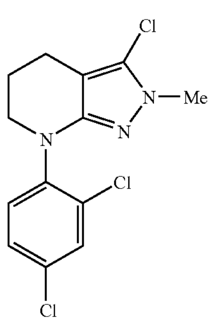 | 3-chloro-7-(2,4-dichloro-phenyl)-2-methyl-4,5,6,7-tetrahydro-2H-pyrazolo [3,4-b] pyridine | 94.5-95.5 | 316 (316) |

TABLE 1-continued

| Cpd # | Structure | Name | mp (° C.) | MH+ observed (predicted) |
|---|---|---|---|---|
| 1-10 | 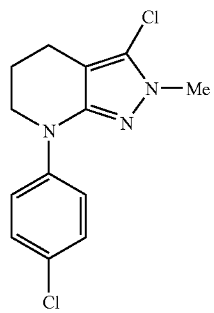 | 3-chloro-7-(4-chloro-phenyl)-2-methyl-4,5,6,7-tetrahydro-2H-pyrazolo [3,4-b]pyridine | 96.5-97.5 | 282 (282) |
| 1-11 | 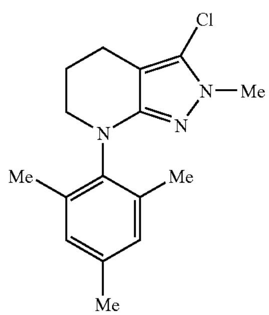 | 3-chloro-7-(2,4,6-trimethyl-phenyl)-2-methyl-4,5,6,7-tetrahydro-2H-pyrazolo[3,4-b]pyridine | 83-86 | 290 (290) |
| 1-12 | 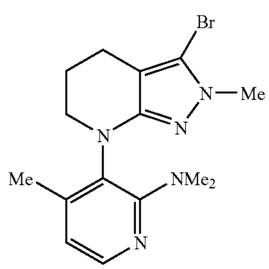 | [3-(3-Bromo-2-methyl-2,4,5,6-tetrahydro-pyrazolo[3,4-b]pyridin-7-yl)-4-methyl-pyridin-2-yl]-dimethyl-amine | | 350 (350) |
| 1-13 | 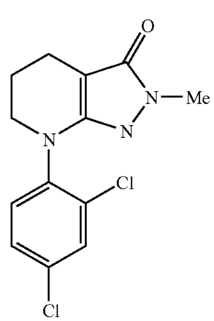 | 3-hydroxy-7-(2,4-dichloro-phenyl)-2-methyl-4,5,6,7-tetrahydro-2H-pyrazolo [3,4-b]pyridine | 98-100.5 | 298 (298) |
| 1-14 | 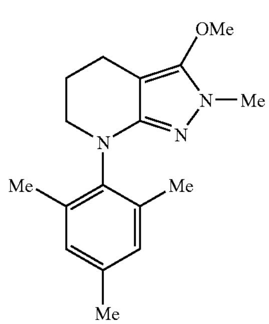 | 3-Methoxy-2-methyl-7-(2,4,6-trimethyl-phenyl)-4,5,6,7-tetrahydro-2H-pyrazolo[3,4-b]pyridine | | 288 (288) |

TABLE 1-continued

| Cpd # | Structure | Name | mp (° C.) | MH+ observed (predicted) |
|---|---|---|---|---|
| 1-15 | 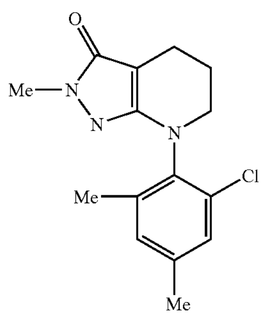 | 7-(2-Chloro-4,6-dimethyl-phenyl)-2-methyl-1,2,4,5,6,7-hexahydro-pyrazolo[3,4-b]pyridin-3-one | 103-109 | 292 (292) |
| 1-16 | 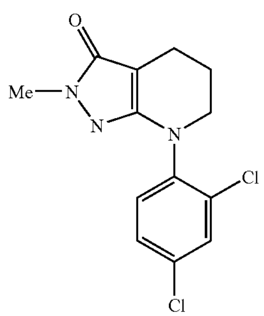 | 7-(2,4-dichloro-phenyl)-2-methyl-1,2,4,5,6,7-hexahydro-pyrazolo[3,4-b]pyridin-3-one | 98-100.5 | 298 (298) |
| 1-17 | 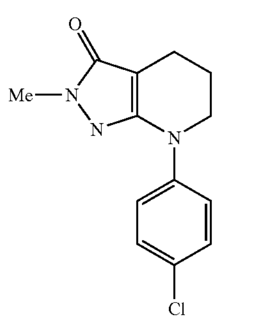 | 7-(4-chloro-phenyl)-2-methyl-1,2,4,5,6,7-hexahydro-pyrazolo[3,4-b]pyridin-3-one | 219.5-221.6 | 264 (264) |
| 1-18 | 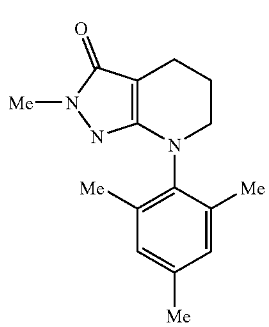 | 2-methyl-7-(2,4,6-trimethylphenyl)1,2,4,5,6,7-hexahydro-pyrazolo[3,4-b]pyridin-3-one | | 272 (272) |

Example 4

4-[7-(2-Chloro-4,6-dimethylphenyl)-2-methyl-4,5,6,7-tetrahydro-2H-pyrazolo-[3,4-b]pyridin-3-yl]heptan-4-ol (2-1)

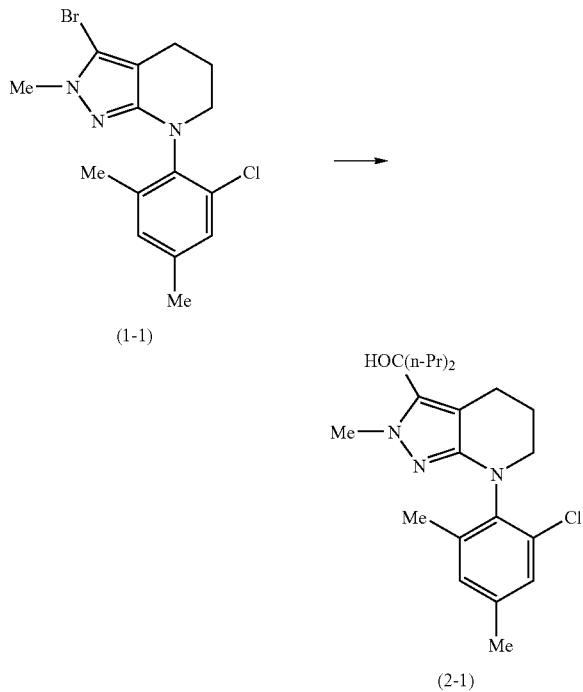

3-Bromo-7-(2-chloro-4,6-dimethylphenyl)-2-methyl-4,5,6,7-tetrahydro-2H-pyrazolo[3,4-b]pyridine (1-1; 122 mg) and a crystal of 1,10-phenanthroline were dissolved in 3 mL of dry tetrahydrofuran and the solution was chilled to −78° C. under an atmosphere of argon. To the cooled solution was added n-butyllithium (2.0 M in cyclohexane) until the dark color of the organolithium/phenanthroline complex persisted. An additional 0.17 mL of the butyllithium solution then was added. After 10 m, a solution of 4-heptanone (42.6 mg) in 1 mL tetrahydrofuran was added via syringe. The reaction mixture was allowed to stir at −78° C. for 15 m, then was allowed to warm to 0° C. After quenching with aqueous ammonium chloride, the reaction mixture was partitioned between ethyl acetate and brine. The ethyl acetate was dried with magnesium sulfate and concentrated on the rotary evaporator. The residue was chromatographed on silica gel eluting with 9:1 hexane/acetone to afford 76.0 mg of 4-[7-(2-chloro-4,6-dimethylphenyl)-2-methyl-4,5,6,7-tetrahydro-2H-pyrazolo-[3,4-b]pyridin-3-yl]heptan-4-ol (2-1) which was recrystallized from hexane: mp 129-130° C.

Compounds 2-2 to 2-16

Compound 2-2 was prepared according to the procedure described in Example 4, except that the compound 1-1 was replaced with compound 1-3.

Compound 2-3 was prepared according to the procedure described in Example 4, except that 4-heptanone was replaced with 1-(thien-2-yl)butanone and compound 1-1 was replaced with compound 1-3.

Compound 2-4 was prepared according to the procedure described in Example 4, except that compound 1-1 was replaced with compound 1-4.

Compound 2-5 was prepared according to the procedure described in Example 4, except that compound 1-1 was replaced with compound 1-2.

Compound 2-6 was prepared according to the procedure described in Example 4, except that 4-heptanone was replaced with 1,3-bis-methoxypropan-2-one and compound 1-1 was replaced with compound 1-3.

Compound 2-7 was prepared according to the procedure described in Example 4, except that 4-heptanone was replaced with 1,4-bis-methoxybutan-2-one and compound 1-1 was replaced with compound 1-3.

Compound 2-8 was prepared according to the procedure described in Example 4, except that 4-heptanone was replaced with 1-(thiazol-2-yl)butan-2-one and compound 1-1 was replaced with compound 1-3.

Compound 2-9 was prepared according to the procedure described in Example 4, except that 4-heptanone was replaced with 2-furancarboxaldehyde and compound 1-1 was replaced with compound 1-3.

Compound 2-10 was prepared according to the procedure described in Example 4, except that 4-heptanone was replaced with propanal and compound 1-1 was replaced with compound 1-3.

Compound 2-11 was prepared according to the procedure described in Example 4, except that 4-heptanone was replaced with 1-(1-ethylimidazol-2-yl)butan-2-one and compound 1-1 was replaced with compound 1-3.

Compound 2-12 was prepared according to the procedure described in Example 4, except that 4-heptanone was replaced with tetrahydropyran-4-one and compound 1-1 was replaced with compound 1-3.

Compound 2-13 was prepared according to the procedure described in Example 4, except that 4-heptanone was replaced with water.

Compound 2-14 and 2-15 were prepared according to the procedure described in Example 4, except that 4-heptanone was replaced with acetaldehyde and compound 1-1 was replaced with compounds 1-2 and 1-3, respectively.

Compound 2-16 was prepared according to the procedure described in Example 4, except that 4-heptanone was replaced with acetone and the compound 1-1 was replaced with compound 1-3.

Example 5

7-(2,4-Dichloro-phenyl)-2,3-dimethyl-4,5,6,7-tetrahydro-2H-pyrazolo[3,4-b]pyridine (2-17)

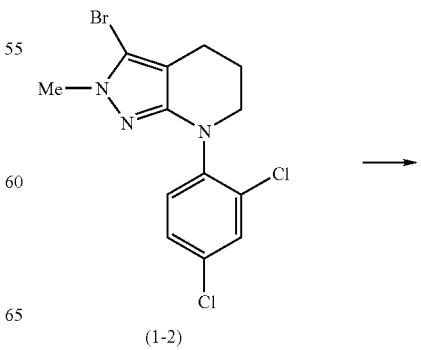

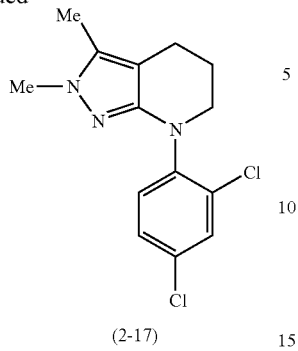

(2-17)

A solution of 3-bromo-7-(2,4-dichloro-phenyl)-2-methyl-4,5,6,7-tetrahydro-2H-pyrazolo[3,4-b]pyridine (1-2; 0.100 g, 0.277 mmol) in 2 mL of dry THF was cooled to –78° C. in a dry ice-acetone bath under an argon atmosphere and treated with 0.21 mL of 1.6 M n-butyllithium in hexane. After 10 m the mixture was treated with iodomethane (0.21 mL, 0.047 g, 0.33 mmol) and stirred at –78° C. for 1 h and allowed to come to room temperature overnight. The reaction mixture was quenched with 40 mL of saturated ammonium chloride and extracted twice with 25 mL portions of ethyl acetate. The combined the extracts were washed with brine, dried over magnesium sulfate, and evaporated to dryness to yield 79 mg of crude product. Purification by preparative TLC using ethyl acetate/toluene (1:9) afforded 19 mg of 7-(2,4-dichloro-phenyl)-2,3-dimethyl-4,5,6,7-tetrahydro-2H-pyrazolo[3,4-b]pyridine (2-17; 23% theory) as a pink solid: mp 66.6-76.6° C.

Compound 2-18 was prepared according to Example 5 except compound 1-1 was replaced with compound 1-3.

Compound 2-19 was prepared according to Example 5 except iodomethane was replaced with N-fluorobenzenesulfonimide (D. F. Duerr, et al., *J. Org. Chem.* 1988 53:2120) and compound 1-1 was replaced with compound 1-3. The procedure afforded 2-19 in 13% yield as a brown solid: (M+H)+=274.

Example 6

2-Methyl-3-methylsulfanyl-7-(2,4,6-trimethyl-phenyl)-4,5,6,7-tetrahydro-2H-pyrazolo[3,4-b]pyridine (2-20) and 7-(2,4,6-trimethyl-phenyl)-3-methanesulfonyl-2-methyl-4,5,6,7-tetrahydro-2H-pyrazolo[3,4-b]pyridine (2-21)

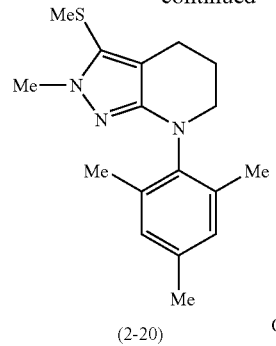

(1-2)

→

(2-20)

↓

(2-21)

Step 1

2-Methyl-3-methylsulfanyl-7-(2,4,6-trimethyl-phenyl)-4,5,6,7-tetrahydro-2H-pyrazolo[3,4-b]pyridine (2-20) was prepared according to Example 5 except iodomethane was replaced with methyl methanethiosulfonate (A. I. Meyers and M. A. Sturgess, *Tetrahedron Lett.* 1988 29:5339) as the electrophile and compound 1-1 was replaced with compound 1-3 to afford 2-20 as a white solid (48% theory; mp=90.3-91.7° C.).

Step 2

A solution of 2-20 (0.116 g, 0.38 mmol) in 8 mL of acetone was treated with a solution of OXONE (potassium peroxymonosulfate; 0.710 g, 1.15 mmol) dissolved in 2 mL of water which afforded a heterogeneous yellow mixture. The reaction mixture was stirred at room temperature for 18 h, adjusted to pH 14 with 1M sodium hydroxide, extracted twice with 20 mL of ethyl acetate and once with 10 mL of dichloromethane. The combined extracts were washed with brine, dried over magnesium sulfate, and evaporated to dryness. The residue was purified by flash silica gel chromatography eluting with dichloromethane to afford 21 mg of 7-(2,4-dichloro-phenyl)-3-methanesulfonyl-2-methyl-4,5,6,7-tetrahydro-2H-pyrazolo[3,4-b]pyridine (2-21) as a white solid (16% theory): mp 181.6-183° C.

Compound 2-22 was prepared according to Example 5 except iodomethane was replaced with tosyl cyanide (K. J. Rutan, et al. *J. Org. Chem* 1995 60:2948) to afford 2-22 in 20% yield: mp. 128.5-136.6° C.

Compound 2-23 was prepared as in Example 5 except iodomethane was replaced by N-methoxy-N-methyl-actamide and compound 1-1 was replaced with compound 1-3 to afford 2-23 in 5% yield as a viscous brown oil.

Compound 2-24 was prepared as in Example 5 except iodomethane was replaced by N,N-dimethylformamide and compound 1-1 was replaced with compound 1-3 to afford 2-24 as a brown solid (21% theory): mp 120.5-123.5° C.

TABLE 2

| Cpd # | Structure | Name | mp (° C.) | MH+ observed (predicted) |
|---|---|---|---|---|
| 2-1 | 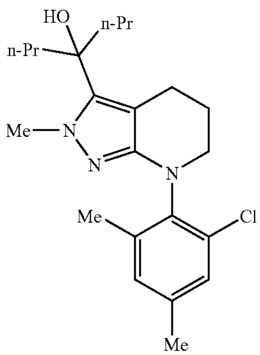 | 4-[7-(2-Chloro-4,6-dimethylphenyl)-2-methyl-4,5,6,7-tetrahydro-2H-pyrazolo[3,4-b]pyridin-3-yl]heptan-4-ol | 129-130 | 390 (390) |
| 2-2 | 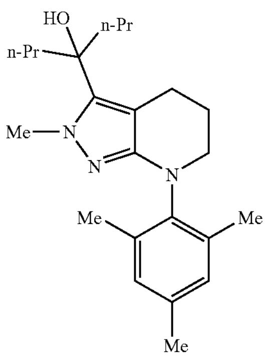 | 4-[2-Methyl-7-(2,4,6-trimethylphenyl)-4,5,6,7-tetrahydro-2H-pyrazolo[3,4-b]pyridin-3-yl] heptan-4-ol | 126-127.9 | 370 (370) |
| 2-3 | 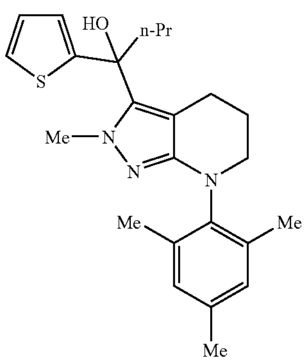 | 1-[2-Methyl-7-(2,4,6-trimethylphenyl)-4,5,6,7-tetrahydro-2H-pyrazolo[3,4-b]pyridin-3-yl]-1-thiophen-2-ylbutan-1-ol | 175.9-178.4 | 410 (410) |
| 2-4 | 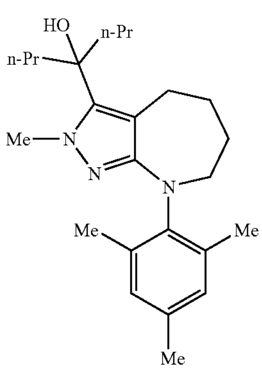 | 4-[2-Methyl-8-(2,4,6-trimethylphenyl)-2,4,5,6,7,8-hexahydro-1,2,8-triazaazulen-3-yl]heptan-4-ol | 87-91.1 | 384 (384) |

TABLE 2-continued

| Cpd # | Structure | Name | mp (° C.) | MH+ observed (predicted) |
|---|---|---|---|---|
| 2-5 | 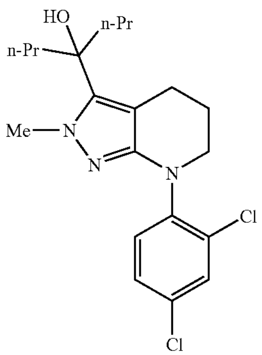 | 4-[7-(2,4-Dichlorophenyl)-2-methyl-4,5,6,7-tetrahydro-2H-pyrazolo [3,4-b]pyridin-3-yl]heptan-4-ol | 121.4-122.6 | 396 (396) |
| 2-6 | 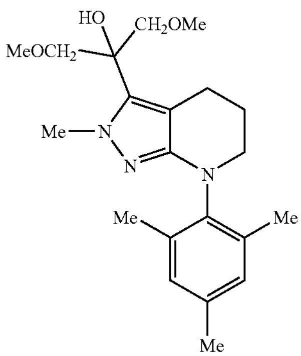 | 1,3-Dimethoxy-2-[2-methyl-7-(2,4,6-trimethylphenyl)-4,5,6,7-tetrahydro-2H-pyrazolo[3,4-b]pyridin-3-yl]propan-2-ol | 120.3-121.8 | 374 (374) |
| 2-7 | 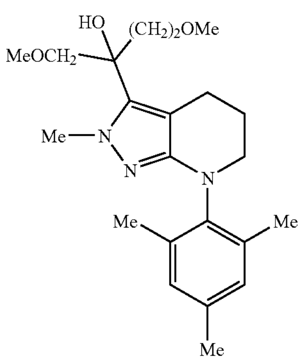 | 1,4-Dimethoxy-2-[2-methyl-7-(2,4,6-trimethylphenyl)-4,5,6,7-tetrahydro-2H-pyrazolo[3,4-b]pyridin-3-yl]butan-2-ol | 107.9-110.9 | 388 (388) |
| 2-8 | 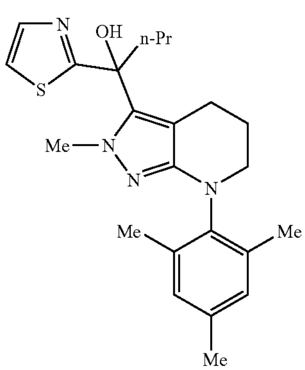 | 1-[2-Methyl-7-(2,4,6-trimethylphenyl)-4,5,6,7-tetrahydro-2H-pyrazolo[3,4-b]pyridin-3-yl]-1-thiazol-2-ylbutan-1-ol | 160.1-165.6 | 411 (411) |

TABLE 2-continued

| Cpd # | Structure | Name | mp (° C.) | MH+ observed (predicted) |
|---|---|---|---|---|
| 2-9 | 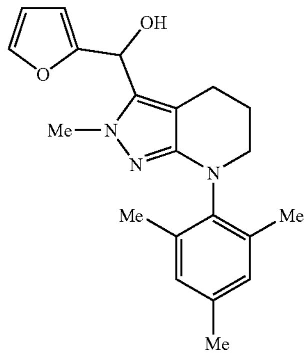 | Furan-2-yl[2-methyl-7-(2,4,6-trimethyl-phenyl)-4,5,6,7-tetrahydro-2H-pyrazolo[3,4-b]pyridin-3-yl]methanol | 163.1-174.4 | 352 (352) |
| 2-10 | 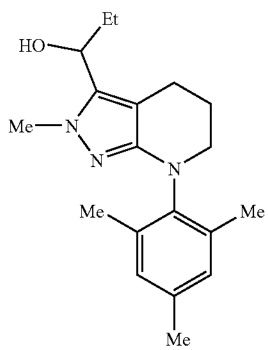 | 1-[2-Methyl-7-(2,4,6-trimethylphenyl)-4,5,6,7-tetrahydro-2H-pyrazolo[3,4-b]pyridin-3-yl]propan-1-ol | 179.4-180.9 | 314 (314) |
| 2-11 | 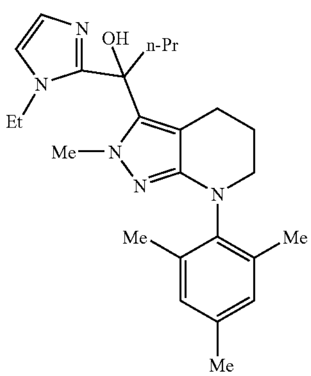 | 1-(1-Ethyl-1H-imidazol-2-yl)-1-[2-methyl-7-(2,4,6-trimethylphenyl)-4,5,6,7-tetrahydro-2H-pyrazolo[3,4-b]pyridin-3-yl]butan-1-ol | 94.9-100.9 | 422 (422) |
| 2-12 | 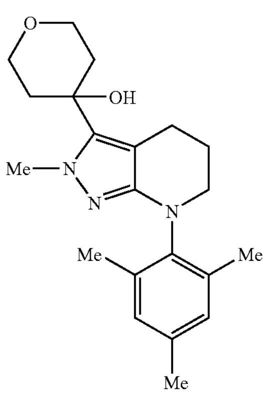 | 4-[2-Methyl-7-(2,4,6-trimethylphenyl)-4,5,6,7-tetrahydro-2H-pyrazolo[3,4-b]pyridin-3-yl]tetrahydropyran-4-ol | 193-195.1 | 356 (356) |

TABLE 2-continued

| Cpd # | Structure | Name | mp (° C.) | MH+ observed (predicted) |
|---|---|---|---|---|
| 2-13 | 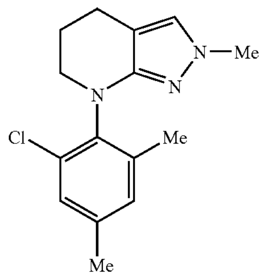 | 7-(2-Chloro-4,6-dimethylphenyl)-2-methyl-4,5,6,7-tetrahydro-2H-pyrazolo[3,4-b]pyridine | 97-98 | 276 (276) |
| 2-14 | 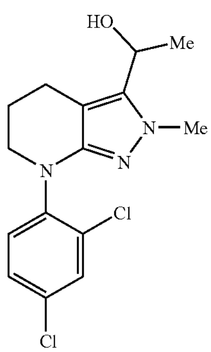 | 1-[7-(2,4-Dichloro-phenyl)-2-methyl-4,5,6,7-tetrahydro-2H-pyrazolo[3,4-b] pyridin-3-yl]-ethanol | 56.7-64.0 | 326 (326) |
| 2-15 | 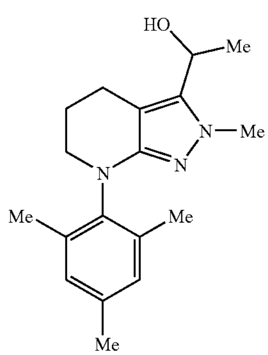 | 1-[7-(2,4,6-trimethyl-phenyl)-2-methyl-4,5,6,7-tetrahydro-2H-pyrazolo[3,4-b]pyridin-3-yl]-ethanol | 178-179.6 | 300 (300) |
| 2-16 | 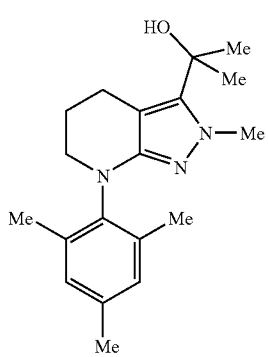 | 2-[7-(2,4,6-trimethyl-phenyl)-2-methyl-4,5,6,7-tetrahydro-2H-pyrazolo[3,4-b]pyridin-3-yl]-propan-2-ol | 158.9-161.6 | 314 (314) |

TABLE 2-continued

| Cpd # | Structure | Name | mp (° C.) | MH+ observed (predicted) |
|---|---|---|---|---|
| 2-17 | 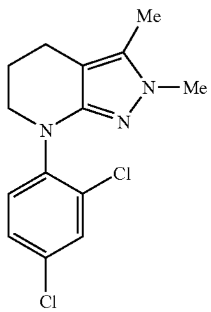 | 7-(2,4-Dichloro-phenyl)-2,3-dimethyl-4,5,6,7-tetrahydro-2H-pyrazolo[3,4-b]pyridine | 66.6-76.6 | 296 (296) |
| 2-18 | 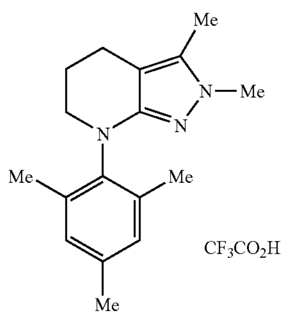 | 2,3-Dimethyl-7-(2,4,6-trimethyl-phenyl)-4,5,6,7-tetrahydro-2H-pyrazolo [3,4-b]pyridine; compound with trifluoro-acetic acid | | 270 (270) |
| 2-19 | 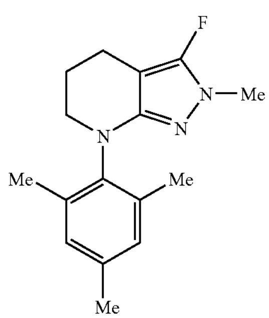 | 3-Fluoro-2-methyl-7-(2,4,6-trimethyl-phenyl)-4,5,6,7-tetrahydro-2H-pyrazolo[3,4-b]pyridine | | 274 (274) |
| 2-20 | 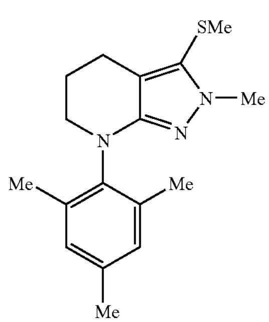 | 2-Methyl-3-methylsulfanyl-7-(2,4,6-trimethyl-phenyl)-4,5,6,7-tetrahydro-2H-pyrazolo[3,4-b]pyridine | 90.3-91.7 | 302 (302) |

TABLE 2-continued

| Cpd # | Structure | Name | mp (° C.) | MH+ observed (predicted) |
|---|---|---|---|---|
| 2-21 | 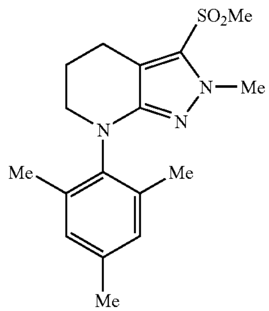 | 3-Methanesulfonyl-2-methyl-7-(2,4,6-trimethyl-phenyl)-4,5,6,7-tetrahydro-2H-pyrazolo[3,4-b]pyridine | 181.6-183.0 | 334 (334) |
| 2-22 | 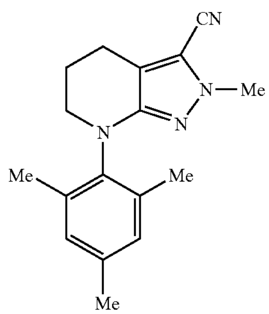 | 2-Methyl-7-(2,4,6-trimethyl-phenyl)-4,5,6,7-tetrahydro-2H-pyrazolo[3,4-b] pyridine-3-carbonitrile | 128.5-136.6 | 281 (281) |
| 2-23 | 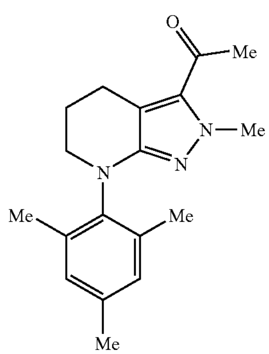 | 1-[2-Methyl-7-(2,4,6-trimethyl-phenyl)-4,5,6,7-tetrahydro-2H-pyrazolo[3,4-b]pyridin-3-yl]-ethanone | | 298 (298) |
| 2-24 | 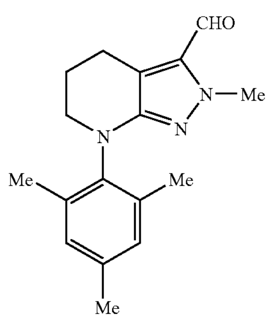 | 2-Methyl-7-(2,4,6-trimethyl-phenyl)-4,5,6,7-tetrahydro-2H-pyrazolo[3,4-b] pyridine-3-carbaldehyde | 120.5-123.5 | 284 |

Example 7

7-(2-Chloro-4,6-dimethylphenyl)-2-methyl-3-(1-propylbut-1-enyl)-4,5,6,7-tetrahydro-2H-pyrazolo[3,4-b]pyridine (3-1)

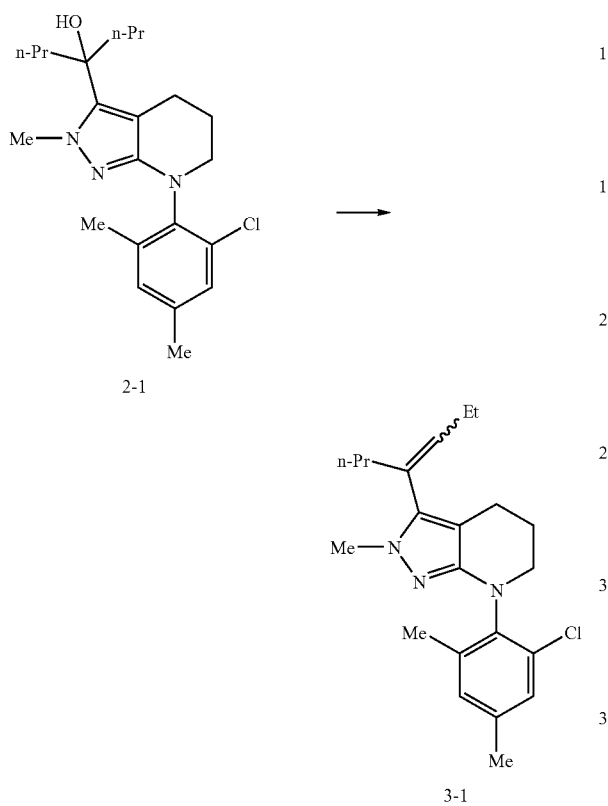

2-1

3-1

4-[7-(2-Chloro-4,6-dimethylphenyl)-2-methyl-4,5,6,7-tetrahydro-2H-pyrazolo[3,4-b]pyridin-3-yl]heptan-4-ol (2-1; 594 mg) and p-toluenesulfonic acid monohydrate (74 mg) were combined in 13 mL toluene and the stirred mixture was heated to 110° C. for 11 h. The reaction mixture was then cooled to room temperature and partitioned between ethyl acetate and aqueous sodium bicarbonate. The aqueous phase was washed with additional ethyl acetate. The combined ethyl acetate fractions were washed with brine, dried with magnesium sulfate, and concentrated. The residue was chromatographed on silica gel eluting with an acetone/hexane gradient to provide 461 mg of compound 3-1 which was recrystallized from hexane: mp 86.7-88.2° C.

Compounds 3-2 to 3-6

Compound 3-2 was prepared according to the procedure described in Example 7, except that compound 2-1 was replaced with compound 2-2.

Compound 3-3 was prepared according to the procedure described in Example 7, except that compound 2-1 was replaced with compound 2-3.

Compound 3-4 was prepared according to the procedure described in Example 7, except that compound 2-1 was replaced by the compound 2-4.

Compound 3-5 was prepared according to the procedure described in Example 7, except that compound 2-1 was replaced by compound 2-5.

Compound 3-6 was prepared according to the procedure described in Example 7, except that compound 2-1 was replaced by the compound 2-8.

Compound 3-7 was prepared according to the procedure described in Example 7, except that compound 2-1 was replaced by compound 2-14.

Compound 3-8 was prepared according to the procedure described in Example 7, except that compound 2-1 was replaced by compound 2-15.

Compound 3-9 was prepared according to the procedure described in Example 6a, except that compound 2-1 was replaced by compound 2-16.

Example 8

7-(2,4-Dichloro-phenyl)-3-ethynyl-2-methyl-4,5,6,7-tetrahydro-2H-lpyrazolo[3,4-b]pyridine (3-10)

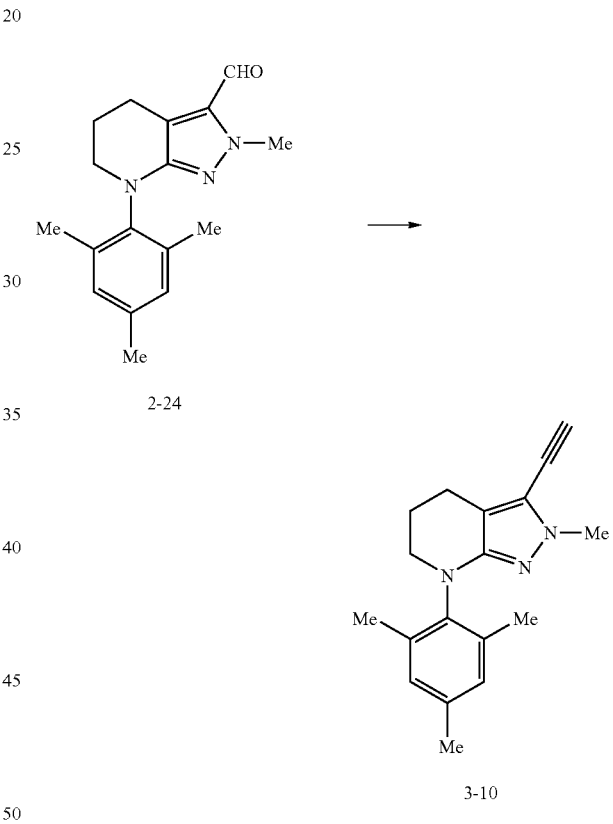

2-24

3-10

A solution of 7-(2,4-dichloro-phenyl)-2-methyl-4,5,6,7-tetrahydro-2H-pyrazolo[3,4-b]pyridine-3-carbaldehyde (2-24; 0.030 g, 0.097 mmol) in methanol (3 mL) was treated with dimethyl-1-diazo-2-oxopropylphosphonate (0.022 g, 0.12 mmol) [prepared according to P. Callant, et al., *Syn. Commun* 1984 14(2):155] and the mixture was cooled in an ice bath under a nitrogen atmosphere. To this solution was added potassium carbonate (0.027 g, 0.19 mmol) giving a yellow mixture. The ice bath was removed and the mixture was stirred at room temperature for 7 h. The solvent was evaporated and the residue taken up in ethyl acetate, washed sequentially with saturated sodium bicarbonate and brine, dried over magnesium sulfate, and evaporated to dryness. The residue was purified by silica gel flash chromatography eluting with ethyl acetate/hexane (5:95) yielding 0.013 g (43% theory) of 3-10: mp 105-107.5° C.

TABLE 3

| Cpd # | Structure | Name | mp (°C.) | H+ observed (predicted) |
|---|---|---|---|---|
| 3-1 | 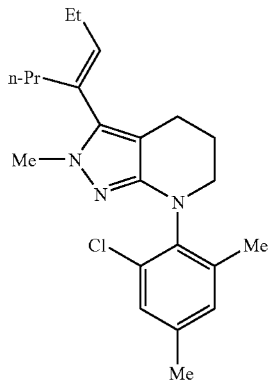 | 7-(2-Chloro-4,6-dimethylphenyl)-2-methyl-3-(1-propylbut-1-enyl)-4,5,6,7-tetrahydro-2H-pyrazolo[3,4-b]pyridine | 86.7-88.2 | 372 (372) |
| 3-2 | 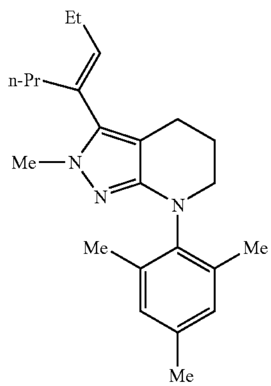 | 2-Methyl-3-(1-propylbut-1-enyl)-7-(2,4,6-trimethylphenyl)-4,5,6,7-tetrahydro-2H-pyrazolo[3,4-b]pyridine | 101.6-102.6 | 352 (352) |
| 3-3 | 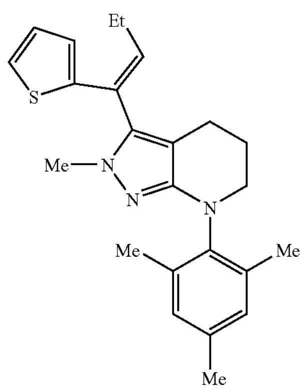 | 2-Methyl-3-(1-thiophen-2-ylbut-1-enyl)-7-(2,4,6-trimethylphenyl)-4,5,6,7-tetrahydro-2H-pyrazolo[3,4-b]pyridine | oil | 392 (392) |
| 3-4 | 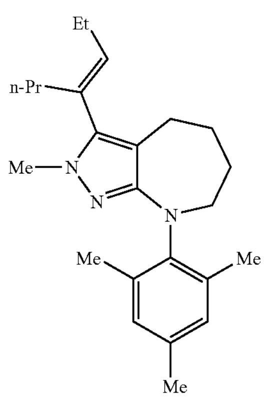 | 2-Methyl-3-(1-propylbut-1-enyl)-8-(2,4,6-trimethylphenyl)-2,4,5,6,7,8-hexahydro-1,2,8-triazaazulene | 101.9-103.9 | 366 (366) |

TABLE 3-continued

| Cpd # | Structure | Name | mp (° C.) | H+ observed (predicted) |
|---|---|---|---|---|
| 3-5 | 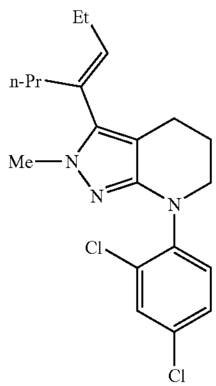 | 7-(2,4-Dichlorophenyl)-2-methyl-3-(1-propylbut-1-enyl)-4,5,6,7-tetrahydro-2H-pyrazolo[3,4-b]pyridine | oil | 378 (378) |
| 3-6 | 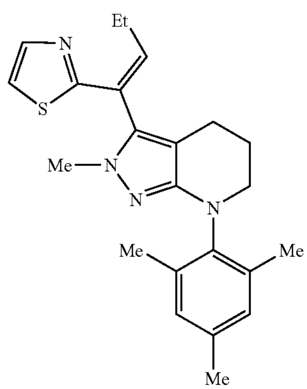 | 2-Methyl-3-(1-thiazol-2-ylbut-1-enyl)-7-(2,4,6-trimethyl-phenyl)-4,5,6,7-tetrahydro-2H-pyrazolo[3,4-b]pyridine | | 393 (393) |
| 3-7 | 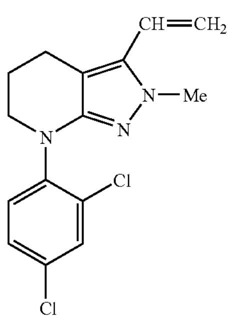 | 7-(2,4-Dichloro-phenyl)-2-methyl-3-vinyl-4,5,6,7-tetrahydro-2H-pyrazolo[3,4-b]pyridine | 99.6-100.6 | 308 (308) |
| 3-8 | 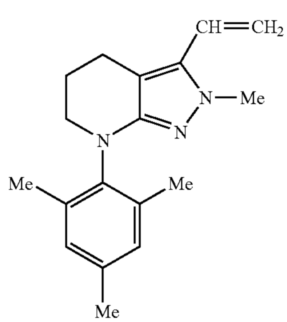 | 2-methyl-7-(2,4,6-trimethyl-phenyl)-3-vinyl-4,5,6,7-tetrahydro-2H-pyrazolo[3,4-b]pyridine | 64.4-67.6 | 282 (282) |

TABLE 3-continued

| Cpd # | Structure | Name | mp (° C.) | H+ observed (predicted) |
|---|---|---|---|---|
| 3-9 | 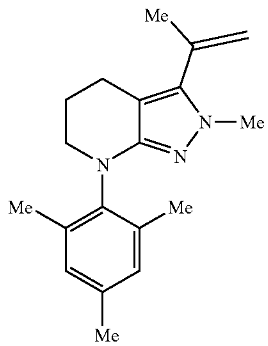 | 3-Isopropenyl-2-methyl-7-(2,4,6-trimethyl-phenyl)-4,5,6,7-tetrahydro-2H-pyrazolo[3,4-b]pyridine | 79.6-78.6 | 296 (296) |
| 3-10 | 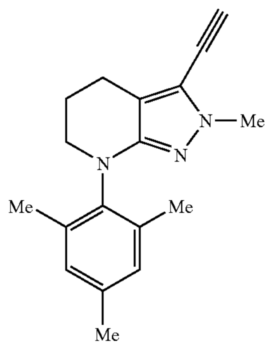 | 3-Ethynyl-2-methyl-7-(2,4,6-trimethyl-phenyl)-4,5,6,7-tetrahydro-2H-pyrazolo[3,4-b]pyridine | 105-107-5 | 306 (306) |

Example 9

7-(2-Chloro-4,6-dimethylphenyl)-2-methyl-3-(1-propylbutyl)-4,5,6,7-tetrahydro-2H-pyrazolo[3,4-b]pyridine (4-1)

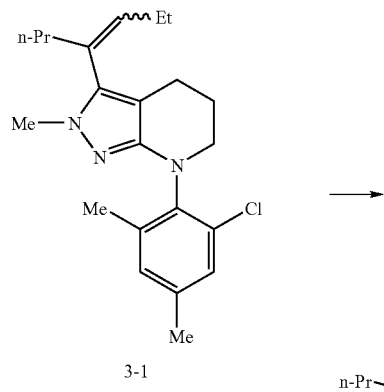

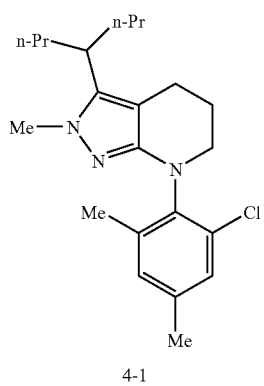

7-(2-Chloro-4,6-dimethylphenyl)-2-methyl-3-(1-propyl-but-1-enyl)-4,5,6,7-tetrahydro-2H-pyrazolo[3,4-b]pyridine (3-1; 41.5 mg) was dissolved in acetic acid (1 mL) and 12 mg of 10% palladium on carbon was added. The mixture was stirred under hydrogen at one atmosphere for 12 h. The mixture was diluted with ethyl acetate and filtered through diatomaceous earth and the residue was washed with ethyl acetate. The ethyl acetate filtrate was washed with aqueous sodium bicarbonate, dried with magnesium sulfate, and concentrated. The residue was chromatographed on silica gel eluting with an acetone/hexane gradient to provide 10.2 mg of 4-1 as a crystalline film: ms (MH+)=374.

Compounds 4-1 to 4-5

Compound 4-2 was prepared according to the procedure described in Example 9, except that compound 3-1 was replaced with compound 3-2.

Compound 4-3 was prepared according to the procedure described in Example 9 except that compound 3-1 was replaced with compound 3-3.

Compound 4-4 was prepared according to the procedure described in Example 9, except that compound 3-1 was replaced with compound 3-4.

Compound 4-5 was prepared according to the procedure described in Example 9, except that compound 3-1 was replaced with compound 3-8.

Compound 4-7 was prepared according to the procedure described in Example 9, except that compound 3-1 was replaced with compound 3-9.

Example 10

7-(2,4-Dichloro-phenyl)-3-ethyl-2-methyl-4,5,6,7-tetrahydro-2H-pyrazolo[3,4-b]pyridine (4-6)

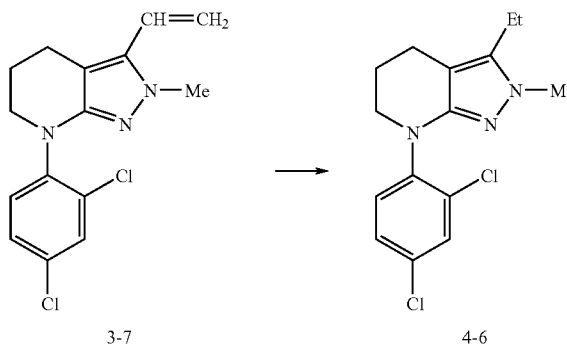

To a solution of 7-(2,4-dichloro-phenyl)-2-methyl-3-vinyl-4,5,6,7-tetrahydro-2H-pyrazolo[3,4-b]pyridine (3-7; 0.046 g, 0.15 mmol) in 2 mL of methanol was added dipotassium azodicarboxylate (0.174 g, 0.90 mmol) [prepared according to D. J. Pasto and R. J. Taylor, *Organic Reactions* 1991 40:91]. To the yellow suspension was added acetic acid (0.102 mL, 1.80 mmol) in 2 mL of methanol over 40 minutes. The reaction mixture was again treated with dipotassium azodicarboxylate (0.087 g, 0.45 mmol) and then acetic acid (0.051 mL, 0.90 mmol) in 1 mL of methanol over 20 nm. After 3 h at room temperature, the solvent was evaporated, the residue was treated with 10 mL of saturated sodium bicarbonate solution, extracted three times with 25 mL portions of dichloromethane, dried over magnesium sulfate, and evaporated to afford 41 mg of crude product. The crude product was purified by silica gel column chromatography eluting with 0 to 15% ethyl acetate/hexane which afforded 30 mg (65% theory) of 4-6 as a colorless oil: ms $(M+H)^+=310$.

TABLE 4

| Cpd # | Structure | Name | mp (° C.) | MH+ observed (predicted) |
|---|---|---|---|---|
| 4-1 | 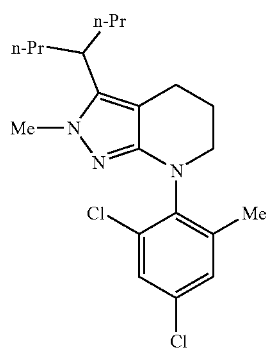 | 7-(2-Chloro-4,6-dimethylphenyl)-2-methyl-3-(1-propylbutyl)-4,5,6,7-tetrahydro-2H-pyrazolo[3,4-b]pyridine | | 374 (374) |
| 4-2 | 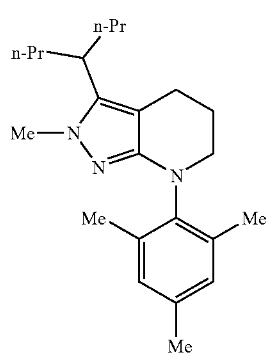 | 2-Methyl-3-(1-propylbutyl)-7-(2,4,6-trimethylphenyl)-4,5,6,7-tetrahydro-2H-pyrazolo[3,4-b]pyridine | 91.5-92 | 354 (354) |

TABLE 4-continued

| Cpd # | Structure | Name | mp (° C.) | MH+ observed (predicted) |
|---|---|---|---|---|
| 4-3 | 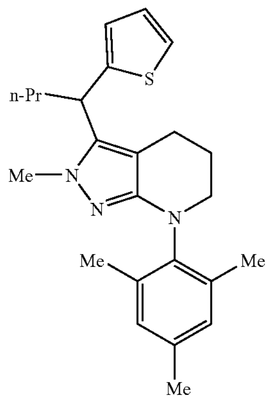 | 2-Methyl-3-(1-thiophen-2-ylbutyl)-7-(2,4,6-trimethylphenyl)-4,5,6,7-tetrahydro-2H-pyrazolo[3,4-b]pyridine | 87.6-90.3 | 394 (394) |
| 4-4 | 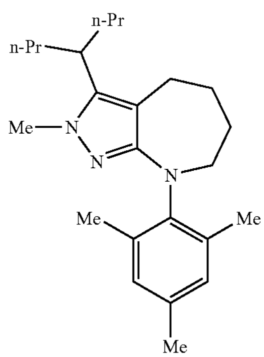 | 2-Methyl-3-(1-propylbutyl)-8-(2,4,6-trimethylphenyl)-2,4,5,6,7,8-hexahydro-1,2,8-triazaazulene | 96.0-98.1 | 368 (368) |
| 4-5 | 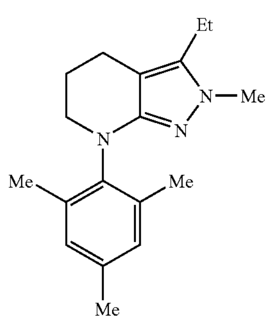 | 3-Ethyl-2-methyl-7-(2,4,6-trimethyl-phenyl)-4,5,6,7-tetrahydro-2H-pyrazolo[3,4-b]pyridine | 79.7-81.4 | 284 (284) |
| 4-6 | 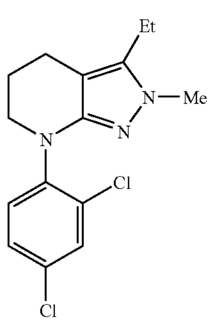 | 7-(2,4-dichlorophenyl)-3-ethyl-2-methyl-4,5,6,7-tetrahydro-2H-pyrazolo[3,4-b]pyridine | | 310 (310) |

TABLE 4-continued

| Cpd # | Structure | Name | mp (° C.) | MH+ observed (predicted) |
|---|---|---|---|---|
| 4-7 | (structure shown) | 3-Isopropyl-2-methyl-7-(2,4,6-trimethyl-phenyl)-4,5,6,7-tetrahydro-2H-pyrazolo[3,4-b]pyridine | 105.9–108.9 | 298 (298) |

Example 11

7-(2-Chloro-4,6-dimethylphenyl)-2-methyl-4,5,6,7-tetrahydro-2H-pyrazolo[3,4-b]pyridine-3-carboxylic acid (5-1)

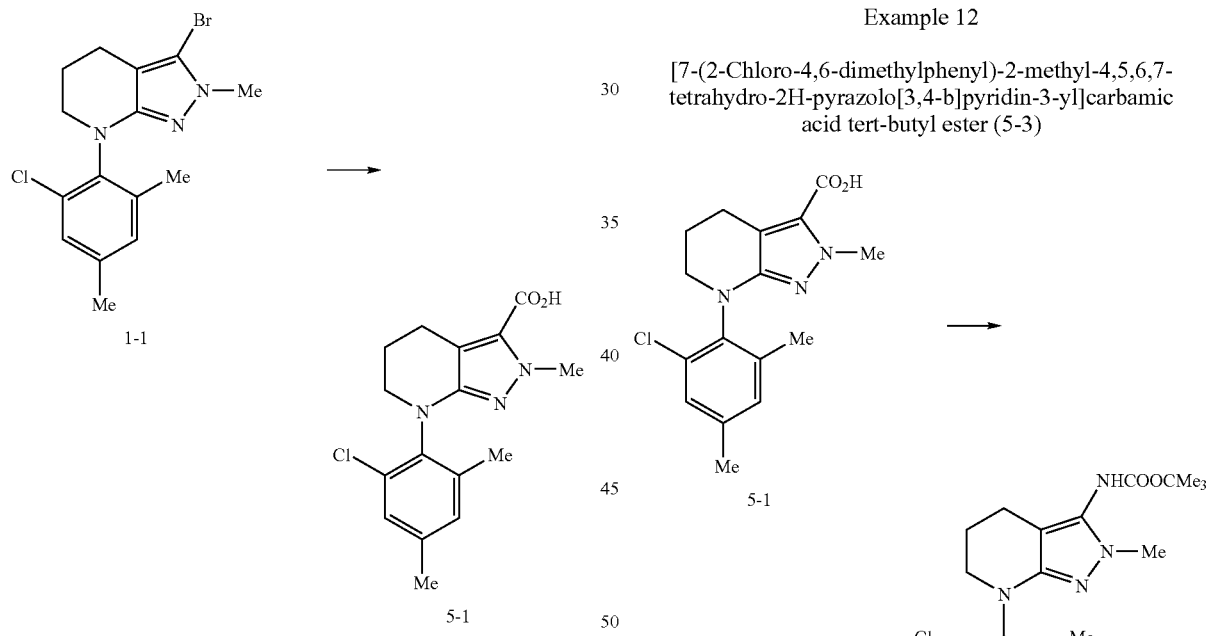

3-Bromo-7-(2-chloro-4,6-dimethylphenyl)-2-methyl-4,5,6,7-tetrahydro-2H-pyrazolo[3,4-b]pyridine (1-1; 1.46 g) and a few crystals of 1,10 phenanthroline were dissolved in 25 mL of dry tetrahydrofuran and chilled to −78° C. under an argon atmosphere. A 2.0 M solution of n-butyllithium in cyclohexane was added dropwise until the dark color of the phenanthroline/organolithium complex persisted. An additional 2.05 mL of the n-butyllithium solution was added. After 10 minutes, carbon dioxide, generated from dry ice, was bubbled through the reaction mixture for 5 minutes. After the reaction mixture had been stirred at −78° C. for 5 minutes, the cooling bath was removed and the mixture was allowed to warm for 5 minutes before being quenched by the addition of water. The mixture was partitioned between ethyl acetate and water, acidified with dilute hydrochloric acid. The ethyl acetate was dried with magnesium sulfate and concentrated. The residue was flash chromatographed on silica gel eluting with an acetone/hexane gradient to provide 1.11 g of 5-1: mp 247.8–248.3° C.

Compound 5-2 was prepared according to the procedure described in Example 11, except compound 1-1 was replaced with 1-3.

Example 12

[7-(2-Chloro-4,6-dimethylphenyl)-2-methyl-4,5,6,7-tetrahydro-2H-pyrazolo[3,4-b]pyridin-3-yl]carbamic acid tert-butyl ester (5-3)

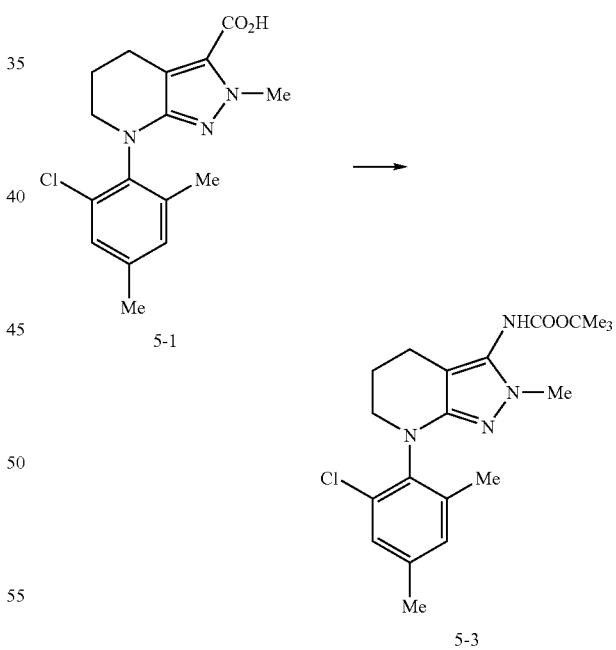

A 159 mg sample of 7-(2-chloro-4,6-dimethylphenyl)-2-methyl-4,5,6,7-tetrahydro-2H-pyrazolo[3,4-b]pyridine-3-carboxylic acid (5-1) was combined with 2.5 mL of t-butanol and 140 µL of triethylamine was added. To this mixture was added 129 µL of diphenylphosphoryl azide and the reaction mixture was heated to 85° C. for 2 h. After cooling to room temperature, the reaction mixture was dissolved in ethyl acetate and washed sequentially with 1M aqueous sodium bisulfate, aqueous sodium bicarbonate, water, and brine. The ethyl acetate solution was dried with magnesium sulfate and concentrated. The crude product was flash chromatographed on silica gel eluting with an acetone/hexane gradient to afford a solid residue which was slurried in a small amount of boiling hexane. After the mixture cooled to room temperature, the solids were collected by filtration to provide 71 mg of 5-3: mp 171.4-175.7° C.

Compound 5-4 was prepared according to the procedure described in Example 12 except that t-butanol was replaced by ethanol.

Example 13

[7-(2-Chloro-4,6-dimethylphenyl)-2-methyl-4,5,6,7-tetrahydro-2H-pyrazolo[3,4-b]pyridin-3-yl]dipropylamine (5-5)

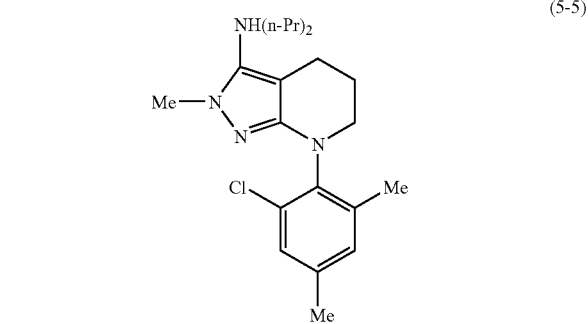

step 1

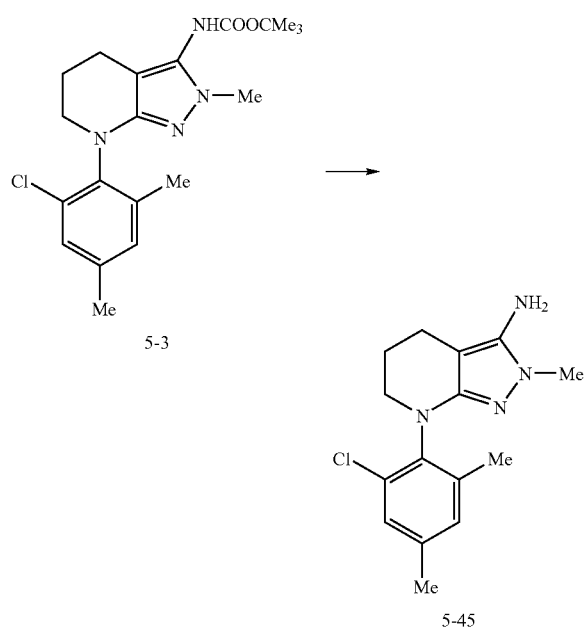

To a 0° C. solution of 287 mg of [7-(2-chloro-4,6-dimethylphenyl)-2-methyl-4,5,6,7-tetrahydro-2H-pyrazolo[3,4-b]pyridin-3-yl]carbamic acid tert-butyl ester (Example 12) in 9 mL of dichloromethane, was added 3 mL of trifluoroacetic acid. After 15 min, the cooling bath was removed and the reaction mixture was allowed to stir and warm to room temperature over 3 h. The reaction mixture was then diluted with dichloromethane and washed with dilute aqueous sodium hydroxide. The aqueous phase was washed with additional dichloromethane, after which the combined organics were dried with magnesium sulfate and concentrated. The residue was chromatographed on silica gel eluting with a methanol/dichloromethane gradient to provide 182 mg of 7-(2-chloro-4,6-dimethylphenyl)-2-methyl-4,5,6,7-tetrahydro-2H-pyrazolo[3,4-b]pyridin-3-ylamine (5-45): mp 234-236° C.

step 2

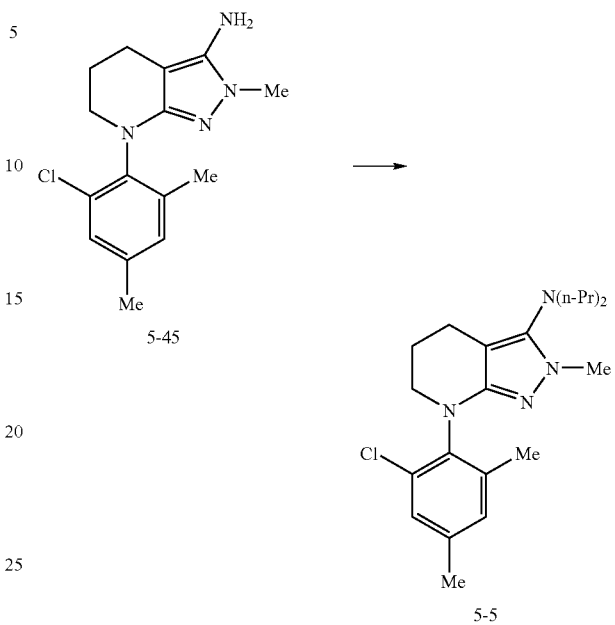

To a solution of 7-(2-chloro-4,6-dimethylphenyl)-2-methyl-4,5,6,7-tetrahydro-2H-pyrazolo[3,4-b]pyridin-3-ylamine (5-45; 55 mg) in 3 mL of dichloroethane was added 29 μL of propionaldehyde followed a few minutes later by 124 mg of sodium triacetoxyborohydride. The reaction mixture was stirred at room temperature for 2 d, during which time an additional 30 μL of propionaldehyde and an additional 62 mg of sodium triacetoxyborohydride were added to drive the reaction to completion. The mixture was diluted with dichloromethane and washed with dilute aqueous sodium hydroxide. The organic phase was dried over magnesium sulfate and evaporated. The residue was chromatographed on silica gel eluting with an acetone/hexane gradient to provide a solid which was recrystallized from hexane to afford 17 mg of 5-5: mp 90-91° C.

Example 14

[7-(2-chloro-4,6-dimethylphenyl)-2-methyl-4,5,6,7-tetrahydro-2H-pyrazolo[3,4-b]pyridin-3-yl](1-propylbutyl)amine (5-6)

Compound 5-6 was prepared according to the procedure described in Example 13, except that step 2 was performed as follows:

step 2

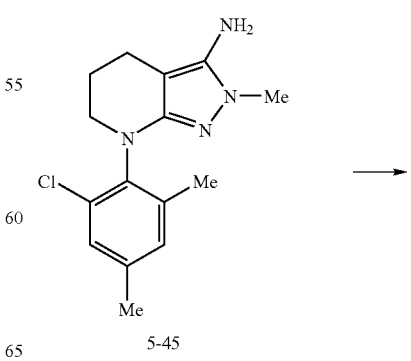

-continued

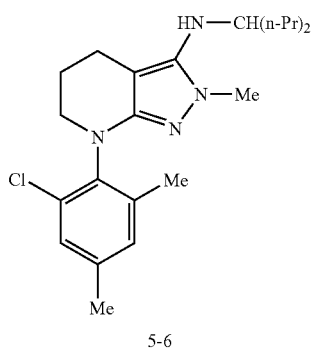

5-6

7-(2-Chloro-4,6-dimethylphenyl)-2-methyl-4,5,6,7-tetrahydro-2H-pyrazolo[3,4-b]pyridin-3-ylamine (5-45; 45.7 mg) and 4-heptanone (24 μL) were dissolved and stirred in 3 mL of dichloroethane. After 15 min, 44.5 mg of sodium triacetoxyborohydride was added. The reaction mixture was stirred at 60° C. during the day and at room temperature over night during 3 d. During this period, an additional 109 μL of 4-heptanone and an additional 104 mg of sodium triacetoxyborohydride were added to drive the reaction to completion. The reaction mixture was then partitioned between ethyl acetate and water. The ethyl acetate was dried with magnesium sulfate and evaporated. The crude product was chromatographed on silica gel eluting with an acetone/hexane gradient to provide 11 mg of crystalline [7-(2-chloro-4,6-dimethylphenyl)-2-methyl-4,5,6,7-tetrahydro-2H-pyrazolo[3,4-b]pyridin-3-yl](1-propylbutyl)amine (5-6): ms (MH$^+$)= 389.

Example 15

[7-(2-Chloro-4,6-dimethylphenyl)-2-methyl-4,5,6,7-tetrahydro-2H-pyrazolo[3,4-b]pyridin-3-yl]furan-2-ylmethylpropylamine (5-7)

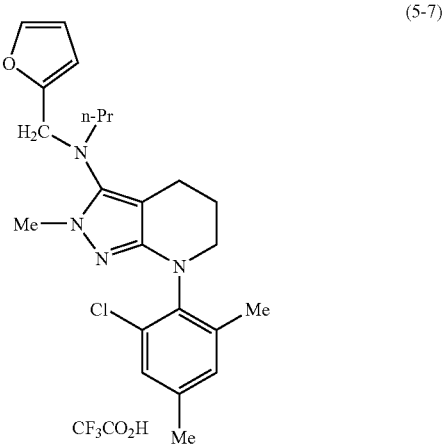

(5-7)

step 1:

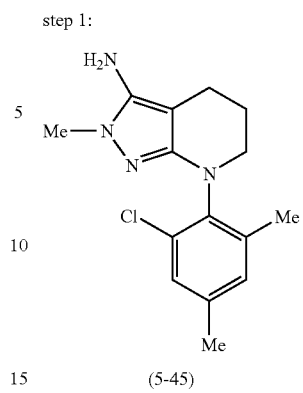

(5-45)

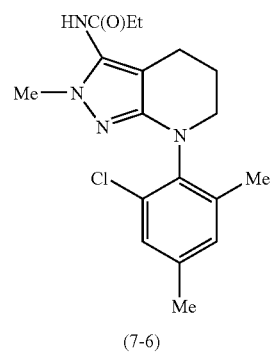

(7-6)

To a stirred solution of 7-(2-chloro-4,6-dimethylphenyl)-2-methyl-4,5,6,7-tetrahydro-2H-pyrazolo[3,4-b]pyridin-3-ylamine (5-45; 0.51 g) and triethylamine (0.27 mL) in dichloromethane (40 mL) cooled to 0° C. was added dropwise over 25 minutes a solution of propionyl chloride (0.17 mL) in dichloromethane (10 mL). The resulting mixture was stirred for an additional 1 h at 0° C., followed by 14 h at room temperature. The reaction mixture was stirred with an aqueous 5% citric acid solution (40 mL) for 10 minutes. The layers were separated, and the aqueous layer was further extracted with dichloromethane (50 mL). The combined organic extracts were dried over anhydrous sodium sulfate, decanted from the desiccating agent and concentrated in vacuo. The resulting residue was purified by silica gel chromatography using a dichloromethane/methanol gradient to afford N-[7-(2-chloro-4,6-dimethylphenyl)-2-methyl-4,5,6,7-tetrahydro-2H-pyrazolo[3,4-b]pyridin-3-yl]propionamide (7-6; 0.49 g) as an off white solid: ms (MH$^+$)=347.

step 2

7-6

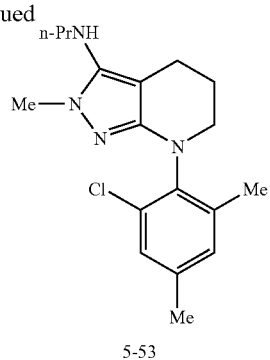

5-53

To a stirred, chilled (0° C.) solution of N-[7-(2-chloro-4,6-dimethylphenyl)-2-methyl-4,5,6,7-tetrahydro-2H-pyrazolo[3,4-b]pyridin-3-yl]propionamide (0.48 g) in tetrahydrofuran (9 mL), under nitrogen, was added borane-THF complex (4.1 mL of a 1.0 M tetrahydrofuran solution) in one portion. The resulting mixture was stirred for 1 h at 0° C., then stirred for 48 h at room temperature. The reaction mixture was treated with 1:2 acetic acid/ethyl acetate (11 mL), mixed briefly, and allowed to stand at room temperature for 24 h. The resulting mixture was added to a 3% aqueous sodium hydroxide solution (75 mL), and extracted with ethyl acetate (3×75 mL). The combined organic extracts were dried over anhydrous sodium sulfate, then decanted from the desiccating agent and concentrated in vacuo to afford, [7-(2-chloro-4,6-dimethylphenyl)-2-methyl-4,5,6,7-tetrahydro-2H-pyrazolo[3,4-b]pyridin-3-yl]propylamine (5-53; 0.45 g), as a pale yellow solid which was used directly in step 3: ms (MH$^+$)=333.

step 3

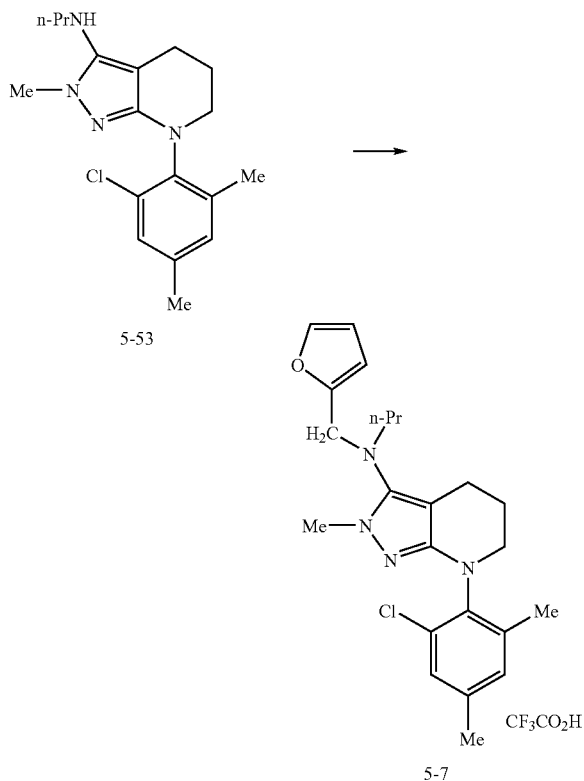

[7-(2-Chloro-4,6-dimethylphenyl)-2-methyl-4,5,6,7-tetrahydro-2H-pyrazolo[3,4-b]pyridin-3-yl]propylamine (17 mg) was treated with a solution of 2-furancarboxaldehyde (9 mg) in 1,2-dichloroethane (0.38 mL). To the resulting mixture was added acetic acid (15 mg), followed by sodium triacetoxyborohydride (30 mg). The resulting mixture was agitated for 72 hours at room temperature using a rotary shaker. The reaction mixture was then treated with saturated aqueous sodium bicarbonate (2 mL) and extracted with ethyl acetate (3×2 mL). The combined organic extracts were then concentrated in vacuo. The resulting orange-yellow residue was purified by preparative high-pressure liquid chromatography (HPLC) on reversed-phase (C18) silica gel (gradient, acetonitrile-0.1% trifluoroacetic acid=10:90 to 90:10) to afford [7-(2-chloro-4,6-dimethylphenyl)-2-methyl-4,5,6,7-tetrahydro-2H-pyrazolo[3,4-b]pyridin-3-yl]furan-2-ylmethylpropylamine, trifluoroacetate salt (5-7; 5 mg) as a yellow solid: ms (MH$^+$)=413.

Example 16

(1-Methoxymethylpropyl)-[2-methyl-7-(2,4,6-trimethylphenyl)-4,5,6,7-tetrahydro-2H-pyrazolo[3,4-b]pyridin-3-yl]-amine (5-40)

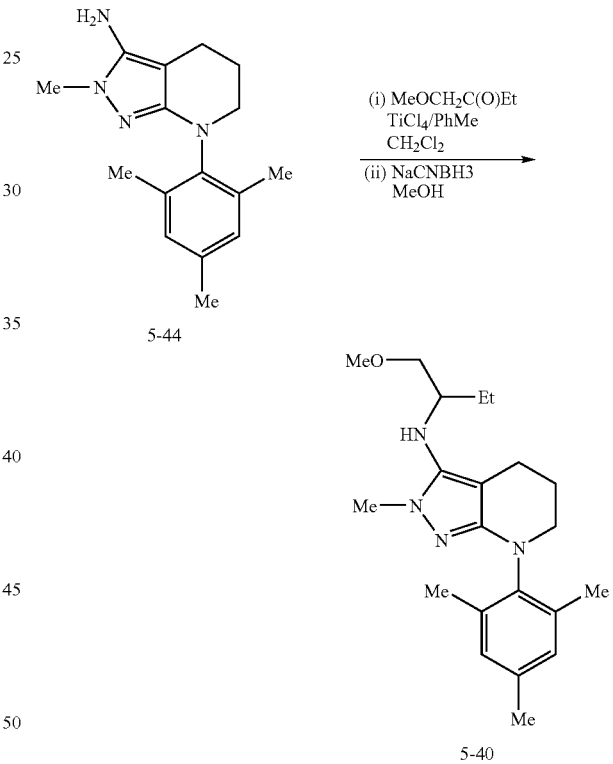

2-Methyl-7-(2,4,6-trimethyl-phenyl)-4,5,6,7-tetrahydro-2H-pyrazolo[3,4-b]pyridin-3-ylamine (5-44; 101 mg, 0.373 mmol) was dissolved in CH$_2$Cl$_2$ (2 mL). Et$_3$N (0.25 mL, 1.79 mmol) and the 1-methoxy-butan-2-one (65 mg, 0.636 mmol) were added at room temperature. A solution of TiCl$_4$ in toluene (1 M; 0.35 mL, 0.35 mmol) was added dropwise via syringe. The mixture was then stirred at room temperature overnight. NaCNBH$_3$ (120 mg, 1.9 mmol) in methanol (1 mL) was added slowly. The stirring continued at room temperature for 0.5 h and the reaction was quenched by the addition of 2 N NaOH (2 mL). EtOAc was added and the layers were separated. The organic layer was washed with water, brine and dried over MgSO$_4$. The solvent was removed and the residue purified by chromatography on SiO$_2$ (gradient elution: 2% MeOH in CH$_2$Cl$_2$ containing 0.1% NH$_4$OH to 3% MeOH in CH$_2$Cl$_2$ containing 0.15% NH$_4$OH over 20 minutes) to yield 102 mg of 5-40 (0.286 mmol; 77%).

Example 17

Methyl-[2-methyl-7-(2,4,6-trimethyl-phenyl)-4,5,6,7-tetrahydro-2H-pyrazolo[3,4-b]pyridin-3-yl]-amine (5-49)

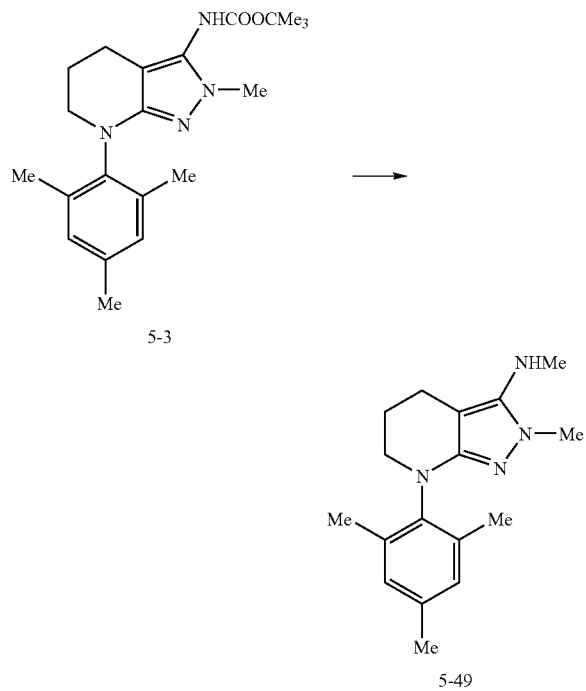

[2-methyl-7-(2,4,6-trimethylphenyl)-4,5,6,7-tetrahydro-2H-pyrazolo[3,4-b]pyridin-3-yl]carbamic acid tert-butyl ester was prepared according to Example 12 except compound 5-1 was replaced with compound 5-2.

A solution of [2-methyl-7-(2,4,6-trimethyl-phenyl)-4,5,6,7-tetrahydro-2H-pyrazolo[3,4-b]pyridin-3-yl]-carbamic acid tert-butyl ester (0.150 g, 0.40 mmol) dissolved in THF (3 mL) was treated with the slow addition of 1M lithium aluminum hydride in THF (0.80 mL, 0.80 mmol). The mixture was placed under a nitrogen atmosphere and heated to reflux for 8 h. The mixture was cooled to room temperature and the excess reagent was quenched by the dropwise addition of 10% potassium sodium tartrate solution. Ethyl acetate (40 mL) was added and washed sequentially with 10% Rochelle salt solution (40 mL) and brine (25 m), dried over magnesium sulfate, and evaporated. The residue was purified by silica gel chromatography eluting with ethyl acetate/hexane (3:2) to afford 0.056 g (48% yield) of methyl-[2-methyl-7-(2,4,6-trimethyl-phenyl)-4,5,6,7-tetrahydro-2H-pyrazolo[3,4-b]pyridin-3-yl]-amine (5-49): mp 143.3-144.9° C.

Compound 5-8 was prepared according to the procedure described in Example 15, except that in step 3, 2-furancarboxaldehyde was replaced by pyridine-2-carboxaldehyde.

Compound 5-9 was prepared according to the procedure described in Example 15, except that in step 3, 2-furancarboxaldehyde was replaced by pyridine-4-carboxaldehyde.

Compound 5-10 was prepared according to the procedure described in Example 15, except that in step 3, 2-furancarboxaldehyde was replaced by imidazole-2-carboxaldehyde.

Compound 5-11 was prepared according to the procedure described in Example 15, except that in step 3, 2-furancarboxaldehyde was replaced by pyridine-3-carboxaldehyde.

Compound 5-12 was prepared according to the procedure described in Example 15, except that in step 3, 2-furancarboxaldehyde was replaced by imidazole-4-carboxaldehyde.

Compound 5-13 was prepared according to the procedure described in Example 15, except that in step 3, 2-furancarboxaldehyde was replaced by 3,4,5-trimethoxybenzaldehyde.

Compound 5-14 was prepared according to the procedure described in Example 15, except that in step 3, 2-furancarboxaldehyde was replaced by 2,3,4-trimethoxybenzaldehyde.

Compound 5-15 was prepared according to the procedure described in Example 15, except that in step 3, 2-furancarboxaldehyde was replaced by 1-methylimidazole-4-carboxaldehyde.

Compound 5-16 was prepared according to the procedure described in Example 15, except that in step 3, 2-furancarboxaldehyde was replaced by 3-methylimidazole-4-carboxaldehyde.

Compound 5-17 was prepared according to the procedure described in Example 15, step 3, except 2-furancarboxaldehyde was replaced by thiazole-2-carboxaldehyde and [7-(2-chloro-4,6-dimethyl-phenyl)-4,5,6,7-tetrahydro-2H-pyrazolo[3,4-b]pyridin-3-yl]-propyl-amine (5-53) was replaced by (2-methoxy-ethyl)-[7-(2,4,6-trimethyl-phenyl)-4,5,6,7-tetrahydro-2H-pyrazolo[3,4-b]pyridin-3-yl]-amine (5-54).

Compound 5-18 was prepared according to the procedure described in Example 15, step 3, except that compound 5-53 was replaced with compound 5-54.

Compound 5-19 was prepared according to the procedure described in Example 15, step 3, except that 2-furancarboxaldehyde was replaced with 3,4,5-trimethoxybenzaldehyde and compound 5-53 was replaced with compound 5-54.

Compound 5-20 was prepared according to the procedure described in Example 15, step 3, except that 2-furancarboxaldehyde was replaced with 4-cyanobenzaldehyde and compound 5-53 was replaced with compound 5-54.

Compound 5-21 was prepared according to the procedure described in Example 15, step 3, except that 2-furancarboxaldehyde was replaced with propionaldehyde and compound 5-53 was replaced with compound 5-54.

Compound 5-22 was prepared according to the procedure described in Example 15, step 3, except that 2-furancarboxaldehyde was replaced with 3,4-dimethoxybenzaldehyde and compound 5-53 was replaced with compound 5-54.

Compound 5-23 was prepared according to the procedure described in Example 15, step 3, except that 2-furancarboxaldehyde was replaced with cyclopropylcarboxaldehyde and compound 5-53 was replaced with compound 5-54.

Compound 5-24 was prepared according to the procedure described in Example 15, step 3, except that 2-furancarboxaldehyde was replaced with benzaldehyde and compound 5-53 was replaced with compound 5-54.

Compound 5-25 was prepared according to the procedure described in Example 15, step 3, except that 2-furancarboxaldehyde was replaced with n-butyraldehyde and compound 5-53 was replaced with compound 5-54.

Compound 5-26 was prepared according to the procedure described in Example 15, step 3, except that 2-furancarboxaldehyde was replaced by thiazole-2-carboxaldehyde and compound 5-53 was replaced with compound 5-55.

Compound 5-27 was prepared according to the procedure described in Example 15, step 3 except that 2-furancarboxaldehyde was replaced by 4-cyanobenzaldehyde and compound 5-53 was replaced with compound 5-55.

Compound 5-28 was prepared according to the procedure described in Example 15, step 3, except that 2-furancarboxaldehyde was replaced by 3,4-dimethoxybenzaldehyde and compound 5-53 was replaced with compound 5-55.

Compound 5-29 was prepared according to the procedure described in Example 15, step 3, except that 2-furancarboxaldehyde was replaced by cyclopropanecarboxaldehyde and compound 5-53 was replaced with compound 5-55.

Compound 5-30 was prepared according to the procedure described in Example 15, step 3, except that 2-furancarboxaldehyde was replaced by benzaldehyde and compound 5-53 was replaced with compound 5-55.

Compound 5-31 was prepared according to the procedure described in Example 15, step 3, except that 2-furancarboxaldehyde was replaced by n-butyraldehyde and compound 5-53 was replaced with compound 5-55.

Compound 5-32 was prepared according to the procedure described in Example 15, step 3, except that 2-furancarboxaldehyde was replaced by thiophene-2-carboxaldehyde and compound 5-53 was replaced with compound 5-55.

Compound 5-33 was prepared according to the procedure described in Example 15, step 3, except that 2-furancarboxaldehyde was replaced with acetaldehyde and compound 5-53 was replaced with compound 5-54.

Compound 5-34 was prepared according to the procedure described in Example 15, step 3, except that 2-furancarboxaldehyde was replaced by acetaldehyde and compound 5-53 was replaced with compound 5-55.

Compound 5-35 was prepared according to the procedure described in Example 15, step 3, except that 2-furancarboxaldehyde was replaced by n-propionaldehyde and compound 5-53 was replaced with compound 5-55.

Compound 5-36 was prepared according to the procedure described in Example 16 except that 1-methoxy-butan-2-one was replaced with 3-pentanone.

Compound 5-37 was prepared according to the procedure described in Example 16 except that 1-methoxy-butan-2-one was replaced with 1,3-dimethoxy-propan-2-one.

Compound 5-38 was prepared according to the procedure described in Example 16 except that 1-methoxy-butan-2-one was replaced with 1,4-dimethoxy-butanone.

Compound 5-39 was prepared according to the procedure described in Example 15, step 3, except that 2-furancarboxaldehyde was replaced with cyclopropylcarboxaldehyde and compound 5-53 was replaced with compound 5-54.

Compound 5-40 was prepared according to the procedure described in Example 16 except that 1-methoxy-butan-2-one was replaced with 1-methoxy-2-butanone.

Compound 541 was prepared according to the procedure described in Example 16 except that 1-methoxy-butan-2-one was replaced with 1-methoxy-2-pentanone.

Compound 5-42 was prepared by treating propyl 7-(2,4,6-trimethylphenyl)-2-methyl-4,5,6,7-tetrahydro-2H-pyrazolo[3,4-b]pyridin-3-ylamine (5-55) with phenylsulfonyl chloride utilizing Schotten-Bauman conditions.

Compound 5-43 and 5-44 were prepared as in step 1 of Example 13 except [7-(2-chloro-4,6-dimethylphenyl)-2-methyl-4,5,6,7-tetrahydro-2H-pyrazolo[3,4-b]pyridin-3-yl]carbamic acid tert-butyl ester (5-3) was replaced by [7-(2,4-dichlorophenyl)-2-methyl-4,5,6,7-tetrahydro-2H-pyrazolo[3,4pyridin-3-yl]carbamic acid tert-butyl ester and [2-methyl-7-(2,4,6-trimethyl-phenyl)-4,5,6,7-b]-tetrahydro-2H-pyrazolo[3,4-b]pyridin-3-yl]-carbamic acid tert-butyl ester, respectively.

Compound 5-46 was prepared as in Example 13, step 2, except that compound 5-45 was replaced with 5-43.

Compound 5-47 was prepared as in Example 13, step 2, except that propionaldehyde was replaced by formaldehyde and compound 5-45 was replaced with 5-44.

Compound 5-48 was prepared as in Example 15, step 3, except that compound 5-53 was replaced with [2-methyl-7-(2,4,6-trimethyl-phenyl)-4,5,6,7-tetrahydro-2H-pyrazolo[3,4-b]pyridin-3-yl]-propyl-amine (5-55) and furan-2-carboxaldehyde was replaced with 3-cyanopropionaldehyde.

Compound 5-50 was prepared by acylation of compound 5-55 with ethyl 3-chloro-3-oxopropionate, followed by treatment of the resultant amide with lithium aluminum hydride.

Compound 5-54 was prepared according to the procedure described in Example 15, steps 1 and 2, except that in step 1, 7-(2-chloro-4,6-dimethylphenyl)-2-methyl-4,5,6,7-tetrahydro-2H-pyrazolo[3,4-b]pyridin-3-ylamine (5-45) was replaced with 2-methyl-7-(2,4,6-trimethyl-phenyl)-4,5,6,7-tetrahydro-2H-pyrazolo[3,4-b]pyridin-3-ylamine (5-52) and propionyl chloride was replaced with methoxyacetyl chloride.

Compound 5-55 was prepared according to the procedure in Example 15, steps 1 and 2, except that in step 1, 7-(2-chloro-4,6-dimethylphenyl)-2-methyl-4,5,6,7-tetrahydro-2H-pyrazolo[3,4-b]pyridin-3-ylamine (5-45) was replaced with 2-methyl-7-(2,4,6-trimethyl-phenyl)-4,5,6,7-tetrahydro-2H-pyrazolo[3,4-b]pyridin-3-ylamine (5-44).

TABLE 5

| Cpd # | Structure | Name | mp (° C.) | MH+ observed (predicted) |
|---|---|---|---|---|
| 5-1 | 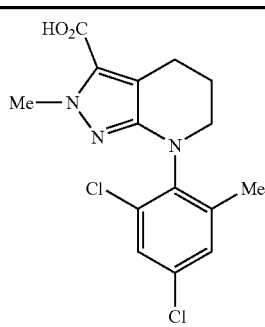 | 7-(2-Chloro-4,6-dimethylphenyl)-2-methyl-4,5,6,7-tetrahydro-2H-pyrazolo[3,4-b]pyridine-3-carboxylic acid | 247.8-248.3 | 320 (320) |

TABLE 5-continued

| Cpd # | Structure | Name | mp (° C.) | MH+ observed (predicted) |
|---|---|---|---|---|
| 5-2 | 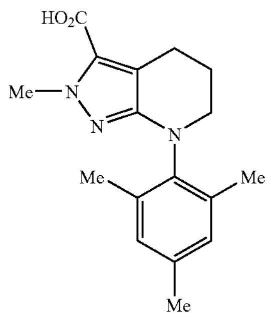 | 7-(2,4,6-Trimethylphenyl)-2-methyl-4,5,6,7-tetrahydro-2H-pyrazolo[3,4-b]pyridine-3-carboxylic acid | 228.6-233.9 | 300 (300) |
| 5-3 | 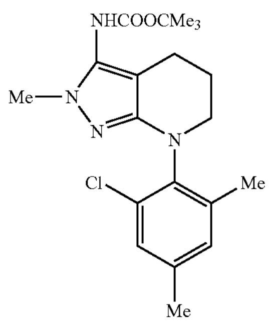 | [7-(2-Chloro-4,6-dimethylphenyl)-2-methyl-4,5,6,7-tetrahydro-2H-pyrazolo[3,4-b]pyridin-3-yl]carbamic acid tert-butyl ester | 171.4-175.7 | 391 (391) |
| 5-4 | 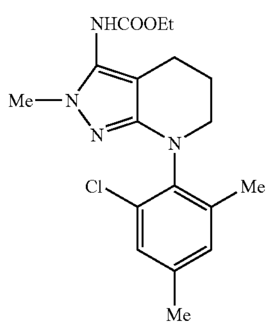 | [7-(2-Chloro-4,6-dimethylphenyl)-2-methyl-4,5,6,7-tetrahydro-2H-pyrazolo[3,4-b]pyridin-3-yl]carbamic acid ethyl ester | 204.0-207.8 | 363 (363) |
| 5-5 | 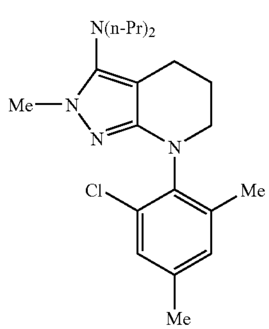 | [7-(2-Chloro-4,6-dimethylphenyl)-2-methyl-4,5,6,7-tetrahydro-2H-pyrazolo[3,4-b]pyridin-3-yl]dipropylamine | 90-91 | 375 (375) |

TABLE 5-continued

| Cpd # | Structure | Name | mp (° C.) | MH+ observed (predicted) |
|---|---|---|---|---|
| 5-6 | 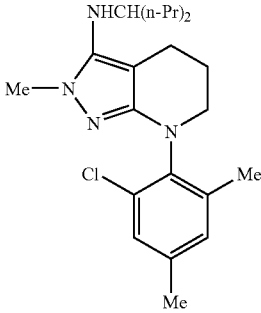 | [7-(2-Chloro-4,6-dimethylphenyl)-2-methyl-4,5,6,7-tetrahydro-2H-pyrazolo[3,4-b]pyridin-3-yl](1-propylbutyl)amine | | 389 (389) |
| 5-7 | 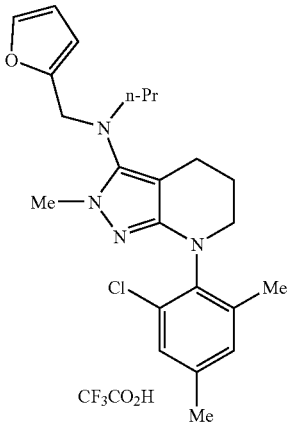 | [7-(2-Chloro-4,6-dimethyl-phenyl)-2-methyl-4,5,6,7-tetrahydro-2H-pyrazolo[3,4-b]pyridin-3-yl]-furan-2-ylmethyl-propyl-amine trifluoroacetic acid salt | | 413 (413) |
| 5-8 | 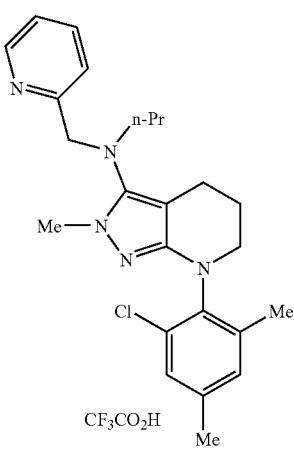 | [7-(2-Chloro-4,6-dimethyl-phenyl)-2-methyl-4,5,6,7-tetrahydro-2H-pyrazolo[3,4-b]pyridin-3-yl]-propyl-pyridin-2-ylmethyl-amine trifluoroacetic acid salt | | 424 (424) |

TABLE 5-continued

| Cpd # | Structure | Name | mp (° C.) | MH+ observed (predicted) |
|---|---|---|---|---|
| 5-9 | 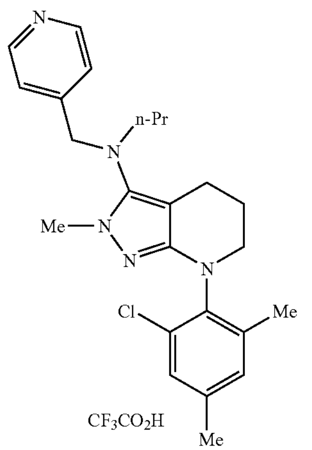 | [7-(2-Chloro-4,6-dimethyl-phenyl)-2-methyl-4,5,6,7-tetrahydro-2H-pyrazolo[3,4-b]pyridin-3-yl]-propyl-pyridin-4-ylmethyl-amine trifluoroacetic acid salt | | 424 (424) |
| 5-10 | 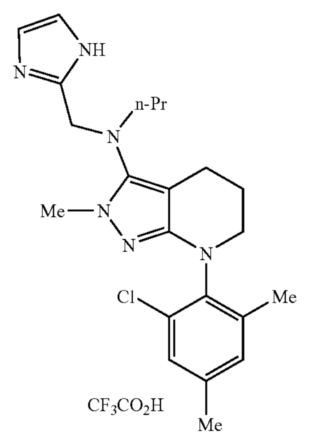 | [7-(2-Chloro-4,6-dimethyl-phenyl)-2-methyl-4,5,6,7-tetrahydro-2H-pyrazolo[3,4-b]pyridin-3-yl]-(1H-imidazol-2-ylmethyl)-propyl-amine trifluoroacetic acid salt | | 413 (413) |
| 5-11 | 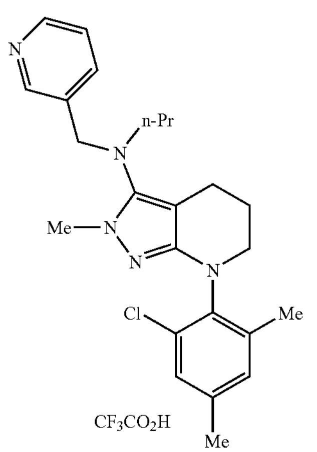 | [7-(2-Chloro-4,6-dimethyl-phenyl)-2-methyl-4,5,6,7-tetrahydro-2H-pyrazolo[3,4-b]pyridin-3-yl]-propyl-pyridin-3-ylmethyl-amine trifluoroacetic acid salt | | 424 (424) |

TABLE 5-continued

| Cpd # | Structure | Name | mp (° C.) | MH+ observed (predicted) |
|---|---|---|---|---|
| 5-12 | 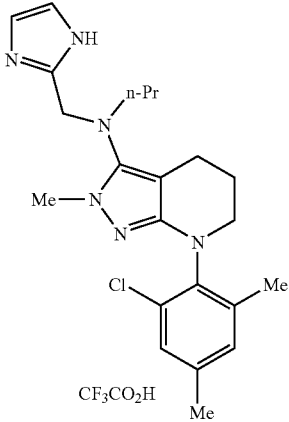 | [7-(2-Chloro-4,6-dimethyl-phenyl)-2-methyl-4,5,6,7-tetrahydro-2H-pyrazolo[3,4-b]pyridin-3-yl]-(1H-imidazol-4-ylmethyl)-propyl-amine trifluoroacetic acid salt | | 413 (413) |
| 5-13 | 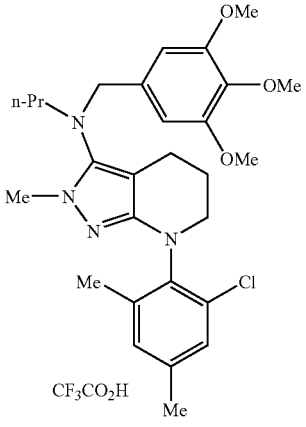 | [7-(2-Chloro-4,6-dimethyl-phenyl)-2-methyl-4,5,6,7-tetrahydro-2H-pyrazolo[3,4-b]pyridin-3-yl]-propyl-(3,4,5-trimethoxy-benzyl)-amine trifluoroacetic acid salt | | 513 (513) |
| 5-14 | 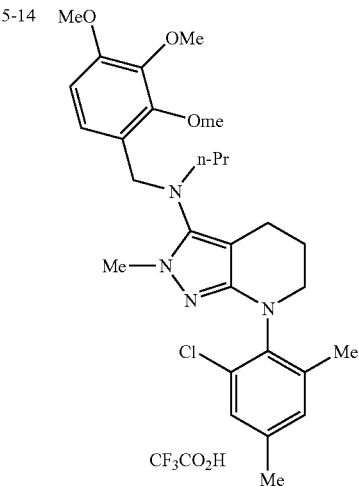 | [7-(2-Chloro-4,6-dimethyl-phenyl)-2-methyl-4,5,6,7-tetrahydro-2H-pyrazolo[3,4-b]pyridin-3-yl]-propyl-(2,3,4-trimethoxy-benzyl)-amine trifluoroacetic acid salt | | 513 (513) |

TABLE 5-continued

| Cpd # | Structure | Name | mp (° C.) | MH+ observed (predicted) |
|---|---|---|---|---|
| 5-15 | 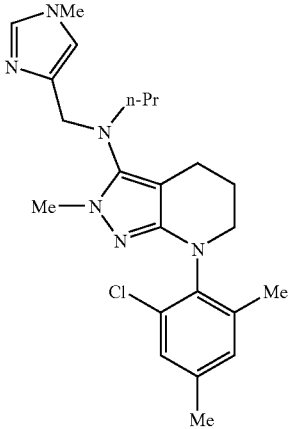 | [7-(2-Chloro-4,6-dimethyl-phenyl)-2-methyl-4,5,6,7-tetrahydro-2H-pyrazolo[3,4-b]pyridin-3-yl]-(1-methyl-1H-imidazol-4-ylmethyl)-propyl-amine trifluoroacetic acid salt | | 427 (427) |
| 5-16 | 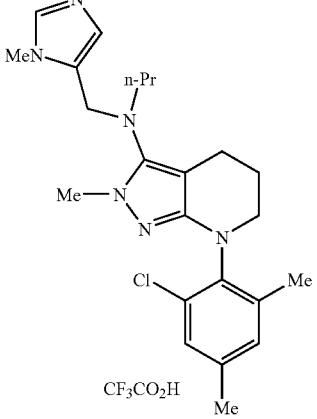 | [7-(2-Chloro-4,6-dimethyl-phenyl)-2-methyl-4,5,6,7-tetrahydro-2H-pyrazolo[3,4-b]pyridin-3-yl]-(3-methyl-3H-imidazol-4-ylmethyl)-propyl-amine trifluoroacetic acid salt | | 427 (427) |
| 5-17 | 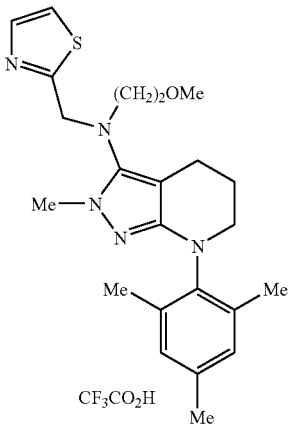 | (2-Methoxy-ethyl)-[2-methyl-7-(2,4,6-trimethylphenyl)-4,5,6,7-tetrahydro-2H-pyrazolo[3,4-b]pyridin-3-yl]thiazol-2-ylmethylamine, trifluoroacetic acid salt | | 426 (426) |

TABLE 5-continued

| Cpd # | Structure | Name | mp (° C.) | MH+ observed (predicted) |
|---|---|---|---|---|
| 5-18 | 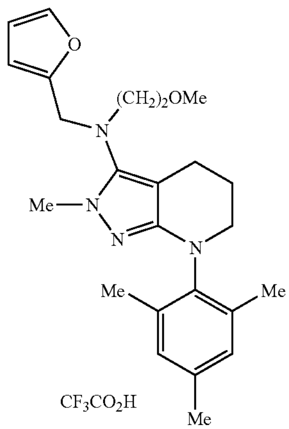 | Furan-2-ylmethyl-(2-methoxy-ethyl)-[2-methyl-7-(2,4,6-trimethyl-phenyl)-4,5,6,7-tetrahydro-2H-pyrazolo[3,4-b]pyridin-3-yl]amine, trifluoroacetic acid salt | | 409 (409) |
| 5-19 | 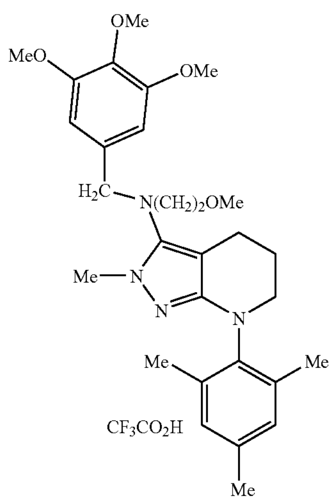 | (2-Methoxyethyl)-[2-methyl-7-(2,4,6-trimethylphenyl)-4,5,6,7-tetrahydro-2H-pyrazolo[3,4-b]pyridin-3-yl]-(3,4,5-trimethoxy-benzyl)amine, trifluoroacetic acid salt | | 509 (509) |
| 5-20 | 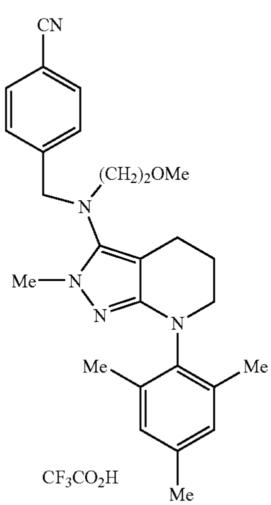 | 4-({(2-Methoxyethyl)-[2-methyl-7-(2,4,6-trimethylphenyl)-4,5,6,7-tetrahydro-2H-pyrazolo[3,4-b]pyridin-3-yl]amino}methyl)benzonitrile, trifluoroacetic acid salt | | 444 (444) |

TABLE 5-continued

| Cpd # | Structure | Name | mp (° C.) | MH+ observed (predicted) |
|---|---|---|---|---|
| 5-21 | 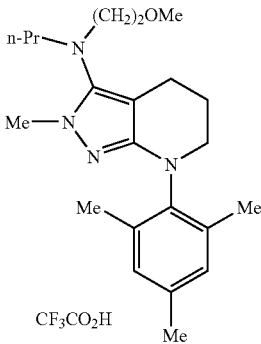 | (2-Methoxyethyl)-[2-methyl-7-(2,4,6-trimethylphenyl)-4,5,6,7-tetrahydro-2H-pyrazolo[3,4-b]pyridin-3-yl]-propylamine, trifluoroacetic acid salt | | 371 (371) |
| 5-22 | 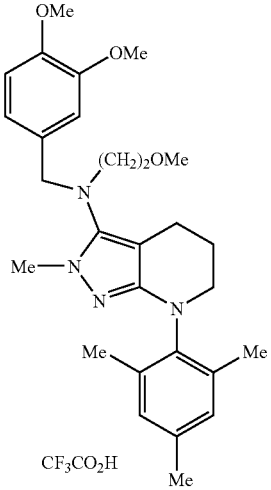 | (3,4-Dimethoxybenzyl)-(2-methoxyethyl)-[2-methyl-7-(2,4,6-trimethyl-phenyl)-4,5,6,7-tetrahydro-2H-pyrazolo[3,4-b]pyridin-3-yl]-amine, trifluoroacetic acid salt | | 479 (479) |
| 5-23 | 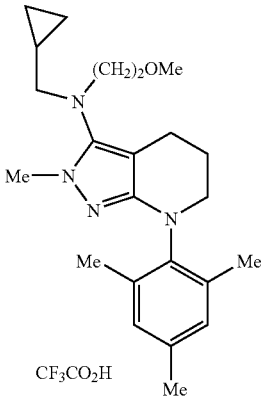 | Cyclopropylmethyl-(2-methoxyethyl)-[2-methyl-7-(2,4,6-trimethylphenyl)-4,5,6,7-tetrahydro-2H-pyrazolo[3,4-b]pyridin-3-yl]-amine | oil | 383 (383) |

TABLE 5-continued

| Cpd # | Structure | Name | mp (° C.) | MH+ observed (predicted) |
|---|---|---|---|---|
| 5-24 | 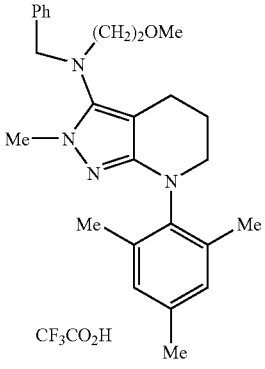 | Benzyl-(2-methoxyethyl)-[2-methyl-7-(2,4,6-trimethylphenyl)-4,5,6,7-tetrahydro-2H-pyrazolo[3,4-b]pyridin-3-yl]-amine, trifluoroacetic acid salt | | 419 (419) |
| 5-25 | 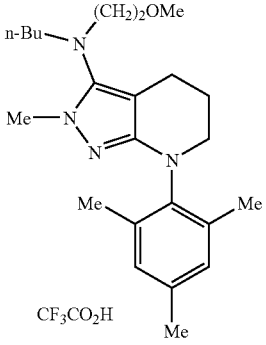 | Butyl-(2-methoxyethyl)-[2-methyl-7-(2,4,6-trimethylphenyl)-4,5,6,7-tetrahydro-2H-pyrazolo[3,4-b]pyridin-3-yl]-amine, trifluoroacetic acid salt | | 385 (385) |
| 5-26 | 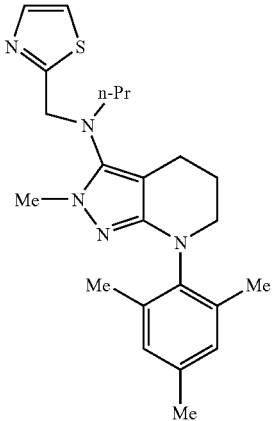 | [2-Methyl-7-(2,4,6-trimethylphenyl)-4,5,6,7-tetrahydro-2H-pyrazolo[3,4-b]pyridin-3-yl]-propylthiazol-2-ylmethylamine, trifluoroacetic acid salt | | 410 (410) |

TABLE 5-continued

| Cpd # | Structure | Name | mp (° C.) | MH+ observed (predicted) |
|---|---|---|---|---|
| 5-27 | 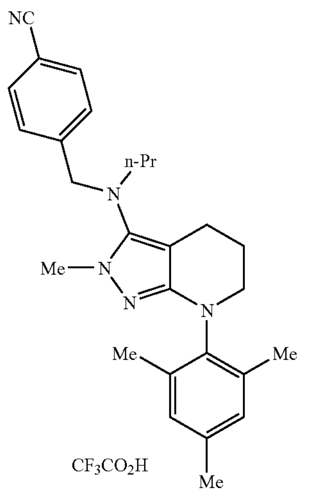 | 4-({[2-Methyl-7-(2,4,6-trimethyl-phenyl)-4,5,6,7-tetrahydro-2H-pyrazolo[3,4-b]pyridin-3-yl]-propylamino}-methyl)-benzonitrile, trifluoroacetic acid salt | | 428 (428) |
| 5-28 | 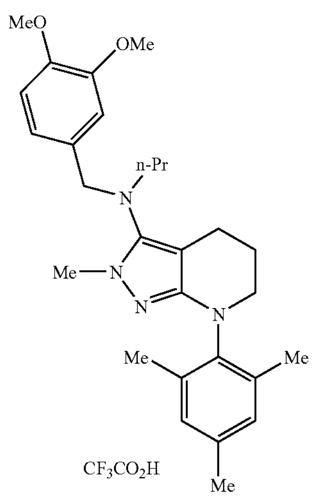 | (3,4-Dimethoxybenzyl)-[2-methyl-7-(2,4,6-trimethylphenyl)-4,5,6,7-tetrahydro-2H-pyrazolo[3,4-b]pyridin-3-yl]-propylamine, trifluoroacetic acid salt | | 463 (463) |
| 5-29 | 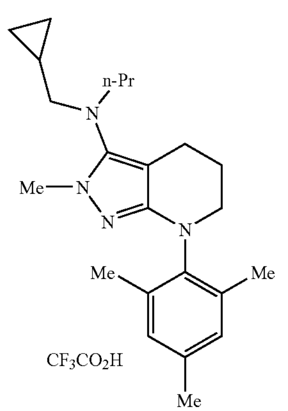 | Cyclopropylmethyl-[2-methyl-7-(2,4,6-trimethylphenyl)-4,5,6,7-tetrahydro-2H-pyrazolo[3,4-b]pyridin-3-yl]-propylamine, trifluoroacetic acid salt | | 367 (367) |

TABLE 5-continued

| Cpd # | Structure | Name | mp (° C.) | MH+ observed (predicted) |
|---|---|---|---|---|
| 5-30 | 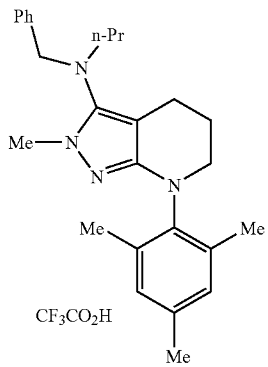 | Benzyl-[2-methyl-7-(2,4,6-trimethylphenyl)-4,5,6,7-tetrahydro-2H-pyrazolo[3,4-b]pyridin-3-yl]-propylamine, trifluoroacetic acid salt | | 403 (403) |
| 5-31 | 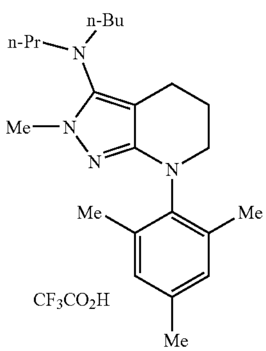 | Butyl-[2-methyl-7-(2,4,6-trimethylphenyl)-4,5,6,7-tetrahydro-2H-pyrazolo[3,4-b]pyridin-3-yl]-propylamine, trifluoroacetic acid salt | | 369 (369) |
| 5-32 | 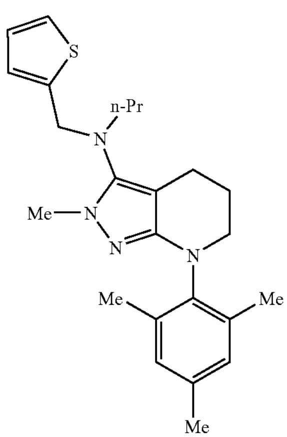 | [2-Methyl-7-(2,4,6-trimethylphenyl)-4,5,6,7-tetrahydro-2H-pyrazolo[3,4-b]pyridin-3-yl]-propylthiophen-2-ylmethylamine, trifluoroacetic acid salt | | 409 (409) |
| 5-33 | 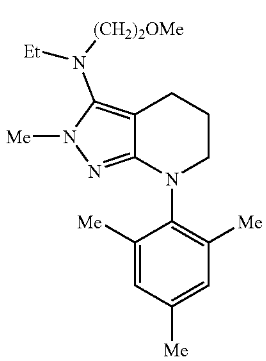 | Ethyl-(2-methoxyethyl)-[2-methyl-7-(2,4,6-trimethylphenyl)-4,5,6,7-tetrahydro-2H-pyrazolo[3,4-b]pyridin-3-yl]-amine | oil | 357 (357) |

TABLE 5-continued

| Cpd # | Structure | Name | mp (° C.) | MH+ observed (predicted) |
|---|---|---|---|---|
| 5-34 | n-Pr, Et on pyrazolo-tetrahydropyridine with mesityl; CF₃CO₂H | Ethyl-[2-methyl-7-(2,4,6-trimethylphenyl)-4,5,6,7-tetrahydro-2H-pyrazolo[3,4-b]pyridin-3-yl]-propylamine | oil | 341 (341) |
| 5-35 | N(n-Pr)₂ on pyrazolo-tetrahydropyridine with mesityl | [2-Methyl-7-(2,4,6-trimethylphenyl)-4,5,6,7-tetrahydro-2H-pyrazolo[3,4-b]pyridin-3-yl]-dipropylamine | 88.9-91.5 | 355 (355) |
| 5-36 | HNCHEt₂ on pyrazolo-tetrahydropyridine with mesityl | (1-Ethylpropyl)-[2-methyl-7-(2,4,6-trimethyl-phenyl)-4,5,6,7-tetrahydro-2H-pyrazolo[3,4-b]pyridin-3-yl]-amine | 99.3-104.9 | 341 (341) |
| 5-37 | HNCH(CH₂OMe)₂ on pyrazolo-tetrahydropyridine with mesityl | (2-Methoxy-1-methoxymethylethyl)-[2-methyl-7-(2,4,6-trimethylphenyl)-4,5,6,7-tetrahydro-2H-pyrazolo[3,4-b]pyridin-3-yl]-amine | oil | 373 (373) |

TABLE 5-continued

| Cpd # | Structure | Name | mp (° C.) | MH+ observed (predicted) |
|---|---|---|---|---|
| 5-38 | (CH₂)₂OMe / HNCHCH₂OMe on 2-methyl-7-(2,4,6-trimethylphenyl) tetrahydropyrazolo[3,4-b]pyridine core | (3-Methoxy-1-methoxymethylpropyl)-[2-methyl-7-(2,4,6-trimethylphenyl)-4,5,6,7-tetrahydro-2H-pyrazolo[3,4-b]pyridin-3-yl]-amine | oil | 387 (387) |
| 5-39 | Cyclopropylmethyl-NCH₂CH₂OMe on same core | Cyclopropylmethyl-(2-methoxyethyl)-[2-methyl-7-(2,4,6-trimethylphenyl)-4,5,6,7-tetrahydro-2H-pyrazolo[3,4-b]pyridin-3-yl]-amine | oil | 383 (383) |
| 5-40 | HNCH(Et)CH₂OMe on same core | (1-Methoxymethylpropyl)-[2-methyl-7-(2,4,6-trimethylphenyl)-4,5,6,7-tetrahydro-2H-pyrazolo[3,4-b]pyridin-3-yl]-amine | 96.5–102.5 | 357 (357) |
| 5-41 | HNCH(n-Pr)CH₂OMe on same core | (1-Methoxymethylbutyl)-[2-methyl-7-(2,4,6-trimethylphenyl)-4,5,6,7-tetrahydro-2H-pyrazolo[3,4-b]pyridin-3-yl]-amine | 100.1–104.4 | 371 (371) |

TABLE 5-continued

| Cpd # | Structure | Name | mp (° C.) | MH+ observed (predicted) |
|---|---|---|---|---|
| 5-42 | n-PrNSO₂Ph / Me-N pyrazolo[3,4-b]pyridine with 2,4,6-trimethylphenyl; CF₃CO₂H | N-[2-Methyl-7-(2,4,6-trimethylphenyl)-4,5,6,7-tetrahydro-2H-pyrazolo[3,4-b]pyridin-3-yl]-N-propylbenzenesulfonamide, trifluoroacetic acid salt | | 453 (453) |
| 5-43 | H₂N, Me-N pyrazolo[3,4-b]pyridine with 2,4-dichlorophenyl | 7-(2,4-Dichloro-phenyl)-2-methyl-4,5,6,7-tetrahydro-2H-pyrazolo[3,4-b]pyridin-3-yl amine | 176.9–178.9 | 297 (297) |
| 5-44 | H₂N, Me-N pyrazolo[3,4-b]pyridine with 2,4,6-trimethylphenyl | 2-Methyl-7-(2,4,6-trimethyl-phenyl)-4,5,6,7-tetrahydro-2H-pyrazolo[3,4-b]pyridin-3-ylamine | 208.8–210.9 | 271 (271) |
| 5-45 | H₂N, Me-N pyrazolo[3,4-b]pyridine with 2-chloro-4,6-dimethylphenyl | 7-(2-Chloro-4,6-dimethyl-phenyl)-2-methyl-4,5,6,7-tetrahydro-2H-pyrazolo[3,4-b]pyridin-3-ylamine RO4884782-000 | 234–236 | 291 (291) |

TABLE 5-continued

| Cpd # | Structure | Name | mp (° C.) | MH+ observed (predicted) |
|---|---|---|---|---|
| 5-46 | (n-Pr)₂N, Me-N, N, Cl, Cl (structure) | [7-(2,4-Dichloro-phenyl)-2-methyl-4,5,6,7-tetrahydro-2H-pyrazolo[3,4-b]pyridin-3-yl]-dipropyl-amine | | 381 (381) |
| 5-47 | Me₂N, Me-N, N, Me, Me, Me (structure) | Dimethyl-[2-methyl-7-(2,4,6-trimethyl-phenyl)-4,5,6,7-tetrahydro-2H-pyrazolo[3,4-b]pyridin-3-yl]-amine | | 299 (299) |
| 5-48 | n-PrN(CH₂)₃CN, Me-N, N, Me, Me, Me (structure) | 4-{[2-Methyl-7-(2,4,6-trimethyl-phenyl)-4,5,6,7-tetrahydro-2H-pyrazolo [3,4-b]pyridin-3-yl]-propyl-amino}-butyronitrile | 108.3-111 | 380 (380) |
| 5-49 | NHMe, Me-N, N, Me, Me, Me (structure) | Methyl-[2-methyl-7-(2,4,6-trimethyl-phenyl)-4,5,6,7-tetrahydro-2H-pyrazolo[3,4-b]pyridin-3-yl]-amine | 143.3-144.9 | 285 (285) |

TABLE 5-continued
| Cpd # | Structure | Name | mp (° C.) | MH+ observed (predicted) |
|---|---|---|---|---|
| 5-50 | 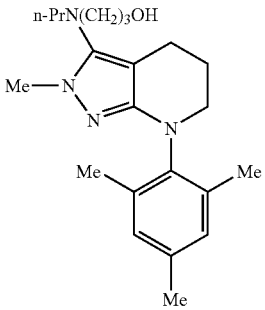 | 3-{[2-Methyl-7-(2,4,6-trimethyl-phenyl)-4,5,6,7-tetrahydro-2H-pyrazolo[3,4-b]pyridin-3-yl]-propyl-amino}-propan-1-ol | | 371 (371) |
| 5-51 | 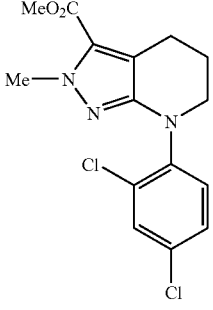 | 7-(2,4-dichlorol-phenyl)-2-methyl-4,5,6,7-tetrahydro-2H-pyrazolo[3,4-b]pyridine-3-carboxylic acid methyl ester | | 340 (340) |
| 5-52 | 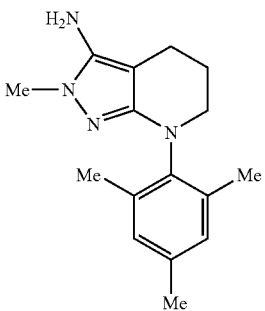 | 2-methyl-7-(2,4,6-trimethyl-phenyl)-4,5,6,7-tetrahydro-2H-pyrazolo[3,4-b]pyridin-3-ylamine | 208.8–210.9 | 271 (271) |

TABLE 5-continued

| Cpd # | Structure | Name | mp (° C.) | MH+ observed (predicted) |
|---|---|---|---|---|
| 5-53 | 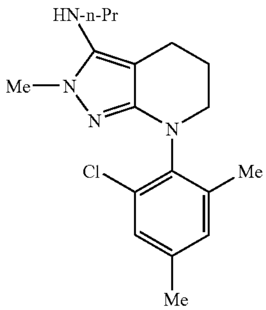 | [7-(2-chloro-4,6-dimethyl-phenyl)-2-methyl-4,5,6,7-tetrahydro-2H-pyrazolo[3,4-b]pyridin-3-yl]-propyl-amine | | 333 (333) |
| 5-54 | 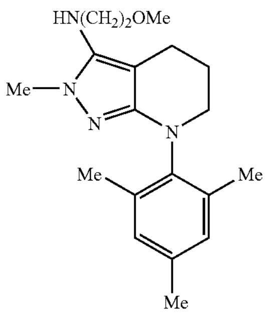 | (2-methoxy-ethyl)-[2-methyl-7-(2,4,6-trimethyl-phenyl)-4,5,6,7-tetrahydro-2H-pyrazolo [3,4-b]pyridin-3-yl]-amine | oil | 329 (329) |
| 5-55 | 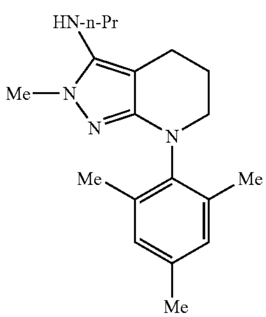 | [7-(2,4,6-trimethyl-phenyl)-2-methyl-4,5,6,7-tetrahydro-2H-pyrazolo[3,4-b]pyridin-3-yl]-propyl-amine | | 313 (313) |

Example 18

1-[2-Methyl-7-(2,4,6-trimethyl-phenyl)-4,5,6,7-tetrahydro-2H-pyrazol[3,4-b]pyridine-3-yl]ethanone O-methyl-oxime step 1

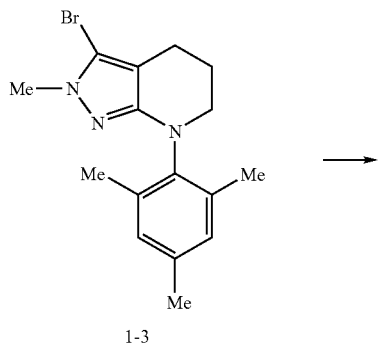

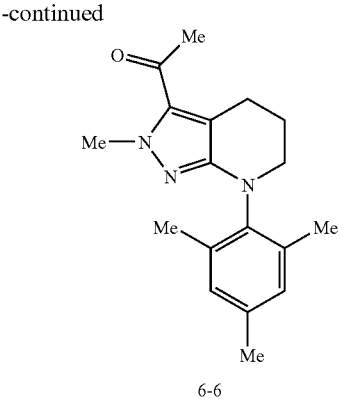

A solution of 3-bromo-2-methyl-7-(2,4,6-trimethyl-phenyl)-4,5,6,7-tetrahydro-2H-pyrazolo[3,4-b]pyridine (1-3; 0.040 g, 1.2 mmol) in 6 mL of dry THF was cooled to −78° C.

in a dry ice-acetone bath under an argon atmosphere and treated with n-butyllithium in hexane (0.83 mL, 1.32 mmol). After 10 m a solution of 1 M zinc chloride in ether (3.59 mL, 3.59 mmol) was added. The cooling bath was removed and the reaction stirred at room temperature. After 10 m acetyl chloride (0.113 g, 1.44 mmol) and tetrakis(triphenylphosphine)palladium(0) (28 mg, 0.024 mmol) were added and the brown solution was stirred for 2 hrs. The mixture was poured into 25 mL of saturated ammonium chloride solution, extracted twice with 25 mL portions of ethyl acetate. The combined organic extracts were washed with brine, dried over magnesium sulfate, and evaporated to dryness. The residue was purified on flash chromatography on silica gel eluting with ethyl acetate/hexane (15:85) giving 23 mg (6% yield) of 1-[2-methyl-7-(2,4,6-trimethyl-phenyl)-4,5,6,7-tetrahydro-2H-pyrazolo[3,4-b]pyridine-3-yl]ethanone as a colorless oil: ms $(M+H)^+=298$.

step 2

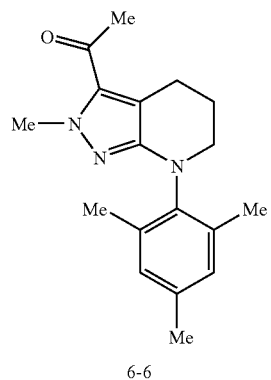

6-6

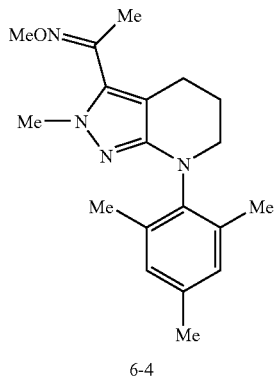

6-4

A mixture of 1-[2-methyl-7-(2,4,6-trimethyl-phenyl)-4,5,6,7-tetrahydro-2H-pyrazolo[3,4-b]pyridine-3-yl]ethanone (20 mg, 0.067 mmol), methoxylamine hydrochloride (12 mg, 0.148 mmol), and pulverized potassium carbonate (39 mg, 0.26 mmol) in 2 mL of 95% ethanol was heated at 75° C. under an atmosphere of nitrogen for 1 hr. The solvent was evaporated, the residue was treated with 50 ml of ethyl acetate, washed with brine, dried over magnesium sulfate, and evaporated to dryness. The residue was purified by flash chromatography on silica gel eluting with acetone/hexane (4:96) affording 10 mg (47% yield) of 1-[2-methyl-7-(2,4,6-trimethyl-phenyl)-4,5,6,7-tetrahydro-2H-pyrazol[3,4-b]pyridine-3-yl]ethanone O-methyl-oxime (6-4) as a brown oil: ms $(M+H)^+=327$.

Example 19

1-[2-Methyl-7-(2,4,6-trimethyl-phenyl)-4,5,6,7-tetrahydro-2H-pyrazolo[3,4-b]pyridin-3-yl]-butan-1-one

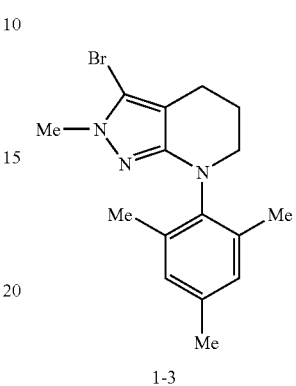

1-3

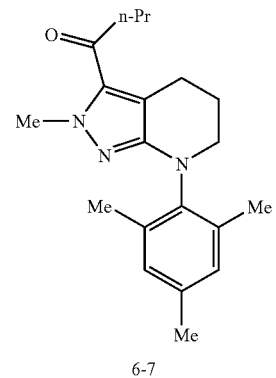

6-7

To a solution of 3-bromo-2-methyl-7-(2,4,6-trimethylphenyl)-4,5,6,7-tetrahydro-2H-pyrazolo [3,4-b]pyridine (0.053 g, 0.159 mmol) in 1 mL of tetrahydrofuran at −78° C. was added n-butyl lithium (0.12 mL, 0.19 mmol), and the yellow solution was stirred at −78° C. for 10 min. A 1.0 M zinc chloride in ether solution (0.45 mL, 0.45 mmol) was added, the resulting cloudy pale orange solution was stirred at RT for 10 min., then butyryl chloride (0.020 mL, 0.19 mmol) and tetrakis(triphenylphosphine) palladium(0) (0.003 g, 0.003 mmol) were added. The golden yellow solution was stirred for 3 h, then quenched with 1 mL of a saturated aqueous ammonium chloride solution. The mixture was partitioned between 5 mL of water and 5 mL of dichloromethane. The aqueous layer was extracted with 5 mL of dichloromethane, and the combined organic layers were dried over $MgSO_4$, filtered, and concentrated to a yellow oil. Column chromatography (0→20% EtOAc/hexanes) afforded 0.021 g (41%) of 1-[2-methyl-7-(2,4,6-trimethyl-phenyl)-4,5,6,7-tetrahydro-2H-pyrazolo[3,4-b]pyridin-3-yl]-butan-1-one as a slightly impure pale yellow oil that was used without further purification.

TABLE 6

| Cpd # | Structure | Name | mp (° C.) | MH+ observed (predicted) |
|---|---|---|---|---|
| 6-1 | 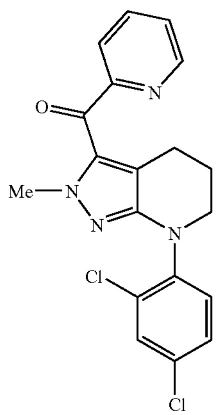 | [7-(2,4-Dichloro-phenyl)-2-methyl-4,5,6,7-tetrahydro-2H-pyrazolo[3,4-b]pyridin-2-yl]-methanone | 142.1–149.2 | 387 (387) |
| 6-2 | 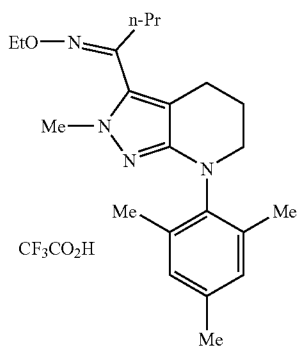 | 1-[2-Methyl-7-(2,4,6-trimethyl-phenyl)-4,5,6,7-tetrahydro-2H-pyrazolo[3,4-b] pyridin-3-yl]-butan-1-one O-ethyl-oxime; compound with trifluoro-acetic acid | | 369 (369) |
| 6-3 | 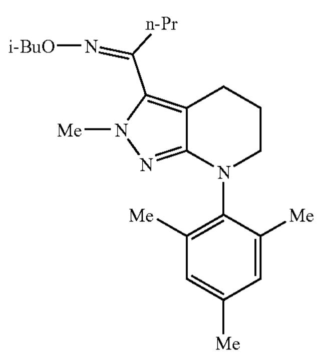 | 1-[2-Methyl-7-(2,4,6-trimethyl-phenyl)-4,5,6,7-tetrahydro-2H-pyrazolo[3,4-b]pyridin-3-yl]-butan-1-one O-isobutyl-oxime | | 397 (397) |
| 6-4 | 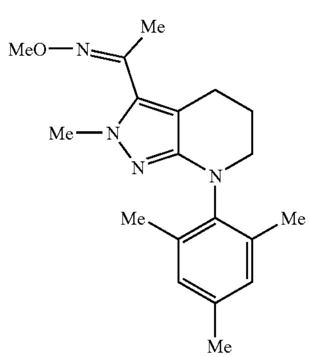 | 1-[2-Methyl-7-(2,4,6-trimethyl-phenyl)-4,5,6,7-tetrahydro-2H-pyrazolo[3,4-b] pyridin-3-yl]-ethanone O-methyl-oxime | 104.2–106.4 | 327 (327) |

TABLE 6-continued

| Cpd # | Structure | Name | mp (° C.) | MH+ observed (predicted) |
|---|---|---|---|---|
| 6-5 | 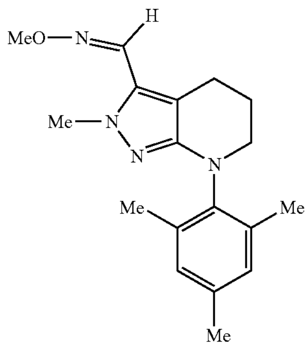 | 2-Methyl-7-(2,4,6-trimethyl-phenyl)-4,5,6,7-tetrahydro-2H-pyrazolo[3,4-b] pyridine-3-carbaldehyde O-methyl-oxime | 89–90.1 | 313 (313) |
| 6-6 | 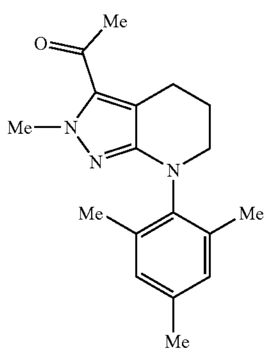 | 1-[2-Methyl-7-(2,4,6-trimethyl-phenyl)-4,5,6,7-tetrahydro-2H-pyrazolo[3,4-b]pyridin-3-yl]-ethanone | | 298 (298) |
| 6-7 | 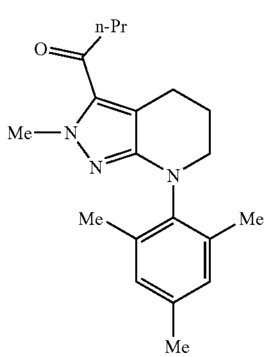 | 1-[2-Methyl-7-(2,4,6-trimethyl-phenyl)-4,5,6,7-tetrahydro-2H-pyrazolo[3,4-b]pyridin-3-yl]-butan-1-one | | 326 (326) |

Example 20

7-(2-Chloro-4,6-dimethylphenyl)-2-methyl-4,5,6,7-tetrahydro-2H-pyrazolo[3,4-b]pyridine-3-carboxylic acid cyclopropylmethylpropylamide

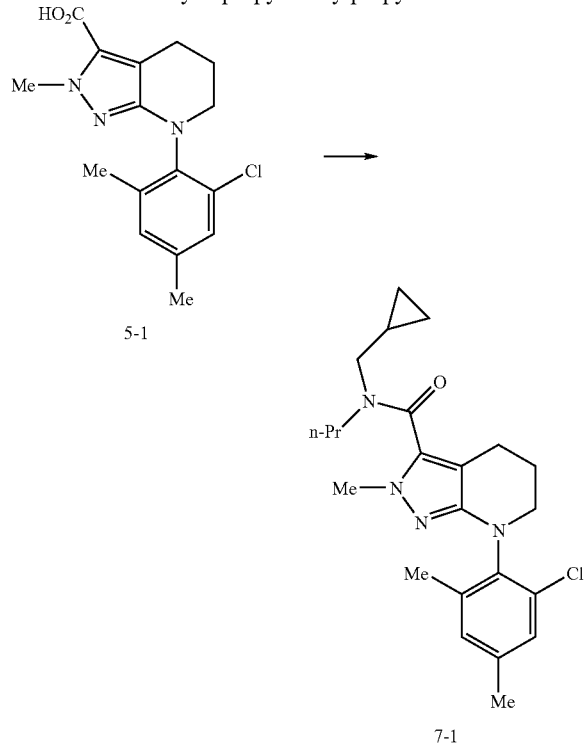

7-(2-Chloro-4,6-dimethylphenyl)-2-methyl-4,5,6,7-tetrahydro-2H-pyrazolo[3,4-b]pyridine-3-carboxylic acid (5-1; 107.0 mg), 1-hydroxybenzotriazole hydrate (50.3 mg), 1-[3-(dimethylamino)propyl]-3-ethylcarbodiimide hydrochloride (72.5 mg), triethylamine (93 μL), and N-propylcyclopropanemethylamine (49 μL) were combined in 4 mL of dichloromethane and stirred at room temperature over night. The reaction mixture was then partitioned between ethyl acetate and 1M hydrochloric acid. The ethyl acetate solution was washed with aqueous sodium bicarbonate, dried with magnesium sulfate, and concentrated. The crude product was chromatographed on silica gel eluting with an acetone/hexane gradient giving a solid which was recrystallized from hexane to afford 75.6 mg of 7-(2-chloro-4,6-dimethylphenyl)-2-methyl-4,5,6,7-tetrahydro-2H-pyrazolo[3,4-b]pyridine-3-carboxylic acid cyclopropylmethylpropylamide: mp 120.6-122.0° C.

Example 21

(3,4-Dihydro-1H-isoquinolin-2-yl)[2-methyl-7-(2,4,6-trimethylphenyl)-4,5,6,7-tetrahydro-2H-pyrazolo[3,4-b]pyridin-3-yl]methanone

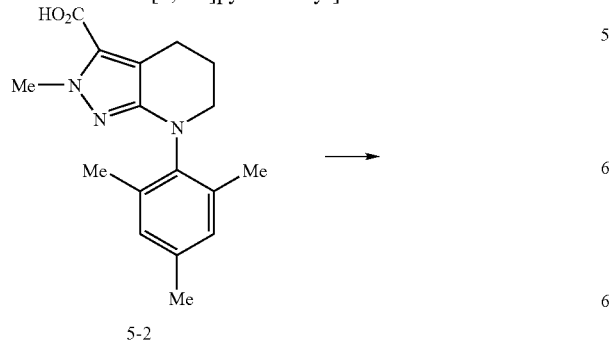

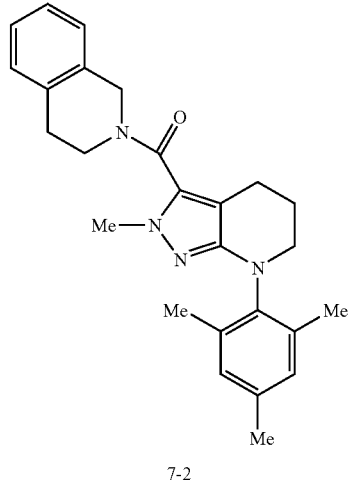

A suspension of 125 mg of 2-methyl-7-(2,4,6-trimethylphenyl)-4,5,6,7-tetrahydro-2H-pyrazolo[3,4-b]pyridine-3-carboxylic acid (5-2) in 5 mL of dichloromethane was treated with 116 μL of triethylamine, 56 mg of 1-hydroxybenzotriazole hydrate, 88 mg of 1-[3-(dimethylamino)propyl]-3-ethylcarbodiimide hydrochloride, and 52 μL of 1,2,3,4-tetrahydroisoquinoline and stirred under an atmosphere of nitrogen at room temperature for 20 h. The mixture was diluted with 50 mL of ethyl acetate, washed with 30 mL of 0.5M HCl, washed with 30 mL of saturated sodium bicarbonate solution, dried over magnesium sulfate, and evaporated to dryness yielding 149 mg of (3,4-dihydro-1H-isoquinolin-2-yl)[2-methyl-7-(2,4,6-trimethylphenyl)-4,5,6,7-tetrahydro-2H-pyrazolo[3,4-b]pyridin-3-yl]methanone: mp 80.3-87.7° C.

Compound 7-3 was prepared by acylation of 2-methyl-7-(2,4,6-trimethylphenyl)-4,5,6,7-tetrahydro-2H-pyrazolo[3,4-b]pyridine-3-ylamine (5-52) with propionyl chloride.

Compound 7-4 was prepared by acylation of 5-52 with methoxyacetyl chloride.

Example 22

2-[2-Methyl-7-(2,4,6-trimethylphenyl)-4,5,6,7-tetrahydro-2H-pyrazolo[3,4-b]pyridin-3-ylmethyl]-1,2,3,4-tetrahydroisoquinoline dihydrochloride

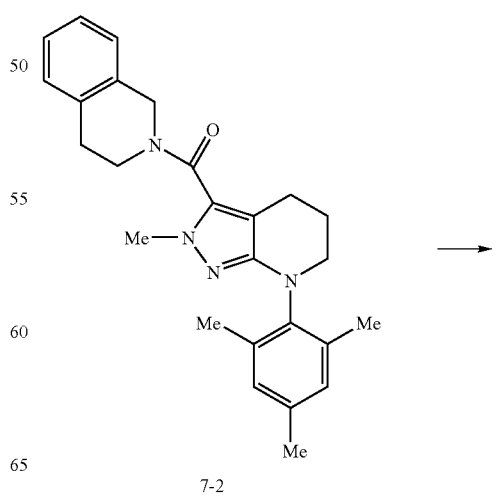

-continued

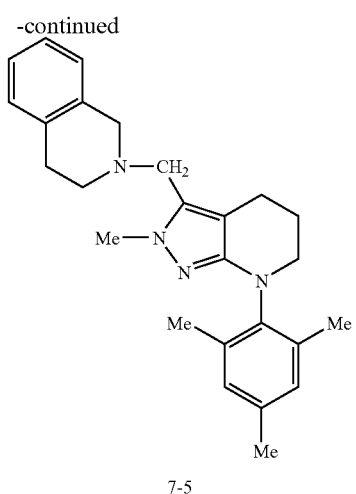

7-5

A solution of 140 mg of (3,4-dihydro-1H-isoquinolin-2-yl)[2-methyl-7-(2,4,6-trimethylphenyl)-4,5,6,7-tetrahydro-2H-pyrazolo[3,4-b]pyridin-3-yl]methanone in 6 mL of dry tetrahydrofuran was treated with 4 mL of 1M borane-tetrahydrofuran complex in tetrahydrofuran and stirred under an atmosphere of nitrogen at room temperature for 15 h. The mixture was slowly treated with 5 mL of concentrated HCl and heated at 45° C. for 5 h. The mixture was then cooled to room temperature and made alkaline by the cautious addition of solid sodium bicarbonate. After diluting with water, the mixture was washed twice with 30 mL portions of ethyl acetate. The combined organic extracts were washed with 30 mL of brine, dried over magnesium sulfate, and evaporated to dryness. The residue was purified on a flash silica gel column eluting with 10% acetone/hexane solvent yielding 47 mg of the free base. The dihydrochloride salt was prepared using 1M HCl in ether giving 49 mg of 2-[2-methyl-7-(2,4,6-trimethylphenyl)-4,5,6,7-tetrahydro-2H-pyrazolo[3,4-b]pyridin-3-ylmethyl]-1,2,3,4-tetrahydroisoquinoline dihydrochloride: mp 236.4-241° C.

TABLE 7

| Cpd # | Structure | Name | mp (° C.) | MH+ observed (predicted) |
|---|---|---|---|---|
| 7-1 | 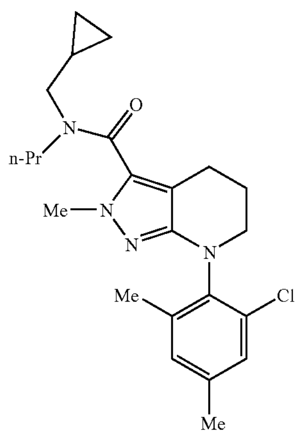 | 7-(2-Chloro-4,6-dimethylphenyl)-2-methyl-4,5,6,7-tetrahydro-2H-pyrazolo[3,4-b]pyridine-3-carboxylic acid cyclopropylmethylpropyl amide | 120.6–122.0 | 415 (415) |
| 7-2 | 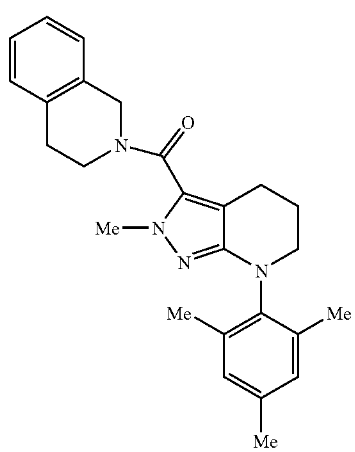 | (3,4-Dihydro-1H-isoquinolin-2-yl)-[2-methyl-7-(2,4,6-trimethyl-phenyl)-4,5,6,7-tetrahydro-2H-pyrazolo[3,4-b]pyridin-3-yl]-methanone | 80.3–87.7 | 415 (415) |

TABLE 7-continued

| Cpd # | Structure | Name | mp (° C.) | MH+ observed (predicted) |
|---|---|---|---|---|
| 7-3 | EtCONH, Me-N pyrazolo[3,4-b]pyridine with 2,4,6-trimethylphenyl | N-[2-Methyl-7-(2,4,6-trimethylphenyl)-4,5,6,7-tetrahydro-2H-pyrazolo[3,4-b]pyridin-3-yl]propionamide | 226–228 | 327 (327) |
| 7-4 | MeOCH₂CONH, Me-N pyrazolo[3,4-b]pyridine with 2,4,6-trimethylphenyl | 2-Methoxy-N-[2-methyl-7-(2,4,6-trimethyl-phenyl)-4,5,6,7-tetrahydro-2H-pyrazolo[3,4-b]pyridin-3-yl]acetamide | 133.8–135.0 | 343 (343) |
| 7-5 | tetrahydroisoquinoline-CH₂-pyrazolo[3,4-b]pyridine with 2,4,6-trimethylphenyl (HCl)₂ | 2-[2-Methyl-7-(2,4,6-trimethyl-phenyl)-4,5,6,7-tetrahydro-2H-pyrazolo[3,4-b]pyridin-3-ylmethyl]-1,2,3,4-tetetrahydroisoquinoline dihydrochloride | 236.4–241.0 | 401 (401) |

Example 23

7-(2-Chloro-4,6-dimethylphenyl)-2-methyl-3-(1-propylbutoxy)-4,5,6,7-tetrahydro-2H-pyrazolo[3,4-b]pyridine

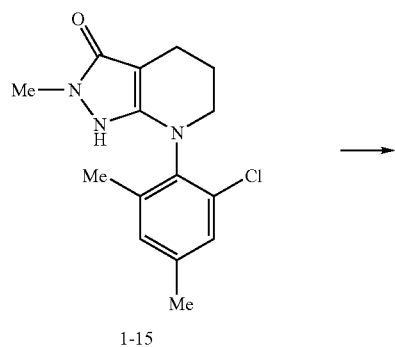

1-15

-continued

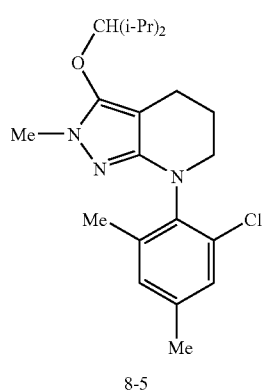

8-5

A mixture of 200 mg of 7-(2-chloro-4,6-dimethylphenyl)-2-methyl-1,2,4,5,6,7-hexahydro-pyrazolo[3,4-b]pyridin-3-one (Example 1, step 5) and 337 mg of triphenylphosphine in 15 mL of dry tetrahydrofuran was treated with 124 mg of 4-heptanol and 224 mg of diethylazodicarboxylate. The mixture was stirred under an atmosphere of nitrogen at room temperature for 16 h. The solvent was evaporated and the residue was purified by flash column chromatography on silica gel eluting with 15% ethyl acetate/hexane to afford 84 mg of 7-(2-chloro-4,6-dimethylphenyl)-2-methyl-3-(1-propylbutoxy)-4,5,6,7-tetrahydro-2H-pyrazolo[3,4-b]pyridine as a colorless oil: ms (MH$^+$)=390.

Compound 8-2 was prepared according to Example 23 except 7-(2-Chloro-4,6-dimethylphenyl)-2-methyl-1,2,4,5,6,7-hexahydropyrazolo-[3,4-b]pyridin-3-one was replaced with compound 1-13.

Compound 8-3 was prepared according to the procedure described in Example 23, except that 7-(2-chloro-4,6-dimethylphenyl)-2-methyl-1,2,4,5,6,7-hexahydropyrazolo[3,4-b]pyridin-3-one was replaced by 7-(4-methoxy-2-methyl-phenyl)-2-methyl-1,2,4,5,6,7-hexahydro-pyrazolo[3,4-b]pyridin-3-one.

Compound 8-4 was prepared according to the procedure described in Example 23, except that 7-(2-chloro-4,6-dimethylphenyl)-2-methyl-1,2,4,5,6,7-hexahydropyrazolo[3,4-b]pyridin-3-one was replaced by replaced by 7-(6-dimethylamino-4-methylpyridin-3-yl)-2-methyl-1,2,4,5,6,7-hexahydropyrazolo[3,4-b]pyridin-3-one.

TABLE 8

| Cpd # | Structure | Name | mp (° C.) | MH+ observed (predicted) |
|---|---|---|---|---|
| 8-1 | 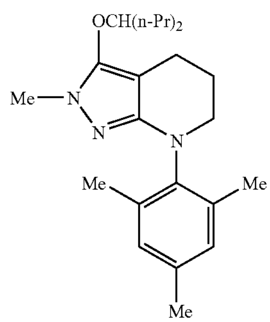 | 7-(2-Chloro-4,6-dimethylphenyl)-2-methyl-3-(1-propylbutoxy)-4,5,6,7-tetrahydro-2H-pyrazolo[3,4-b]pyridine | oil | 390 (390) |
| 8-2 | 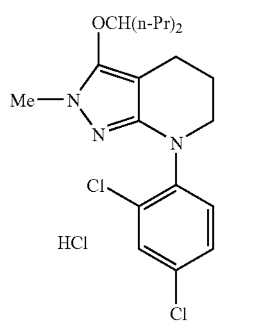 | 7-(2,4-Dichlorophenyl)-2-methyl-3-(1-propylbutoxy)-4,5,6,7-tetrahydro-2H-pyrazolo[3,4-b]pyridine hydrochloride | oil | 396 (396) |
| 8-3 | 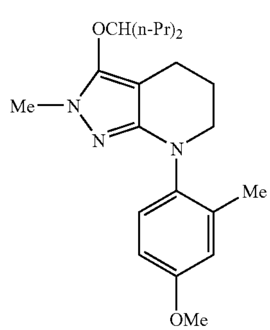 | 7-(4-Methoxy-2-methylphenyl)-2-methyl-3-(1-propylbutoxy)-4,5,6,7-tetrahydro-2H-pyrazolo[3,4-b]pyridine | oil | 372 (372) |

TABLE 8-continued

| Cpd # | Structure | Name | mp (° C.) | MH+ observed (predicted) |
|---|---|---|---|---|
| 8-4 | ![structure] | Dimethyl-{4-methyl-5-[2-methyl-3-(1-propylbutoxy)-2,4,5,6-tetrahydro-pyrazolo[3,4-b]pyridin-7-yl]-pyridin-2-yl}-amine | oil | 386 (386) |
| 8-5 | ![structure] | 7-(2-chloro-4,6-dimethylphenyl)-2-methyl-3-(1-propylbutoxy)-4,5,6,7-tetrahydro-2H-pyrazolo[3,4-b]pyridine | | 390-(390) |

Example 24

2-Methyl-3-(2-trifluoromethylphenyl)-7-(2,4,6-trimethylphenyl)-4,5,6,7-tetrahydro-2H-pyrazolo[3,4-b]pyridine

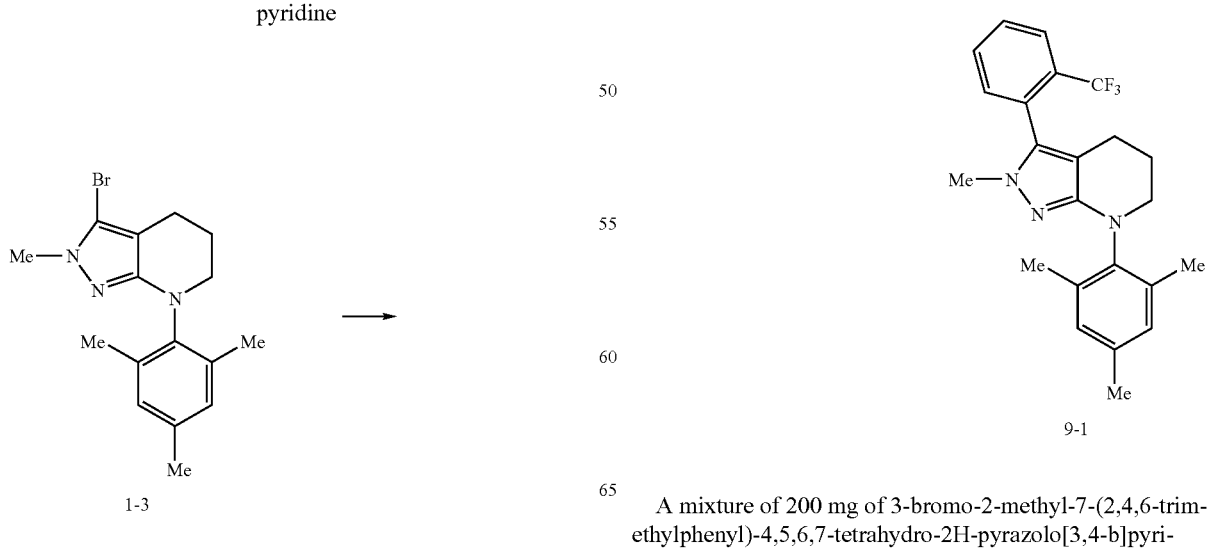

A mixture of 200 mg of 3-bromo-2-methyl-7-(2,4,6-trimethylphenyl)-4,5,6,7-tetrahydro-2H-pyrazolo[3,4-b]pyridine, 124 mg of 2-trifluoromethylphenylboronic acid, and 14 mg of tetrakistriphenylphosphine palladium (0) in 2 mL of dioxane was treated with a solution of 210 mg of sodium carbonate in 2 mL of water. The mixture was placed under an atmosphere of argon and heated to 100° C. for 20 h. The mixture was cooled to room temperature, diluted with 20 mL of ethyl acetate, washed with 20 mL of 1 M HCl and 20 mL of brine, dried over magnesium sulfate, and evaporated to dryness. The residue was purified by flash silica gel column chromatography using 7% acetone/hexane as solvent yielding 87 mg of 2-methyl-3-(2-trifluoromethylphenyl)-7-(2,4,6-trimethylphenyl)-4,5,6,7-tetrahydro-2H-pyrazolo[3,4-b]pyridine, mp 59-63° C.

Compound 9-6 was prepared according to the procedure described in Example 24, except that 2-trifluoromethylphenylboronic acid was replaced by 2,6-bismethoxyphenylboronic acid.

EXAMPLE 25

3-Bromo-2-methyl-7-(2,4,6-trimethyl-phenyl)-2,4,5,7-tetrahydro-pyrazolo[3,4-b]pyridin-6-one

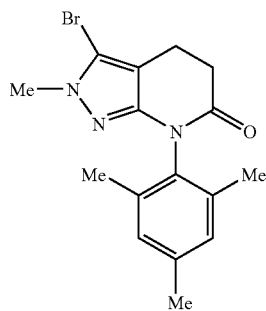

(9-4)

Ruthenium(IV) oxide hydrate (22 mg) was dissolved in 35 mL water and sodium periodate (684 mg) was added. This mixture was rapidly stirred while 3-bromo-2-methyl-7-(2,4,6-trimethyl-phenyl)-4,5,6,7-tetrahydro-2H-pyrazolo[3,4-b]pyridine (1-3; 505 mg) in 25 mL carbon tetrachloride was added dropwise. After the mixture had stirred at room temperature over night, isopropanol was added and the mixture was stirred for an additional hour. The mixture was then filtered through diatomaceous earth and extracted with dichloromethane. The organic extracts were dried with magnesium sulfate and concentrated. The residue was chromatographed on silica gel to afford 54.4 mg of 3-bromo-2-methyl-7-(2,4,6-trimethylphenyl)-2,4,5,7-tetrahydro-pyrazolo[3,4-b]pyridin-6-one (9-4).

EXAMPLE 26

2-Methyl-7-(2,4,6,-trimethylphenyl)-2,5,6,7-tetrahydropyrazole[4,3-b][1,4]oxazine

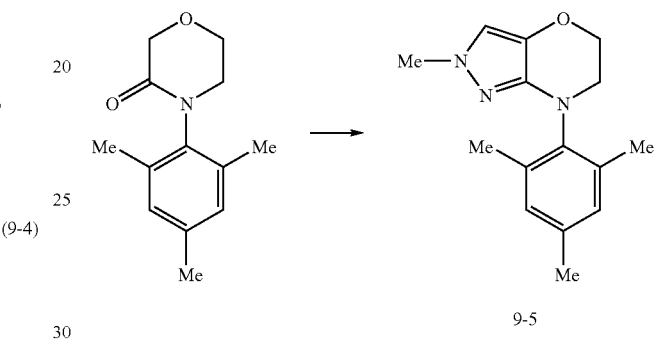

9-5

To a solution of 4-(2,4,6-trimethylphenyl)-morpholin-3-one (4.96 g, 23 mmol) in DMF (17 mL) was added $POCl_3$ (5 mL) and the solution was stirred for 2.5 hours. Excess $POCl_3$ was removed under vacuum, methylhydrazine (5 mL) was added, and the resultant mixture was stirred for 2 hours. The reaction mixture was dissolved in methylene chloride and washed with water. The organic solution was dried ($Na_2SO_4$), concentrated, and the residue chromatographed on silica gel, eluting with 9:1 toluene/ethyl acetate, to give 672 mg of 2-methyl-7-(2,4,6,-trimethylphenyl)-2,5,6,7-tetrahydropyrazole[4,3-b][1,4]oxazine as an off-white solid, mp 103.6-104.8° C.

TABLE 9

| Cpd # | Structure | Name | mp (° C.) | MH+ observed (predicted) |
|---|---|---|---|---|
| 9-1 | 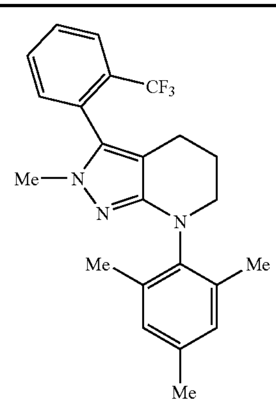 | 2-Methyl-3-(2-trifluoromethyl-phenyl)-7-(2,4,6-trimethyl-phenyl)-4,5,6,7-tetrahydro-2H-pyrazolo[3,4-b]pyridine | 59–63 | 400 (400) |

TABLE 9-continued

| Cpd # | Structure | Name | mp (° C.) | MH+ observed (predicted) |
|---|---|---|---|---|
| 9-2 | 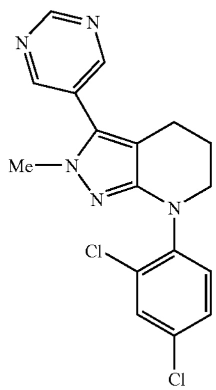 | 7-(2,4-Dichloro-phenyl)-2-methyl-3-pyrimidin-5-yl-4,5,6,7-tetrahydro-2H-pyrazolo[3,4-b]pyridine | 164.2–166.8 | 360 (360) |
| 9-3 | 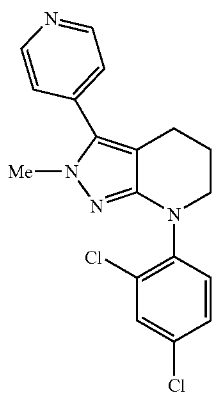 | 7-(2,4-Dichloro-phenyl)-2-methyl-3-pyridin-4-yl-4,5,6,7-tetrahydro-2H-pyrazolo[3,4-b]pyridine | 123.5–125.5 | 359 (359) |
| 9-4 | 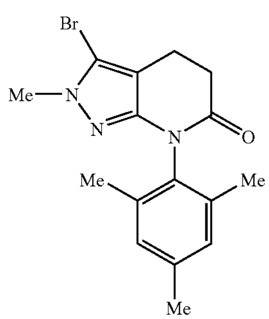 | 3-Bromo-2-methyl-7-(2,4,6-trimethyl-phenyl)-2,4,5,7-tetrahydro-pyrazolo[3,4-b]pyridin-6-one | 256.8–258.0 | 348 (348) |
| 9-5 | 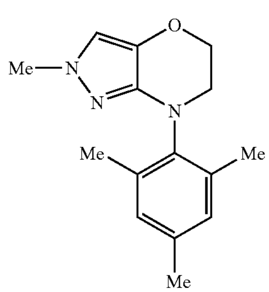 | 2-Methyl-7-(2,4,6-trimethyl-phenyl)-2,5,6,7-tetrahydro-pyrazolo[4,3-b][1,4]oxazine | 103.6–104.8 | 258 (258) |

TABLE 9-continued

| Cpd # | Structure | Name | mp (° C.) | MH+ observed (predicted) |
|---|---|---|---|---|
| 9-6 | 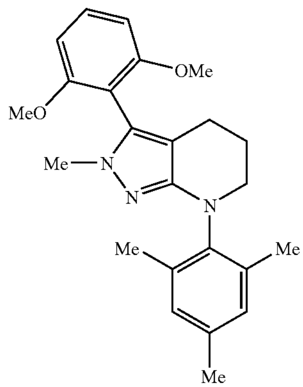 | 3-(2,6-Dimethoxy-phenyl)-2-methyl-7-(2,4,6-trimethyl-phenyl)-4,5,6,7-tetrahydro-2H-pyrazolo[3,5-b]pyridine | 169.9–172.8 | 392 (392) |

EXAMPLE 27

35S-TBPS Binding Assay

The binding assay is based on the assay reported by K. Gee et al., *Eur. J. Pharmacol.* 1987 136:419-423.

Homogenate preparation: Membrane preparations of HEK293 cells containing either $GABA_A$ $\alpha_1\beta_2\gamma_2$ or $GABA_A$ $\alpha_2\beta_3\gamma_2$ constructs were performed according to a modified procedure previously described by Gee et al. (supra). Whole HEK 293 cells in D-PBS (calcium/magnesium free) buffer adjusted to pH 7.4 were centrifuged at 7,280×g for 20 m. After discarding the supernatant, the pellet was resuspended in the buffer and centrifuged at 1,820×g for 10 m. Afterwards, the supernatant was discarded and the pellet resuspended in ice-cold preparation buffer (50 mM Tris HCl pH 7.4, 4° C. and 150 mM KCl), homogenized for 30 sec using a Brinkmann Polytron PT3000 (setting 6) and centrifuged at 48,000×g for 30 m at 4° C. The centrifugation and homogenization procedure was repeated two more times for a total of 3 times before resuspending the membranes at a final protein concentration of 0.5 mg/mL. Aliquots (30 mL) of the final membrane preparation were then centrifuged at 48,000×g for 30 m, and the resulting pellets were stored at −80° C. until required.

35S-TBPS binding assay. Membrane pellets containing either $GABA_A$ $\alpha_1\beta_2\gamma_2$ or $GABA_A$ $\alpha_2\beta_3\gamma_2$ constructs were thawed on ice, resuspended in 10 mL of 50 mM Tris HCl pH 7.4, 4° C. and 150 mM KCl and centrifuged at 48,000×g, 30 m at 4° C. After discarding the supernatant, the pellet was resuspended in 30 mL incubation buffer (50 mM Tris HCl pH 7.4, 25° C. and 150 mM KCl) at approximately 0.5 mg/mL protein concentration. In $^{35}$S-TBPS competition studies, HEK293 membranes were incubated with $^{35}$S-TBPS (5 nM final) and GABA (1 µM) in the absence or presence of competitor at concentrations ranging from 0.01 nM to 10 µM in 125 µL incubation buffer for 2 hours at room temperature (~22° C.). Non-specific binding was assayed with picrotoxin (100 µM final concentration). The binding reaction was terminated by vacuum filtration through GF/B filters previously soaked in 0.1% polyethylenimine followed by 3×1 mL washes with ice cold wash buffer (50 mM Tris HCl pH7.4, 4° C. and 150 mM KCl). Measurement of bound radioactivity was performed using a Packard Microplate 96 well topcount scintillation counter. Analysis of competition curves and estimation of $pIC_{50}$ values of test compounds were performed using the software programs ActivityBase and/or Prism (version 3.0).

| | $pIC_{50}$ | |
|---|---|---|
| compound | $\alpha_1\beta_2\gamma_2$ | $\alpha_2\beta_3\gamma_2$ |
| 2-17 | 5.547 | 6.978 |
| 3-10 | 5.423 | 6.883 |
| 1-9 | 5.921 | 7.016 |

EXAMPLE 28

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various modifications may be made to adapt a particular situation, compound, composition, process, process step or steps, to the objective spirit and scope of the present invention as defined in the claims. Such modifications may be made without departing from the true spirit and scope of the invention which should be determined with reference to the following claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I:

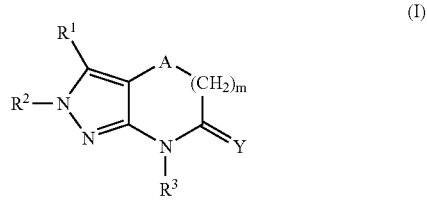

wherein:

$R^1$ is $CHR^f R^g$, $C_{2-10}$ alkynyl, $C_{1-6}$ haloalkyl, cyano, $-(CH_2)_oS(O)_nR^i$, $-(CH_2)_oS(O)_2NR^j_2$, $-NR^f SO_2R^i$, $-C(=Z)R^j$; tetrazolyl $C_{0-3}$ alkylene IIa or IIb, or $C_{1-10}$ alkyl wherein 2 to 3 nonadjacent carbon atoms in the alkyl chain are replaced with $-O-$, $-S-$ or $-NR^f-$ with the proviso that when $R^1$ is $NR^f SO_2R^i$, $R^i$ is not optionally substituted phenyl;

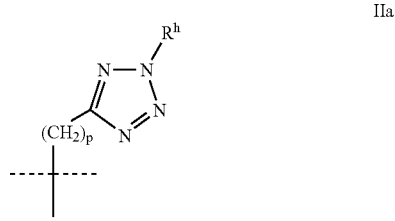

-continued

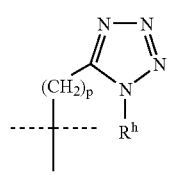
IIb $R^2$ is hydrogen, $C_{1-6}$ alkyl, $C_{3-6}$ cycloalkyl, $C_{3-6}$ cycloalkyl-$C_{1-3}$ alkyl, $C_{1-3}$ alkoxycarbonyl-$C_{1-3}$ alkyl; $C_{1-6}$ haloalkyl;

$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, $C_{1-3}$ monoalkylaminosulfonyl, $C_{1-3}$ dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl;

$R^f$ is hydrogen or $C_{1-10}$ alkyl;

$R^g$ is $C_{2-10}$ alkenyl;

$R^h$ is H or $C_{1-3}$ alkyl;

$R^i$ is $C_{1-6}$ alkyl, $C_{2-6}$ alkenyl, $C_{1-6}$ heteroalkyl or phenyl optionally substituted with one or more substituents independently selected from the group consisting of $C_{1-6}$ alkyl, $C_{1-6}$ haloalkyl, $C_{1-6}$ alkoxy, amino, $C_{1-3}$ alkylamino, $C_{1-3}$ dialkylamino, hydroxyl-$C_{1-6}$ alkyl, cyano, acylamino, $C_{1-3}$ alkylsulfonyl, $C_{1-3}$ alkylsulfonyloxy, and halogen;

$R^j$ is hydrogen, $C_{1-6}$ alkyl, $C_{2-6}$ alkenyl, or $C_{1-6}$ heteroalkyl;

A is $CH_2$;

Y is O or H,H;

Z is O or $NOR^f$;

m is 1;

n is 0 to 2;

o is 0 to 6;

p is 0 to 3;

and racemic or non-racemic mixtures of isomers or pharmaceutically acceptable salts thereof.

2. The compound of claim 1 wherein $R^1$ is $CHR^fR^g$, $C_{2-10}$ alkynyl, $(CH_2)_oS(O)_nR^i$, $(CH_2)_oS(O)_2NR^j_2$, —$NR^fSO_2R^i$, $C_{1-6}$ haloalkyl or tetrazolyl $C_{0-3}$ alkylene IIa or IIb; $R^i$ is $C_{1-6}$ alkyl, $R^2$ is hydrogen or $C_{1-6}$ alkyl; $R^3$ is optionally substituted aryl; A is $CH_2$; and Y is H,H.

3. The compound of claim 2 wherein $R^1$ is $(CH_2)_oS(O)_nR^i$, $(CH_2)_oS(O)_2NR^j_2$, —$NR^fSO_2R^i$; $R^2$ is methyl or ethyl; n is 2 and o is 0.

4. The compound according to claim 2 wherein $R^1$ is ethynyl and $R^2$ is methyl or ethyl.

5. The compound according to claim 2 wherein $R^1$ is tetrazolyl $C_{0-3}$ alkylene IIa; $R^2$ is methyl or ethyl.

6. The compound according to claim 2 wherein $R^1$ is tetrazolyl $C_{0-3}$ alkylene IIb; $R^2$ is methyl or ethyl.

7. A pharmaceutical comprising a therapeutically effective amount of a compound according to formula I

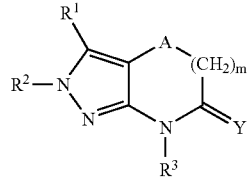
(I)

wherein:

$R^1$ is —$OR^a$, —$NR^aR^b$, —$CR^cR^dR^e$, $CHR^fR^g$, $CO_2R^a$, —$C(O)NR^aR^b$; cyano, hydrogen, $C_{2-10}$ alkynyl, $C_{1-6}$ haloalkyl, halogen, —$(CH_2)_oS(O)_nR^i$, —$(CH_2)_oS(O)_2NR^j_2$, —$NR^fSO_2R^i$, —$C(=Z)R^j$, tetrazolyl $C_{0-3}$ alkylene IIa or IIb, cycloalkenyl, aryl, or heteroaryl, where

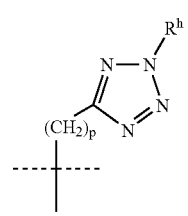
IIa

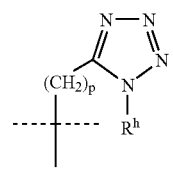
IIb each aryl or heteroaryl is optionally substituted with one or more substituents independently selected from $C_{1-6}$alkyl, $C_{1-6}$alkoxy, $C_{1-6}$alkylthio, $C_{1-6}$alkylsulfonyl, halogen, haloalkyl, cyano, nitro, —$C(O)NR^{a'}R^{b'}$, and —$NR^{a'}R^{b'}$, where $R^{a'}$ and $R^{b'}$ are each independently selected from the group consisting of hydrogen, $C_{1-9}$alkyl, and $C_{1-9}$alkylcarbonyl, or $R^1$ is $C_{1-10}$ alkyl wherein 2 to 3 nonadjacent carbon atoms in the alkyl chain optionally can be replaced with —O—, —S— or —$NR^f$ with the proviso that when $R^1$ is $NR^fSO_2R^i$, $R^i$ is not optionally substituted phenyl;

$R^2$ is hydrogen, $C_{1-6}$alkyl, $C_{3-6}$cycloalkyl, $C_{3-6}$cycloalkylalkyl, $C_{1-6}$alkylcarbonyl, $C_{1-6}$alkylsulfonyl, aryl, or arylalkyl, wherein said aryl or arylalkyl is optionally substituted with one or more substituents independently selected from $C_{1-6}$alkyl, $C_{1-6}$haloalkyl, $C_{1-6}$alkoxy, and halogen;

$R^3$ is aryl or heteroaryl, each optionally substituted with one or more substituents independently selected from the group consisting of $C_{1-6}$alkyl, $C_{1-6}$alkoxy, $C_{1-6}$alkylthio, $C_{1-6}$alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$alkyl, and $C_{1-9}$alkylcarbonyl;

$R^a$ and $R^b$ are each independently selected from the group consisting of hydrogen, $C_{1-9}$alkyl, hydroxyalkyl, $C_{1-6}$alkoxyalkyl, $C_{1-6}$alkylthioalkyl, carboxyalkyl, $C_{1-6}$-alkoxycarbonyl, $C_{1-6}$-alkoxy$C_{1-3}$-alkylcarbonyl, acyl, $C_{3-6}$cycloalkyl, $C_{3-6}$cycloalkylalkyl, di-$C_{3-6}$cycloalkyl$C_{1-3}$alkyl, $C_{1-6}$heteroalkyl, aminoalkyl, aminocarbonylalkyl, cyanoalkyl, $C_{5-8}$heterocyclyl, heterocyclylalkyl, aryl, arylalkyl, heteroaryl, heteroarylalkyl, phenylalkyl, diphenylalkyl, phenylsulfonyl optionally substituted as described for phenyl below, and $C_{1-3}$alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$ alkyl, $C_{1-6}$ haloalkyl, $C_{1-6}$ alkoxy, amino, $C_{1-3}$ alkylamino, $C_{1-3}$ dialkylamino, hydroxyl-$C_{1-6}$ alkyl, cyano, acylamino, $C_{1-6}$ alkylsulfonyl, alkyl $C_{1-6}$ sulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, $C_{1-6}$ haloalkyl, $C_{1-6}$alkoxy, $C_{1-3}$ amino, $C_{1-3}$ alkylamino, $C_{1-3}$ dialkylamino, and halogen, and each of said amino groups is optionally monosubstituted or disubstituted with alkyl, or is contained in a pyrrolidinyl, piperidinyl, morpholinyl, or piperazinyl group;

$R^c$ is hydrogen, hydroxy, $C_{1-6}$alkoxy, or —$NR^{a'''}R^{b'''}$;

$R^d$ and $R^e$ are each independently selected from the group consisting of hydrogen, $C_{1-9}$ alkyl, hydroxy $C_{1-6}$ alkyl, $C_{1-6}$ alkoxy $C_{1-3}$ alkyl, $C_{1-6}$ alkylthioalkyl, $C_{1-6}$ heteroalkyl, heterocyclyl, heterocyclyl $C_{1-3}$ alkyl, $C_{3-6}$ cycloalkyl, $C_{3-6}$ cycloalkyl $C_{1-3}$ alkyl, di-$C_{3-6}$ cycloalkyl-$C_{1-3}$ alkyl, aryl, aryl $C_{1-3}$ alkyl, heteroaryl, heteroaryl $C_{1-3}$ alkyl, phenyl $C_{1-3}$ alkyl, diphenyl-$C_{1-3}$ alkyl, and $C_{1-3}$ alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$ alkyl, $C_{1-6}$ haloalkyl, $C_{1-6}$ alkoxy, amino, $C_{1-3}$ alkylamino, $C_{1-3}$ dialkylamino, and halogen; or $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$cycloalkyl-$C_{1-3}$ alkylidenyl, $C_{3-6}$ cycloalkyl-$C_{1-3}$ alkyl-$C_{1-3}$ alkylidenyl, $C_{3-6}$ heterocyclylidenyl, $C_{3-6}$ heterocyclyl-$C_{1-3}$ alkylidenyl, $C_{3-6}$ heterocyclyl-$C_{1-3}$ alkyl-$C_{1-3}$ alkylidenyl, aryl-$C_{1-3}$ alkylidenyl, aryl-$C_{1-3}$ alkyl-$C_{1-3}$ alkylidenyl, heteroaryl-$C_{1-3}$ alkylidenyl, and heteroaryl-$C_{1-3}$ alkyl-$C_{1-3}$ alkylidenyl, wherein each of said cycloalkyl, aryl, or heteroaryl groups is optionally substituted with one or more substituents independently selected from $C_{1-6}$ alkyl, $C_{1-6}$ haloalkyl, $C_{1-6}$ alkoxy, amino, $C_{1-3}$ alkylamino, $C_{1-3}$ dialkylamino, and halogen; or $R^d$ and $R^e$ are taken together with the carbon to which they are attached to form a $C_{3-7}$ cycloalkyl or heterocyclyl ring;

$R^f$ is hydrogen or $C_{1-10}$ alkyl;

$R^g$ is $C_{2-10}$ alkenyl;

$R^h$ is H or $C_{1-3}$ alkyl;

$R^i$ is $C_{1-6}$ alkyl, $C_{2-6}$ alkenyl, $C_{1-6}$ heteroalkyl or phenyl optionally substituted with one or more substituents independently selected from the group consisting of $C_{1-6}$ alkyl, $C_{1-6}$ haloalkyl, $C_{1-6}$ alkoxy, amino, $C_{1-3}$ alkylamino, $C_{1-3}$ dialkylamino, hydroxyl-$C_{1-6}$alkyl, cyano, acylamino, $C_{1-6}$ alkylsulfonyl, $C_{1-6}$ alkylsulfonyloxy, and halogen;

$R^j$ is hydrogen, $C_{1-6}$ alkyl, $C_{2-6}$ alkenyl, or $C_{1-6}$ heteroalkyl;

A is $CH_2$;

Y is O or H,H;

Z is O or $NOR^f$;

$R^{a'''}$ and $R^{b'''}$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, $C_{1-6}$-alkoxycarbonyl, $C_{1-6}$-alkoxy-$C_{1-3}$-alkylcarbonyl, acyl, $C_{3-6}$ cycloalkyl, $C_{3-6}$ cycloalkylalkyl, di-$C_{3-6}$ cycloalkyl-$C_{1-3}$ alkyl, $C_{1-6}$ heteroalkyl, $C_{1-3}$ aminoalkyl, aminocarbonyl $C_{1-3}$ alkyl, cyano $C_{1-3}$ alkyl, $C_{5-8}$heterocyclyl, heterocyclyl-$C_{1-3}$ alkyl, aryl, aryl-$C_{1-3}$ alkyl, heteroaryl, heteroaryl-$C_{1-3}$ alkyl, phenyl-$C_{1-3}$ alkyl, diphenyl-$C_{1-3}$ alkyl, and $C_{1-3}$ alkyl substituted with both a $C_{3-6}$cycloalkyl and a phenyl group, wherein each of said cycloalkyl, phenyl, aryl, or heteroaryl groups is optionally substituted with one or more substituents independently selected from the group consisting of $C_{1-6}$ alkyl, $C_{1-6}$ haloalkyl, $C_{1-6}$ alkoxy, amino, $C_{1-3}$ alkylamino, $C_{1-3}$ dialkylamino, hydroxy $C_{1-3}$ alkyl, cyano, acylamino, $C_{1-3}$ alkylsulfonyl, $C_{1-3}$alkylsulfonyloxy, and halogen, and each of said amino groups is optionally monosubstituted or disubstituted with $C_{1-3}$ alkyl; or $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

m is 1;

n is 0 to 2;

o is 0 to 6;

p is 0 to 3;

or individual isomers, racemic or non-racemic mixtures of isomers, or pharmaceutically acceptable salts thereof admixed with at least one diluent, excipient or carrier and wherein said disorder is selected from the group consisting of anxiety disorder, panic disorder, agoraphobia, substance-induced anxiety disorder; depression, dysthymic disorder, bipolar I and bipolar II manic disorder; schizophrenia; insomnia, and epilepsy.

* * * * *